(12) United States Patent
Zemel et al.

(10) Patent No.: US 9,872,844 B2
(45) Date of Patent: *Jan. 23, 2018

(54) COMPOSITIONS AND METHODS FOR THE REDUCTION OR PREVENTION OF HEPATIC STEATOSIS

(71) Applicant: NUSIRT SCIENCES, INC., Nashville, TN (US)

(72) Inventors: Michael Zemel, Knoxville, TN (US); Antje Bruckbauer, Knoxville, TN (US)

(73) Assignee: NuSirt Sciences, Inc., Nashville, TN (US)

( * ) Notice: Subject to any disclaimer, the term of this patent is extended or adjusted under 35 U.S.C. 154(b) by 92 days.

This patent is subject to a terminal disclaimer.

(21) Appl. No.: 14/843,873

(22) Filed: Sep. 2, 2015

(65) Prior Publication Data

US 2016/0067201 A1    Mar. 10, 2016

Related U.S. Application Data

(63) Continuation-in-part of application No. PCT/US2015/018182, filed on Feb. 27, 2015.

(60) Provisional application No. 61/945,412, filed on Feb. 27, 2014.

(51) Int. Cl.
| | |
|---|---|
| *A61K 31/198* | (2006.01) |
| *A61K 45/06* | (2006.01) |
| *A61K 31/05* | (2006.01) |
| *A61K 31/155* | (2006.01) |
| *A61K 31/352* | (2006.01) |
| *A61K 31/4439* | (2006.01) |
| *A61K 31/4985* | (2006.01) |
| *A61K 31/519* | (2006.01) |
| *A61K 31/53* | (2006.01) |
| *A61K 31/522* | (2006.01) |
| *A61K 31/7048* | (2006.01) |

(52) U.S. Cl.
CPC ............ *A61K 31/198* (2013.01); *A61K 31/05* (2013.01); *A61K 31/155* (2013.01); *A61K 31/352* (2013.01); *A61K 31/4439* (2013.01); *A61K 31/4985* (2013.01); *A61K 31/519* (2013.01); *A61K 31/522* (2013.01); *A61K 31/53* (2013.01); *A61K 31/7048* (2013.01); *A61K 45/06* (2013.01)

(58) Field of Classification Search
None
See application file for complete search history.

(56) References Cited

U.S. PATENT DOCUMENTS

| | | |
|---|---|---|
| 3,810,994 A | 5/1974 | Wiegand |
| 3,936,527 A | 2/1976 | Alper |
| 4,606,909 A | 8/1986 | Bechgaard et al. |
| 4,769,027 A | 9/1988 | Baker et al. |
| 4,803,080 A | 2/1989 | Benedikt et al. |
| 4,897,268 A | 1/1990 | Tice et al. |
| 4,992,470 A | 2/1991 | Nissen |
| 5,069,204 A | 12/1991 | Smith et al. |
| 5,087,624 A | 2/1992 | Boynton et al. |
| 5,250,534 A | 10/1993 | Bell et al. |
| 5,339,771 A | 8/1994 | Axelrod |
| 5,395,626 A | 3/1995 | Kotwal et al. |
| 5,419,283 A | 5/1995 | Leo |
| 5,616,569 A | 4/1997 | Reinhart |
| 5,776,913 A | 7/1998 | Ogilvie et al. |
| 5,886,012 A | 3/1999 | Pang et al. |
| 5,968,569 A | 10/1999 | Cavadini et al. |
| 6,004,996 A | 12/1999 | Shah et al. |
| 6,031,000 A | 2/2000 | Nissen et al. |
| 6,048,903 A | 4/2000 | Toppo |
| 6,063,414 A | 5/2000 | Jones et al. |
| 6,063,820 A | 5/2000 | Cavazza |
| 6,224,861 B1 | 5/2001 | Abe et al. |
| 6,280,779 B1 | 8/2001 | Nadeau et al. |
| 6,338,862 B1 | 1/2002 | Niazi |
| 6,369,042 B1 | 4/2002 | Oberthur et al. |
| 6,384,087 B1 | 5/2002 | Zemel et al. |
| 6,387,419 B1 | 5/2002 | Christensen |
| 6,426,091 B1 | 7/2002 | Okumura et al. |
| 6,469,012 B1 | 10/2002 | Ellis et al. |
| 6,517,877 B2 | 2/2003 | Gannon |

(Continued)

FOREIGN PATENT DOCUMENTS

| | | |
|---|---|---|
| CN | 1504424 A | 6/2004 |
| CN | 102077936 A | 6/2011 |

(Continued)

OTHER PUBLICATIONS

Shalwala, M., Zhu, S. G., Das, A., Salloum, F. N., Xi, L., & Kukreja, R. C. (2010). SIRT1 Activation Mediates Sildenafil-Induced Cardioprotection Against Ischemia/Reperfusion Injury in Mice. Circulation, 122(Suppl 21), A14584-A14584.*

Musso, G., Cassader, M., Rosina, F., & Gambino, R. (2012). Impact of current treatments on liver disease, glucose metabolism and cardiovascular risk in non-alcoholic fatty liver disease (NAFLD): a systematic review and meta-analysis of randomised trials. Diabetologia, 55(4), 885-904.*

"Prevention" in Glossary of medical education terms: Parts 1-7. Wojtczak, A., Ed. Medical Teacher. vol. 24, Nos. 2-6 and vol. 25, No. 1&2. 2002.*

U.S. Appl. No. 15/164,647, filed May 25, 2016, Zemel et al.
U.S. Appl. No. 15/206,183, filed Jul. 8, 2016, Zemel et al.
European search report and opinion dated May 6, 2016 for EP Application No. 13854549.

(Continued)

*Primary Examiner* — Shaojia A Jiang
*Assistant Examiner* — Dale R Miller
(74) *Attorney, Agent, or Firm* — Wilson Sonsini Goodrich & Rosati

(57) ABSTRACT

Methods useful for reducing or preventing non-alcoholic steatohepatitis or hepatic steatosis are provided herein. Such methods may comprise administering to a subject in need thereof a sirtuin pathway activator and/or PDE5 inhibitor alone or in combination with an amount of a branched amino acid in free amino acid form, or a metabolite thereof. Also provided herein are compositions and kits for practicing any of the methods described herein.

22 Claims, 33 Drawing Sheets

(56) References Cited

U.S. PATENT DOCUMENTS

| | | |
|---|---|---|
| 6,527,711 B1 | 3/2003 | Stivoric et al. |
| 6,595,929 B2 | 7/2003 | Stivoric et al. |
| 6,605,038 B1 | 8/2003 | Teller et al. |
| 6,635,268 B2 | 10/2003 | Peery et al. |
| 6,638,545 B1 | 10/2003 | Rombi |
| 6,676,967 B1 | 1/2004 | Cefali et al. |
| 6,764,697 B1 | 7/2004 | Jao et al. |
| 6,790,869 B2 | 9/2004 | Ghai et al. |
| 6,797,283 B1 | 9/2004 | Edgren et al. |
| 6,919,373 B1 | 7/2005 | Lam et al. |
| 6,923,800 B2 | 8/2005 | Chen et al. |
| 6,929,803 B2 | 8/2005 | Wong et al. |
| 6,939,556 B2 | 9/2005 | Lautenbach |
| 7,020,508 B2 | 3/2006 | Stivoric et al. |
| 7,109,198 B2 | 9/2006 | Gadde et al. |
| 7,141,254 B2 | 11/2006 | Bhaskaran et al. |
| 7,153,262 B2 | 12/2006 | Stivoric et al. |
| 7,230,009 B2 | 6/2007 | Haque et al. |
| 7,261,690 B2 | 8/2007 | Teller et al. |
| 7,285,090 B2 | 10/2007 | Stivoric et al. |
| 7,354,738 B2 | 4/2008 | Spielgelman et al. |
| 7,495,101 B2 | 2/2009 | Fischesser et al. |
| 7,502,643 B2 | 3/2009 | Farringdon et al. |
| 7,674,485 B2 | 3/2010 | Bhaskaran et al. |
| 7,689,437 B1 | 3/2010 | Teller et al. |
| 7,722,905 B2 | 5/2010 | Khoo |
| 7,744,930 B2 | 6/2010 | Fisher et al. |
| 7,829,556 B2 | 11/2010 | Bemis et al. |
| 7,855,289 B2 | 12/2010 | Nunes et al. |
| 7,870,856 B2 | 1/2011 | Boeck |
| 7,893,086 B2 | 2/2011 | Bemis et al. |
| 7,959,567 B2 | 6/2011 | Stivoric et al. |
| 7,989,007 B2 | 8/2011 | Giuliano et al. |
| 8,008,458 B2 | 8/2011 | Zaloga et al. |
| 8,017,634 B2 | 9/2011 | Sinclair et al. |
| 8,044,198 B2 | 10/2011 | Nunes et al. |
| 8,073,707 B2 | 12/2011 | Teller et al. |
| 8,088,043 B2 | 1/2012 | Andren et al. |
| 8,088,044 B2 | 1/2012 | Tchao et al. |
| 8,088,928 B2 | 1/2012 | Nunes et al. |
| 8,093,401 B2 | 1/2012 | Nunes et al. |
| 8,106,097 B2 | 1/2012 | Najib |
| 8,157,731 B2 | 4/2012 | Teller et al. |
| 8,192,767 B2 | 6/2012 | Carta |
| 8,275,635 B2 | 9/2012 | Stivoric et al. |
| 8,299,083 B2 | 10/2012 | Kass et al. |
| 8,369,936 B2 | 2/2013 | Farringdon et al. |
| 8,370,549 B2 | 2/2013 | Burton et al. |
| 8,378,090 B2 | 2/2013 | Petiard et al. |
| 8,382,590 B2 | 2/2013 | Stivoric et al. |
| 8,398,546 B2 | 3/2013 | Pacione et al. |
| 8,403,845 B2 | 3/2013 | Stivoric et al. |
| 8,408,436 B2 | 4/2013 | Berry et al. |
| 8,469,862 B2 | 6/2013 | Andren et al. |
| 8,517,896 B2 | 8/2013 | Robinette et al. |
| 8,557,869 B2 | 10/2013 | Yamka et al. |
| 8,562,489 B2 | 10/2013 | Burton et al. |
| 8,597,677 B2 | 12/2013 | Yamka et al. |
| 8,617,886 B2 | 12/2013 | Zemel et al. |
| 8,623,924 B2 | 1/2014 | Zemel et al. |
| 9,072,692 B2 | 7/2015 | Zemel et al. |
| 9,198,454 B2 | 12/2015 | Zemel et al. |
| 9,198,883 B1 | 12/2015 | Zemel et al. |
| 9,351,967 B2 | 5/2016 | Zemel et al. |
| 9,408,410 B2 | 8/2016 | Zemel et al. |
| 9,408,834 B2 | 8/2016 | Zemel et al. |
| 9,585,876 B2 | 3/2017 | Zemel et al. |
| 9,682,053 B2 | 6/2017 | Zemel et al. |
| 9,707,213 B2 | 7/2017 | Zemel et al. |
| 9,724,319 B2 | 8/2017 | Zemel et al. |
| 2001/0043983 A1 | 11/2001 | Hamilton |
| 2003/0035882 A1 | 2/2003 | McDaniel et al. |
| 2003/0166662 A1 | 9/2003 | Fryburg et al. |
| 2003/0187055 A1 | 10/2003 | Riker et al. |
| 2004/0120983 A1 | 6/2004 | Connolly |
| 2004/0186046 A1 | 9/2004 | Burgess et al. |
| 2005/0042362 A1 | 2/2005 | Clark et al. |
| 2005/0064070 A1 | 3/2005 | Liebrecht |
| 2005/0100617 A1 | 5/2005 | Malnoe et al. |
| 2005/0215882 A1 | 9/2005 | Chenevert et al. |
| 2006/0051416 A1 | 3/2006 | Rastogi et al. |
| 2006/0111435 A1 | 5/2006 | Sinclair et al. |
| 2006/0159746 A1 | 7/2006 | Troup et al. |
| 2006/0165824 A1 | 7/2006 | Khambe |
| 2006/0188611 A1 | 8/2006 | Unlu et al. |
| 2006/0194743 A1 | 8/2006 | Oku et al. |
| 2006/0205633 A1 | 9/2006 | Nishitani et al. |
| 2007/0014833 A1 | 1/2007 | Milburn et al. |
| 2007/0065512 A1 | 3/2007 | Dedhiya et al. |
| 2007/0077310 A1 | 4/2007 | Zemel et al. |
| 2007/0092577 A1 | 4/2007 | Zemel et al. |
| 2007/0110850 A1 | 5/2007 | Rifkin |
| 2007/0190171 A1 | 8/2007 | Yamka et al. |
| 2007/0203083 A1 | 8/2007 | Mootha et al. |
| 2007/0244202 A1 | 10/2007 | Murase |
| 2007/0286909 A1 | 12/2007 | Smith et al. |
| 2008/0069862 A1 | 3/2008 | Hurwitz |
| 2008/0076828 A1 | 3/2008 | Dalton et al. |
| 2008/0102137 A1 | 5/2008 | Guffey |
| 2008/0176822 A1 | 7/2008 | Chen |
| 2008/0220092 A1 | 9/2008 | Dipierro et al. |
| 2008/0233245 A1 | 9/2008 | White et al. |
| 2008/0242727 A1 | 10/2008 | Romero et al. |
| 2008/0268038 A1 | 10/2008 | Wolfe |
| 2008/0286254 A1 | 11/2008 | Sakamoto et al. |
| 2009/0012183 A1 | 1/2009 | Draijer et al. |
| 2009/0017130 A1 | 1/2009 | Yamka et al. |
| 2009/0054450 A1 | 2/2009 | Currie et al. |
| 2009/0074827 A1 | 3/2009 | Scherl et al. |
| 2009/0105246 A1 | 4/2009 | Bemis et al. |
| 2009/0142336 A1 | 6/2009 | Walsh et al. |
| 2009/0156648 A1 | 6/2009 | Molino et al. |
| 2009/0163476 A1 | 6/2009 | Milburn et al. |
| 2009/0182036 A1 | 7/2009 | Krammer-Lukas |
| 2009/0197820 A1 | 8/2009 | Wolfe et al. |
| 2009/0230013 A1 | 9/2009 | Born et al. |
| 2010/0009992 A1 | 1/2010 | Bimberg et al. |
| 2010/0130597 A1 | 5/2010 | Chung et al. |
| 2010/0158956 A1 | 6/2010 | Komorowski |
| 2010/0173024 A1 | 7/2010 | McDaniel |
| 2010/0204204 A1 | 8/2010 | Zaworotko et al. |
| 2010/0210692 A1 | 8/2010 | Farmer et al. |
| 2010/0261793 A1 | 10/2010 | Caterson et al. |
| 2010/0303966 A1 | 12/2010 | Sunvold et al. |
| 2010/0303967 A1 | 12/2010 | Sunvold et al. |
| 2010/0304003 A1 | 12/2010 | Friesen et al. |
| 2010/0316679 A1 | 12/2010 | Sinclair et al. |
| 2010/0324002 A1 | 12/2010 | Fox et al. |
| 2011/0020443 A1 | 1/2011 | Liu et al. |
| 2011/0027416 A1 | 2/2011 | Sunvold et al. |
| 2011/0033559 A1 | 2/2011 | Zemel et al. |
| 2011/0038948 A1 | 2/2011 | Zemel et al. |
| 2011/0064712 A1 | 3/2011 | Amato |
| 2011/0064720 A1 | 3/2011 | Amato |
| 2011/0070258 A1 | 3/2011 | Jimenez Del et al. |
| 2011/0082189 A1 | 4/2011 | Sinclair et al. |
| 2011/0111066 A1 | 5/2011 | Ferguson et al. |
| 2011/0112047 A1 | 5/2011 | Evans et al. |
| 2011/0130387 A1 | 6/2011 | Nunes et al. |
| 2011/0165125 A1 | 7/2011 | Pan |
| 2011/0208153 A1 | 8/2011 | Alvey |
| 2012/0035105 A1* | 2/2012 | Geho .................... A61K 38/28 514/6.5 |
| 2012/0058088 A1 | 3/2012 | Sardi |
| 2012/0129785 A1 | 5/2012 | Fleuranges et al. |
| 2012/0177730 A1 | 7/2012 | Baron et al. |
| 2012/0225139 A1 | 9/2012 | Ferguson et al. |
| 2012/0289598 A1 | 11/2012 | Yamka et al. |
| 2012/0301559 A1 | 11/2012 | Pridmore-Merten et al. |
| 2013/0017283 A1 | 1/2013 | Zemel et al. |
| 2013/0017284 A1 | 1/2013 | Zemel et al. |
| 2013/0045193 A1 | 2/2013 | Gonzalez et al. |
| 2013/0052286 A1 | 2/2013 | Wada et al. |
| 2013/0151196 A1 | 6/2013 | Yuen et al. |

(56) References Cited

U.S. PATENT DOCUMENTS

| | | |
|---|---|---|
| 2013/0158369 A1 | 6/2013 | Yuen et al. |
| 2013/0237605 A1 | 9/2013 | Zemel et al. |
| 2013/0323287 A1 | 12/2013 | Komorowski |
| 2014/0057017 A1 | 2/2014 | Yamka et al. |
| 2014/0148488 A1 | 5/2014 | Zemel et al. |
| 2015/0056274 A1 | 2/2015 | Zemel et al. |
| 2016/0000737 A1 | 1/2016 | Zemel et al. |
| 2016/0008329 A1 | 1/2016 | Zemel et al. |
| 2016/0067201 A1 | 3/2016 | Zemel et al. |
| 2016/0279130 A1 | 9/2016 | Zemel et al. |
| 2017/0000780 A1 | 1/2017 | Zemel et al. |
| 2017/0239253 A1 | 8/2017 | Zemel et al. |

FOREIGN PATENT DOCUMENTS

| | | |
|---|---|---|
| EP | 1685833 A1 | 8/2006 |
| EP | 1818055 A1 | 8/2007 |
| EP | 2308493 A1 | 7/2009 |
| FR | 2710243 A1 | 3/1995 |
| GB | 1584539 A | 2/1981 |
| JP | 3219838 B2 | 10/2001 |
| JP | 2005097273 A | 4/2005 |
| JP | 2007306851 A | 11/2007 |
| JP | 2008-063321 A | 3/2008 |
| JP | 2008-063328 A | 3/2008 |
| WO | WO-2004056208 A1 | 7/2004 |
| WO | WO 2004/082401 A1 | 9/2004 |
| WO | WO-2005049006 A1 | 6/2005 |
| WO | WO-2005065667 A2 | 7/2005 |
| WO | WO-2007146124 A2 | 12/2007 |
| WO | WO-2007146313 A1 | 12/2007 |
| WO | WO 2011/051974 A1 | 5/2011 |
| WO | WO 2012/097064 A1 | 7/2012 |
| WO | WO-2013028547 A1 | 2/2013 |
| WO | WO-2013134736 A1 | 9/2013 |
| WO | WO-2013169007 A1 | 11/2013 |
| WO | WO-2014113404 A1 | 7/2014 |
| WO | WO-2014152016 A1 | 9/2014 |
| WO | WO-2015053379 A1 | 4/2015 |

OTHER PUBLICATIONS

Notice of allowance dated Feb. 1, 2016 for U.S. Appl. No. 14/927,255.
Notice of allowance dated Apr. 28, 2016 for U.S. Appl. No. 14/927,228.
Varma, et al. Chronic Tadalafil Therapy Improves Fasting Glucose Levels and Downregulates Microrna-103 and -107 in Obese Diabetic Mice. Circulation. 2012; 126: A14802. Abstract 14802.
U.S. Appl. No. 14/442,711, filed May 13, 2015, Zemel et al.
U.S. Appl. No. 14/746,516, filed Jun. 22, 2015, Zemel et al.
Agarwal. Cortisol metabolism and visceral obesity: role of 11beta-hydroxysteroid dehydrogenase type I enzyme and reduced co-factor NADPH. Endocr Res. Nov. 2003;29(4):411-8.
Alwine, et al. Method for detection of specific RNAs in agarose gels by transfer to diazobenzyloxymethyl-paper and hybridization with DNA probes. Proc Natl Acad Sci U S A. Dec. 1977;74(12):5350-4.
Amstad, et al. Mechanism of c-fos induction by active oxygen. Cancer Res. Jul. 15, 1992;52(14):3952-60.
Anthony, et al. Orally Administered Leucine Stimulates Protein Synthesis of Skeletal Muscle of Postabsorptive Rats in Association with Increased eIF4F Famiationl'2. The Journal of Nutrition. 2000; 130:139-145.
Argiles, et al. Cross-talk between skeletal muscle and adipose tissue: a link with obesity? Med Res Rev. Jan. 2005;25(1):49-65.
Atabek, et al. Oxidative stress in childhood obesity. J Pediatr Endocrinol Metab. Aug. 2004;17(8):1063-8.
Ayala, et al. Chronic treatment with sildenafil improves energy balance and insulin action in high fat-fed conscious mice. Diabetes. Apr. 2007;56(4):1025-33. Epub Jan. 17, 2007.
Banakar, et al. 1 alpha, 25-dihydroxyvitamin D3 prevents DNA damage and restores antioxidant enzymes in rat hepatocarcinogenesis induced by diethylnitrosamine and promoted by phenobarbital. World J Gastroenterol. May 1, 2004;10(9):1268-75.
Bender, et al. Cyclic nucleotide phosphodiesterases: molecular regulation to clinical use. Pharmacol Rev. Sep. 2006;58(3):488-520.
Berchtold. A simple method for direct cloning and sequencing cDNA by the use of a single specific oligonucleotide and oligo(dT) in a polymerase chain reaction (PCR). Nucleic Acids Res. Jan. 11, 1989;17(1):453.
Beta-hydroxy Beta-methylbutyrate (HMB). 2009; 1-2. http://exrx.net/Nutrition/Supplements/HMB.html.
Black grape ingredients. Power of resveratrol. Accessed: Sep. 29, 2010. www.blackgrapehealth.com/Tnt37/ingredients.php.
Blum, et al. SIRT1 modulation as a novel approach to the treatment of diseases of aging. J Med Chem. Jan. 27, 2011;54(2):417-32. Epub Nov. 16, 2010.
BodyBuilding, VitaMinder Power shaker, 2006, BodyBuilding.com, p. 1.
Bostrum, et al. A PGC1-α-dependent myokine that drives brown-fat-like development of white fat and thermogenesis. Nature. Jan. 11, 2012;481(7382):463-8. doi: 10.1038/nature10777.
Botanical Online 2010, 1-3. http//:www.botanical-online.com/english/plantschemicalagents.htm.
Boustany. Diabetes and grapefruit. 2010. ThinkScienceNow. 1-4. http://www.thinksciencenow.com/blog-post/diabetes-and-grapefruit/.
Brand, et al. Mitochondrial superoxide and aging: uncoupling-protein activity and superoxide production. Biochem Soc Symp. 2004;(71):203-13.
Breastfeeding.com. Q&A How many ounces of breast milk should I pump? 2010; 1-2. http://www.breastfeeding.com/breastfeeding-questions/breastfeeding-pumping-basics/qa/how-many-ounces-of-breast-milk-should-i-pumpp.aspx.
Brookes. Mitochondrial H(+) leak and ROS generation: an odd couple. Free Radic Biol Med. Jan. 1, 2005;38(1):12-23.
Bruckbauer, et al. Synergistic effects of leucine and resveratrol on insulin sensitivity and fat metabolism in adipocytes and mice. Nutr Metab (Lond). Aug. 22, 2012;9(1):77. doi: 10.1186/1743-7075-9-77.
Bruckbauer, et al. Synergistic effects of metformin, resveratrol, and hydroxymethylbutyrate on insulin sensitivity. Diabetes Met Syndr Obes 2013:6:93-102.
Bruckbauer, et al. Synergistic effects of polyphenols and methylxanthines with leucine on AMPK/sirtuin-mediated metabolism in muscle cells and adipocytes. PLoS One. 9(2):e89166. Feb. 14, 2014.
Bruckbauer, et al. The effects of dairy components on energy partitioning and metabolic risk in mice: a microarray study. J Nutrigenet Nutrigenomics. 2009;2(2):64-77. Epub Mar. 4, 2009.
Busquets, et al. Interleukin-15 decreases proteolysis in skeletal muscle: a direct effect. Int J Mol Med. Sep. 2005;16(3):471-6.
Carbo, et al. Interleukin-15 antagonizes muscle protein waste in tumour-bearing rats. Br J Cancer. Aug. 2000;83(4):526-31.
Carbo, et al. Interleukin-15 mediates reciprocal regulation of adipose and muscle mass: a potential role in body weight control. Biochim Biophys Acta. Apr. 3, 2001;1526(1):17-24.
Cerutti, et al. The role of the cellular antioxidant defense in oxidant carcinogenesis. Environ Health Perspect. Dec. 1994;102 Suppl 10:123-9.
Chalasani, et al. The diagnosis and management of non-alcoholic fatty liver disease: Practice guideline by the American Association for the Study of Liver Diseases, American College of Gastroenterology, and the American Gastroenterological Association. Hepatology 2012; 55:2005-2021.
Chang, et al. Mammalian MAP kinase signalling cascades. Nature. Mar. 1, 2001;410(6824):37-40.
Cheng, et al. Leucine deprivation decreases fat mass by stimulation of lipolysis in white adipose tissue and upregulation of uncoupling protein 1 (UCP1) in brown adipose tissue. Diabetes. Jan. 2010;59(1):17-25. Epub Oct. 15, 2009.
Chung, et al. Contribution of polyol pathway to diabetes-induced oxidative stress. J Am Soc Nephrol. Aug. 2003;14(8 Suppl 3):S233-6.

(56) References Cited

OTHER PUBLICATIONS

Clement, et al. Weight loss regulates inflammation-related genes in white adipose tissue of obese subjects. FASEB J. Nov. 2004;18(14):1657-69.
Cottam, et al. The chronic inflammatory hypothesis for the morbidity associated with morbid obesity: implications and effects of weight loss. Obes Surg. May 2004;14(5):589-600.
De Souza, et al. Insulin secretory defect in zucker FA/FA rats is improved by ameliorating insulin resistance. Diabetes. Aug. 1995;44(8):984-91.
Ding, et al. Amino acid composition of lactating mothers' milk and confinement diet in rural North China. Asia Pac J. Clin Nutr. 2010; 19(3):344-349.
Doi, et al. Isoleucine, a Blood Glucose-Lowering Amino Acid, Increases Glucose Uptake in Rat Skeletal Muscle in the Absence of Increases in AMP-Activated Protein Kinase Activity. J Nutr. Sep. 2005;135(9):2103-8.
Donato, et al. Effects of leucine supplementation on the body composition and protein status of rats submitted to food restriction. Nutrition. May 2006;22(5):520-7.
Duval, et al. Increased reactive oxygen species production with antisense oligonucleotides directed against uncoupling protein 2 in murine endothelial cells. Biochem Cell Biol. 2002;80(6):757-64.
Emerging risk factors collaboration. Diabetes mellitus, fasting glucose, and risk of cause-specific death. N Engl J Med. Mar. 3, 2011;364(9):829-41.
Erlanson-Albertsson. The role of uncoupling proteins in the regulation of metabolism. Acta Physiol Scand. Aug. 2003;178(4):405-12.
Ermak, et al. Calcium and oxidative stress: from cell signaling to cell death. Mol Immunol. Feb. 2002;38(10):713-21.
European search report and opinion dated Mar. 9, 2015 for EP Application No. 12814141.3.
European search report and opinion dated Sep. 28, 2015 for EP Application No. 13758140.1.
Fain, et al. Comparison of the release of adipokines by adipose tissue, adipose tissue matrix, and adipocytes from visceral and subcutaneous abdominal adipose tissues of obese humans. Endocrinology. May 2004;145(5):2273-82. Epub Jan. 15, 2004.
Feige, et al. Specific SIRT1 activation mimics low energy levels and protects against diet-induced metabolic disorders by enhancing fat oxidation. Supplemental infouation. Cell Metab. Nov. 2008;8(5):347-58.
Feige, et al. Specific SIRT1 activation mimics low energy levels and protects against diet-induced metabolic disorders by enhancing fat oxidation. Cell Metab. Nov. 2008;8(5):347-58. Erratum Cell Metab. Feb. 2009;9(2):210.
Festi, et al. Hepatic steastosis in obese patients: clinical aspects and prognostic significance. Obesity Rev 2004; 5:27-42.
Flatt, et al. Direct and indirect actions of nutrients in the regulation of insulin secretion from the pancreatic beta cells. Proc Nutr Soc. Dec. 1991;50(3):559-66.
Fortamet (Metformin Hydrochloride) Extended-Release Tablets Label. http://www.accessdata.fda.gov/drugsatfda_docs/label/2008/021574s0101bl.pdf. Accessed Jul. 6, 2015.
Fried, et al. Omental and subcutaneous adipose tissues of obese subjects release interleukin-6: depot difference and regulation by glucocorticoid. J Clin Endocrinol Metab. Mar. 1998;83(3):847-50.
Furukawa, et al. Increased oxidative stress in obesity and its impact on metabolic syndrome. J Clin Invest. Dec. 2004;114(12):1752-61.
Gerlinger-Romero, et al. Chronic supplementation of beta-hydroxy-beta methylbutyrate (HMβ) increases the activity of the GH/IGF-I axis and induces hyperinsulinemia in rats. Growth Horm IGF Res. Apr. 2011;21(2):57-62. doi: 10.1016/j.ghir.2010.12.006. Epub Jan. 14, 2011.
Girl, et al. Constitutive activation of NF-kappaB causes resistance to apoptosis in human cutaneous T cell lymphoma HuT-78 cells. Autocrine role of tumor necrosis factor and reactive oxygen intermediates. J Biol Chem. May 29, 1998;273(22):14008-14.
Goldman, et al. Generation of reactive oxygen species in a human keratinocyte cell line: role of calcium. Arch Biochem Biophys. Feb. 1, 1998;350(1):10-8.
Goldstein, et al. Adiponectin: A novel adipokine linking adipocytes and vascular function. J Clin Endocrinol Metab. Jun. 2004;89(6):2563-8.
Gordeeva, et al. Cross-talk between reactive oxygen species and calcium in living cells. Biochemistry (Mosc). Oct. 2003;68(10):1077-80.
Hale, et al. Transfer of metforimin into human milk. Diabetologia. 2002; 45:1509-1514.
Harwood, et al. Isozyme-nonselective N-Substituted Bipiperidylcarboxamide Acetyl-CoA Carboxylase Inhibitors Reduce Tissue Malonyl-CoA Concentrations, Inhibit Fatty Acid Synthesis, and Increase Fatty Acid Oxidation in Cultured Cells and in Experimental Animals. The Journal of Biological Chemistry. Sep. 26, 2003; 278(39):37099-37111.
Hollander, et al. Induction of fos RNA by DNA-damaging agents. Cancer Res. Apr. 1, 1989;49(7):1687-92.
Hotamisligil, et al. Tumor necrosis factor alpha inhibits signaling from the insulin receptor. Proc Natl Acad Sci U S A. May 24, 1994;91(11):4854-8.
Hou, et al. Sirt1 regulates hepatocyte lipid metabolism through activating AMPK-activated protein kinase. J Biol Chem 2008; 383:20015-20026.
Howells, et al. Phase I randomized, double-blind pilot study of micronized resveratrol (SRT501) in patients with hepatic metastases—safety, pharmacokinetics, and pharmacodynamics. Cancer Prev Res (Phila). Sep. 2011;4(9):1419-25. Epub Jun. 16, 2011.
Hydroxymethyl Butyrate (HMB). Beth Israel Deaconess Medical Center. Accessed Dec. 13, 2012. http://www.bidmc.org/YourHealth/HolisticHealth/HerbsandSupplements.aspx?ChunkID=21551.
Inoguchi, et al. High glucose level and free fatty acid stimulate reactive oxygen species production through protein kinase C—dependent activation of NAD(P)H oxidase in cultured vascular cells. Diabetes. Nov. 2000;49(11):1939-45.
International search report and written opinion dated May 28, 2013 for PCT Application No. US2013/030044.
International search report and written opinion dated Feb. 8, 2007 for PCT Application No. US2006/038854.
International search report and written opinion dated Mar. 10, 2014 for PCT Application No. US2013/069957.
International search report and written opinion dated May 22, 2015 for PCT/US2015/018182.
International search report and written opinion dated Nov. 29, 2012 for PCT Application No. US2012/046814.
JillWillRun. Hydration Review Nuun, 2009, pp. 1-8.
Khan, et al. Induction of renal oxidative stress and cell proliferation response by ferric nitrilotriacetate (Fe-NTA): diminution by soy isoflavones. Chem Biol Interact. Aug. 10, 2004;149(1):23-35.
Kiens. Skeletal Muscle Lipid Metabolism in Exercise and Insulin Resistance. Physiological Reviews. 2006;86: 205-243.
Koren, et al. Vitamin D is a prooxidant in breast cancer cells. Cancer Res. Feb. 15, 2001;61(4):1439-44.
Korshunov, et al. High protonic potential actuates a mechanism of production of reactive oxygen species in mitochondria. FEBS Lett. Oct. 13, 1997;416(1):15-8.
Kouzarides, et al. Leucine zippers of fos, jun and GCN4 dictate dimerization specificity and thereby control DNA binding. Nature. Aug. 17, 1989;340(6234):568-71.
Krishnaswamy, et al. Effect of vitamin B6 on leucine-induced changes in human subjects. Am J Clin Nutr. Feb. 1976;29(2):177-81.
Layman. The role of leucine in weight loss diets and glucose homeostasis. Journal of Nutrition, 2003, 133, 261S-267S.
Lee, et al. The evolving role of inflammation in obesity and the metabolic syndrome. Curr Diab Rep. Feb. 2005;5(1):70-5.
Leenders, et al. Leucine as a pharmaconutrient to prevent and treat sarcopenia and type 2 diabetes. Nutr Rev. Nov. 2011;69(11):675-89. doi: 10.1111/j.1753-4887.2011.00443.x. Abstract only.
Li, et al. Evaluation of antioxidant capacity and aroma quality of breast milk. Nutrition. 2008; 25(1):1-3.

(56) References Cited

OTHER PUBLICATIONS

Li, et al. Leucine nutrition in animals and humans: mTOR signaling and beyond. Amino Acids. Nov. 2011;41(5):1185-93. Epub Jul. 20, 2011.

Li, et al. Visceral fat: higher responsiveness of fat mass and gene expression to calorie restriction than subcutaneous fat. Exp Biol Med (Maywood). Nov. 2003;228(10):1118-23.

Lin, et al. Increased oxidative damage with altered antioxidative status in type 2 diabetic patients harboring the 16189 T to C variant of mitochondrial DNA. Ann N Y Acad Sci. May 2005;1042:64-9.

Lin. Suppression of protein kinase C and nuclear oncogene expression as possible action mechanisms of cancer chemoprevention by Curcumin. Arch Pharm Res. Jul. 2004;27(7):683-92.

Lind, et al. Evaluation of four different methods to measure endothelium-dependent vasodilation in the human peripheral circulation. Clin Sci (Lond). May 2002;102(5):561-7.

Lira, et al. Nitric oxide and AMPK cooperatively regulate PGC-1 in skeletal muscle cells. J Physiol. Sep. 15, 2010;588(Pt 18):3551-66. Epub Jul. 19, 2010.

Lumeng, et al. Plasma content of B6 vitamers and its relationship to hepatic vitamin B6 metabolism. J Clin Invest. Oct. 1980; 66(4): 688-695.

Lynch, et al. Leucine is a direct-acting nutrient signal that regulates protein synthesis in adipose tissue. Am J Physiol Endocrinol Metab. Sep. 2002;283(3):E503-13.

Macotela, et al. Dietary Leucine—an environmental modifier of insulin resistance acting on multiple levels of metabolism. PLoS One. 2011;6(6):e21187. Epub Jun. 22, 2011.

Mahadev, et al. The NAD(P)H oxidase homolog Nox4 modulates insulin-stimulated generation of H2O2 and plays an integral role in insulin signal transduction. Mol Cell Biol. Mar. 2004;24(5):1844-54.

Manders, et al. Nutrition and disease co-ingestion of a protein hydrolysate with or without additional leucine effectively reduces postprandial blood glucose excursions in type 2 diabetic men 1. Jan. 1, 2006. 1294-1299. http://jn.nutrition.org/content/136/5/1294.full.pdf.

Manea, et al. Changes in oxidative balance in rat pericytes exposed to diabetic conditions. J Cell Mol Med. Jan.-Mar. 2004;8(1):117-26.

Melnik. Leucine signaling in the pathogenesis of type 2 diabetes and obesity. World J Diabetes. Mar. 15, 2012;3(3):38-53. doi: 10.4239/wjd.v3.i3.38.

Melton, et al. Efficient in vitro synthesis of biologically active RNA and RNA hybridization probes from plasmids containing a bacteriophage SP6 promoter. Nucleic Acids Res. Sep. 25, 1984;12(18):7035-56.

Merck Manual Home Edition online article entitled, "Multiple Sclerosis"—accessed Jun. 20, 2010 at http://www.merck.com/mmhe/print/sec06/ch092/ch092b.html.

Merck Manual Home Edition online article entitled, "Introduction: Coronary Artery Disease"—accessed Jun. 20, 2010 at www.merck.com/mmhe/print/sec03/ch033/ch033a.html.

Miwa, et al. Mitochondrial matrix reactive oxygen species production is very sensitive to mild uncoupling. Biochem Soc Trans. Dec. 2003;31(Pt 6):1300-1.

Morris, et al. 1,25-dihydroxyvitamin D3 modulation of adipocyte glucocorticoid function. Obes Res. Apr. 2005;13(4):670-7.

Nairizi, et al. Leucine supplementation of drinking water does not alter susceptibility to diet-induced obesity in mice. Nutr. Apr. 2009;139(4):715-9. Epub Feb. 25, 2009.

Nisoli, et al. Mitochondrial biogenesis by NO yields functionally active mitochondria in mammals. Proc Natl Acad Sci U S A. Nov. 23, 2004;101(47):16507-12. Epub Nov. 15, 2004.

Nisoli, et al. Mitochondrial biogenesis in mammals: the role of endogenous nitric oxide. Science. Feb. 7, 2003;299(5608):896-9.

Nomura, et al. Inhibition of 12-O-tetradecanoylphorbol-13-acetate-induced NF-kappaB activation by tea polyphenols, (−)-epigallocatechin gallate and theaflavins. Carcinogenesis. Oct. 2000;21(10):1885-90.

Notice of allowance dated Mar. 6, 2015 for U.S. Appl. No. 13/866,936.
Notice of allowance dated Mar. 15, 2013 for U.S. Appl. No. 13/549,381.
Notice of allowance dated Apr. 25, 2013 for U.S. Appl. No. 11/542,703.
Notice of allowance dated Apr. 29, 2015 for U.S. Appl. No. 13/866,936.
Notice of allowance dated May 29, 2013 for U.S. Appl. No. 13/549,399.
Notice of allowance dated Aug. 13, 2013 for U.S. Appl. No. 13/549,381.
Notice of allowance dated Aug. 15, 2013 for U.S. Appl. No. 13/549,399.
Notice of allowance dated Sep. 1, 2015 for U.S. Appl. No. 13/662,345.
Notice of allowance dated Sep. 11, 2015 for U.S. Appl. No. 14/746,516.
Notice of allowance dated Dec. 28, 2012 for U.S. Appl. No. 13/549,399.

Ofei, et al. Effects of an engineered human anti-TNF-alpha antibody (CDP571) on insulin sensitivity and glycemic control in patients with NIDDM. Diabetes. Jul. 1996;45(7):881-5.

Office action dated Feb. 5, 2015 for U.S. Appl. No. 13/662,345.
Office action dated Apr. 22, 2013 for U.S. Appl. No. 13/662,345.
Office action dated Jun. 25, 2010 for U.S. Appl. No. 11/543,171.
Office action dated Jul. 15, 2010 for U.S. Appl. No. 11/542,703.
Office action dated Sep. 16, 2013 for U.S. Appl. No. 13/662,345.
Office action dated Nov. 7, 2012 for U.S. Appl. No. 13/549,381.
Office action dated Dec. 23, 2010 for U.S. Appl. No. 11/542,703.
Office action dated Dec. 23, 2010 for U.S. Appl. No. 11/543,171.

Panichi, et al. Calcitriol modulates in vivo and in vitro cytokine production: a role for intracellular calcium. Kidney Int. Nov. 1998;54(5):1463-9.

Park, et al. Resveratrol ameliorates aging-related metabolic phenotypes by inhibiting cAMP phosphodiesterases. Cell. Feb. 3, 2012;148(3):421-33.

Patterson, et al. Excretion of tryptophan-niacin metabolites by young men: effects of tryptophan, leucine, and vitamin B6 intakes. Am J Clin Nutr. Oct. 1980;33(10):2157-67.

Pearce, et al. Sports supplements: A modern case of caveat emptor. Current Sports Medicine Reports. 2005; 4:171-178.

Peterson, et al. The mechanism of transamination. Function of the histidyl residue at the active site of supernatant aspartate transaminase. J Biol Chem. Feb. 25, 1970;245(4):806-13.

Povolny, et al. The role of recombinant human M-CSF, IL-3, GM-CSF and calcitriol in clonal development of osteoclast precursors in primate bone marrow. Exp Hematol. Apr. 1993;21(4):532-7.

Price, et al. SIRT1 is required for AMPK activation and the beneficial effects of resveratrol on mitochondrial function. Cell Metab. May 2, 2012;15(5):675-90. doi: 10.1016/j.cmet.2012.04.003.

Purushotham, et al. Hepatocyte-specific deletion of Sirt1 alters fatty acid metabolism and results in hepatic steatosis and inflammation. Cell Metabolism 2009; 9:327-338.

Quinn, et al. Interleukin-15 stimulates adiponectin secretion by 3T3-L1 adipocytes: evidence for a skeletal muscle-to-fat signaling pathway. Cell Biol Int. Jun. 2005;29(6):449-57.

Rasmussen, et al. Regulation of fatty acid oxidation in skeletal muscle. Annu Rev Nutr. 1999;19:463-84.

Reeves. Components of the AIN-93 diets as improvements in the AIN-76A diet. J Nutr. May 1997;127(5 Suppl):838S-841S.

Remington's Pharmaceutical Sciences 18th Edition. 1990, Martin ed., Mack Publishing Co., PA.

Roberts, et al. Nutrition and aging: changes in the regulation of energy metabolism with aging. Physiol Rev. Apr. 2006;86(2):651-67.

S Bear. Nother way to get leucine for the 6 week cure, 2009, pp. 1-5.

Sabatini, et al. Tadalafil alters energy metabolism in C2C12 skeletal muscle cells. Acta Biochim Pol. 2011;58(2):237-41. Epub Jun. 16, 2011.

Schulze-Osthoff, et al. Oxidative stress and signal transduction. Int J Vitam Nutr Res. 1997;67(5):336-42.

(56) References Cited

OTHER PUBLICATIONS

Sellden, et al. Augmented thermic effect of amino acids under general anaesthesia: a mechanism useful for prevention of anaesthesia-induced hypothellnia. Clin Sci (Load). May 1994;86(5):611-8.

Shangari, et al. The cytotoxic mechanism of glyoxal involves oxidative stress. Biochem Phaimacol. Oct. 1, 2004;68(7):1433-42.

Shi, et al. 1alpha,25-dihydroxyvitamin D3 inhibits uncoupling protein 2 expression in human adipocytes. FASEB J. Nov. 2002;16(13):1808-10. Epub Sep. 5, 2002.

Shi, et al. 1alpha,25-Dihydroxyvitamin D3 modulates human adipocyte metabolism via nongenomic action. FASEB J. Dec. 2001;15(14):2751-3. Epub Oct. 15, 2001.

Simeone, et al. How retinoids regulate breast cancer cell proliferation and apoptosis. Cell Mol Life Sci. Jun. 2004;61(12):1475-84.

Soares, et al. Effects of oxidative stress on adiponectin secretion and lactate production in 3T3-L1 adipocytes. Free Radic Biol Med. Apr. 1, 2005;38(7):882-9.

Solerte, et al. Metabolic effects of orally administered amino acid mixture in elderly subjects with poorly controlled type 2 diabetes mellitus. Am J Cardiol. Apr. 22, 2004;93(8A):23A-29A.

Song, et al. Methionine-induced hyperhomocysteinemia promotes superoxide anion generation and NFkappaB activation in peritoneal macrophages of C57BL/6 mice. J Med Food. 2004 Summer;7(2):229-34.

Sonta, et al. Evidence for contribution of vascular NAD(P)H oxidase to increased oxidative stress in animal models of diabetes and obesity. Free Radic Biol Med. Jul. 1, 2004;37(1):115-23.

Sorescu, et al. Superoxide production and expression of nox family proteins in human atherosclerosis. Circulation. Mar. 26, 2002;105(12):1429-35.

Stipanuk. Leucine and protein synthesis: mTOR and beyond. Nutr Rev. Mar. 2007;65(3):122-9.

Sun, et al. 1, 25(OH)2D3 and reactive oxygen species interatively stimulate angiotensinogen expression in differentiated 3T3-L1 adipocytes. FASEB J. 2005; 19:A70, No. 67.8 (abstract only).

Sun, et al. Calcium and dairy products inhibit weight and fat regain during ad libitum consumption following energy restriction in Ap2-agouti transgenic mice. J Nutr. Nov. 2004;134(11):3054-60.

Sun, et al. Dietary calcium regulates ROS production in aP2-agouti transgenic mice on high-fat/high-sucrose diets. Int J Obes (Lond). Sep. 2006;30(9):1341-6. Epub Mar. 7, 2006.

Sun, et al. Dual effects of 1-alpha,25-(OH)2-D3 on adipocyte apoptosis. FASEB J. 2004; 18:A49 (abstract only).

Sun, et al. Effects of mitochondrial uncoupling on adipocyte intracellular Ca(2+) and lipid metabolism. J Nutr Biochem. Apr. 2003;14(4):219-26.

Sun, et al. Leucine and calcium regulate fat metabolism and energy partitioning in murine adipocytes and muscle cells. Lipids. Apr. 2007;42(4):297-305. Epub Feb. 20, 2007.

Sun, et al. Leucine modulation of mitochondrial mass and oxygen consumption in skeletal muscle cells and adipocytes. Nutr Metab (Lond). Jun. 5, 2009;6:26. doi:10.1186/1743-7075-6-26.

Sun, et al. Reactive oxygen species stimulate cell proliferation and down-regulate UCP2 expression in 3T3-L1 adipocytes. Obesity Research. 2004; 11: A21, No. 80-OR (abstract only).

Sun, et al. Role of uncoupling protein 2 (UCP2) expression and 1alpha, 25-dihydroxyvitamin D3 in modulating adipocyte apoptosis. FASEB J. Sep. 2004;18(12):1430-2. Epub Jul. 1, 2004.

Suzuki, et al. Oxidants as stimulators of signal transduction. Free Radic Biol Med. 1997;22(1-2):269-85.

Suzuki, et al. Relationship between obesity and serum markers of oxidative stress and inflammation in Japanese. Asian Pac J Cancer Prev. Jul.-Sep. 2003;4(3):259-66.

Tappy, et al. Thermic effect of infused amino acids in healthy humans and in subjects with insulin resistance. Am J Clin Nutr. Jun. 1993;57(6):912-6.

Tennen, et al. Finding a target for resveratrol. Cell. Feb. 3, 2012;148(3):387-9.

Thannickal, et al. Reactive oxygen species in cell signaling. Am J Physiol Lung Cell Mol Physiol. Dec. 2000;279(6):L1005-28.

Thompson, et al. Effect of energy-reduced diets high in dairy products and fiber on weight loss in obese adults. Obes Res. Aug. 2005;13(8):1344-53.

Thomson, et al. Effects of nine weeks of beta-hydroxy-beta-methylbutyrate supplementation on strength and body composition in resistance trained men. Journal of strength and conditioning research / National Strength & Conditioning Association 23: 827-835, 2009.

Upham, et al. Hydrogen peroxide inhibits gap junctional intercellular communication in glutathione sufficient but not glutathione deficient cells. Carcinogenesis. Jan. 1997;18(1):37-42.

Valle, et al. Low-grade systemic inflammation, hypoadiponectinemia and a high concentration of leptin are present in very young obese children, and correlate with metabolic syndrome. Diabetes Metab. Feb. 2005;31(1):55-62.

Van Loon. Leucine as a pharmaconutrient in health and disease. Curr Opin Clin Nutr Metab Care. Jan. 2012;15(1):71-7. Abstract only.

Verdin, et al. Sirtuin regulation of mitochondria: energy production, apoptosis, and signaling. Trends Biochem Sci. Dec. 2010;35(12):669-75. Epub Sep. 20, 2010.

Vernon et al. Systematic review: The epidemiology and natural history of non-alcoholic fatty liver disease and non-alcoholic steatohepatitis in adults. Aliment Pharmacol 2011; 34:274-285.

Volk, et al. Transient Ca2+ changes in endothelial cells induced by low doses of reactive oxygen species: role of hydrogen peroxide. Mol Cell Biochem. Jun. 1997;171(1-2):11-21.

Wajchenberg. Subcutaneous and visceral adipose tissue: their relation to the metabolic syndrome. Endocr Rev. Dec. 2000;21(6):697-738.

Warner. Metformin Linked to B12 Deficiency, 2009, WebMD, pp. 1-2.

Weisberg, et al. Obesity is associated with macrophage accumulation in adipose tissue. J Clin Invest. Dec. 2003;112(12):1796-808.

Weitzman, et al. Free radical adducts induce alterations in DNA cytosine methylation. Proc Natl Acad Sci U S A. Feb. 15, 1994;91(4):1261-4.

Wilson, et al. Effects of beta-hydroxy-beta-methylbutyrate (HMB) on exercise performance and body composition across varying levels of age, sex, and training experience: A review. Nutr Metab (Lond). Jan. 3, 2008;5:1.

Wiseman, et al. Damage to DNA by reactive oxygen and nitrogen species: role in inflammatory disease and progression to cancer. Biochem J. Jan. 1, 1996;313 ( Pt 1):17-29.

Xiao, et al. Leucine deprivation increases hepatic insulin sensitivity via GCN2/mTOR/S6K1 and AMPK pathways. Diabetes. Mar. 2011;60(3):746-56. Epub Jan. 31, 2011.

Xu, et al. Chronic inflammation in fat plays a crucial role in the development of obesity-related insulin resistance. J Clin Invest. Dec. 2003;112(12):1821-30.

Xue, et al. Relationship between human adipose tissue agouti and fatty acid synthase (FAS). J Nutr. Oct. 2000;130(10):2478-81.

Xue, et al. The agouti gene product inhibits lipolysis in human adipocytes via a Ca2+-dependent mechanism. Faseb J. Oct. 1998;12(13):1391-6.

Yang, et al. Leucine metabolism in regulation of insulin secretion from pancreatic beta cells. Nutr Rev. May 2010;68(5):270-9.

Zanchi, et al. Potential antiproteolytic effects of L-leucine: observations of in vitro and in vivo studies. Nutr Metab (Lond). Jul. 17, 2008;5:20.

Zemel, et al. Calcium and dairy acceleration of weight and fat loss during energy restriction in obese adults. Obes Res. Apr. 2004;12(4):582-90.

Zemel, et al. Dairy augmentation of total and central fat loss in obese subjects. Int J Obes (Lond). Apr. 2005;29(4):391-7.

Zemel, et al. Effects of dairy compared with soy on oxidative and inflammatory stress in overweight and obese subjects. Am J Clin Nutr. Jan. 2010;91(1):16-22. Epub Nov. 4, 2009.

Zemel, et al. Regulation of adiposity by dietary calcium. FASEB J. Jun. 2000;14(9):1132-8.

(56) References Cited

OTHER PUBLICATIONS

Zemel, et al. Effects of calcium and dairy on body composition and weight loss in African-American adults. Obes Res. Jul. 2005;13(7):1218-25.
Zemel. Calcium and dairy modulation of obesity risk. Obes Res. Jan. 2005;13(1):192-3.
Zemel. Role of calcium and dairy products in energy partitioning and weight management. Am J Clin Nutr. May 2004;79(5):907S-912S.
Zemel. The role of dairy foods in weight management. J Am Coll Nutr. Dec. 2005;24(6 Suppl):537S-46S.
Zhang, et al. Increasing dietary leucine intake reduces diet-induced obesity and improves glucose and cholesterol metabolism in mice via multimechanisms. Diabetes. Jun. 2007;56(6):1647-54. Epub Mar. 14, 2007.
Zhang, et al. Occurrence of beta-hydroxyl-beta-methyl butyrates in foods and feed. Protein and amini acid nutrition. 1994; A464: 2685-2690.
Zoraghi, et al. Phosphodiesterase-5 Gln817 is critical for cGMP, vardenafil, or sildenafil affinity: its orientation impacts cGMP but not cAMP affinity. J Biol Chem. Mar. 3, 2006;281(9):5553-8. Epub Jan. 5, 2006.
Anonymous: European commission health and consumer protection directorate-general directorate C-scientific opinions c2-management of scientific committees II; scientific co-operation and networks opinion of the scientific committee on food on the tolerable upper intake levels of nicotinic acid and nicotinamide, May 6, 2002. Available at: http://ec.europa.eu/foods/fs/sc/scf/out80j_en.pdf. Retrieved on Sep. 21, 2016.
Anonymous: GRAS notification for L-Leucine produced by innonio limited, May 27, 2014, Available at: http://www.fda.gov/ucm/groups/fdagov-public/@fdaov-foods-gen/documents/document/ucm407679.pdf. Retrieved on Sep. 21, 2016.
Arend, et al. Inhibition of the production and effects of interleukin-1 and tumor necrosis factor alpha in rheumatoid arthritis. Arthritis Rheum. Feb. 1995;38(2):151-60.
Balabolkin, et al., The role of thiazolidinediones in compensation of carbohydrate metabolism in type 2 diabetes and in the prevention of vascular complications of diabetes. 1998-2017. Retrieved from: https://www.lvrach.ru/2007/02/4534786/.
Bannowsky, A. et al., Recovery of erectile function after nerve-sparing radical prostatectomy: improvement with nightly low-dose sildenafil. BJU Int., Feb. 18, 2008, vol. 101, No. 10, pp. 1279-1283.
Bartges, et al. Calculating a patient's nutritional requirements. Veterinary Medicine. 2004; 99:632.
Brennan, et al. Inhibitory effect of TNF alpha antibodies on synovial cell interleukin-1 production in rheumatoid arthritis. Lancet. Jul. 29, 1989;2(8657):244-7.
Carlson, LA. Nicotinic acid: the broad-spectrum lipid drug. A 50th anniversary review. J Intern Med. Aug. 2005;258(2):94-114.
Carroll, et al. Antagonism of the IL-6 cytokine subfamily—a potential strategy for more effective therapy in rheumatoid arthritis. Inflamm Res. Jan. 1998;47(1):1-7.
Caton, et al., Metformin opposes impaired AMPK and SIRT1 function and deleterious changes in core clock protein expression in white adipose tissue of genetically-obese db/db mice. Diabetes Obes Metab 13, 1097-1104 Dec. 13, 2011.
Co-pending U.S. Appl. No. 15/513,115, filed Mar. 21, 2017.
Co-pending U.S. Appl. No. 15/595,911, filed May 15, 2017.
Co-pending U.S. Appl. No. 15/619,406, filed Jun. 9, 2017.
Co-pending U.S. Appl. No. 15/638,241, filed Jun. 29, 2017.
Creider, et al., Niacin: another look at an underutilized lipid-lowering medication. Nature Reviews Endocrinology, 2012. 8:517-528.
Dell'Agli et al., Potent inhibition of human phosphodiesterase-5 by icariin derivatives, Journal of Natural Products, Sep. 9, 2008, vol. 71, No. 9, p. 1513-1517.
European search report and opinion dated Aug. 22, 2016 for EP Application No. 14770824.

European Search Report dated Sep. 30, 2016 for European Application No. 14768984.8.
Fraquelli, M. et al., Reproducibility of transient elastography in the evaluation of liver fibrosis in patients with chronic liver disease. Gut. Jan. 25, 2007, vol. 56; pp. 968-973; Abstract; pp. 969 1st column, 2nd paragraph; DOI 10.1136/gut.2006.111302.
Fu, L., et al., Interaction between leucine and phosphodiesterase 5 inhibition in modulating insulin sensitivity and lipid metabolism. Diabetes, Metabolic syndrome and obesity:Targets and therapy. May 6, 2015; vol. 8: pp. 227-239.; abstract; p. 228, 1st column, 3rd paragraph to 2nd column, 1st paragraph.
Gilhuly, K. Niacin Dosage for lowering Triglycerides. Livestrong. Jul. 27, 2015. Available at: http://www.livestrong.com/article/460725-the-dosage-of-niacin-for-lowering-triglycerides/#ixzz2N03KhDZu. Accessed on Jun. 8, 2017.
Haworth, et al. Expression of granulocyte-macrophage colony-stimulating factor in rheumatoid arthritis: regulation by tumor necrosis factor-alpha. Eur J Immunol. Oct. 1991;21(10):2575-9.
Hornstra, et al. Essential fatty acids in pregnancy and early human development. Eur J Obstet Gynecol Reprod Biol. Jul. 1995;61(1):57-62.
Howitz, K.T. et al., Small molecule activators of sirtuins extend *Saccharomyces cerevisiae* lifespan. Letters to Nature. 2003; 425:191-196.
International search report and written opinion dated Jul. 21, 2014 for PCT/US2014/016592.
International Search report and Written opinion dated Sep. 19, 2016 for Singapore Application No. 11201503774P.
International search report dated Jul. 14, 2014 for PCT Application No. US 2014/026816.
International Search Report dated Nov. 28, 2016 for International Application No. PCT/US2016/049272.
Ionut, et al. Novel canine models of obese prediabetes and mild type 2 diabetes. Am J Physiol Endocrinol Metab. Jan. 2010;298(1):E38-48. doi: 10.1152/ajpendo.00466.2009. Epub Oct. 20, 2009.
Kies, E. et al., Interrelationship of leucine with lysine, tryptophan, and niacin as they influence protein value of cereal gains for humans. Cereal Chemistry. Apr. 1972; 223-231.
Kuda, et al., n-3 fatty acids and rosiglitazone improve insulin sensitivity through additive stimulatory effects on muscle glycogen synthesis in mice fed a high-fat diet, Diabetologia, Mar. 11, 2009, vol. 52, No. 5, p. 941-951.
Laflamme. Development and validation of a body condition score system for dogs. Canine Practice. 1997; 22:10-15.
Lehman, et al. Assessment of coronary plaque progression in coronary computed tomography angiography using a semiquantitative score. JACC Cardiovasc Imaging. Nov. 2009;2(11):1262-70. doi: 10.1016/j.jcmg.2009.07.007.
Li, et al., Leucine supplementation increases SIRTI expression and prevents mitochondrial dysfunction and metabolic disorders in high-fat diet-induced obese mice. Am J Physiology. Endocrinology and metabolism, Sep. 11, 2012; 303(10): p. E1234-E1244.
Lim, et al. Intakes of dietary docosahexaenoic acid ethyl ester and egg phosphatidylcholine improve maze-learning ability in young and old mice. J Nutr. Jun. 2000;130(6):1629-32.
Manna, et al., Resveratrol Suppresses TNF-Induced Activation of Nuclear Transcription Factors NF-κB, Activator Protein-1, and Apoptosis: Potential Role of Reactive Oxygen Intermediates and Lipid Peroxidation1. J Immunol 2000; 164:6509-6519.
Matsui, et al., Metformin reduces body weight gain and improves glucose intolerance in high-fat diet-fed C57BL/6J mice, Biological and Pharmaceutical Bulletin, Jun. 2010, vol. 33, No. 6, p. 963-970.
Mawby, et al. Comparison of various methods for estimating body fat in dogs. J Am Anim Hosp Assoc. Mar.-Apr. 2004;40(2):109-14.
Mooney, et al., Mechanisms underlying the metabolic actions of galegine that contribute to weight loss in mice. Br J Pharmacol. Apr. 2008; 153(8): 1669-1677. Published online Feb. 25, 2008. doi: 10.1038/bjp.2008.37.
Moser, et al. Interleukin 1 and tumor necrosis factor stimulate human vascular endothelial cells to promote transendothelial neutrophil passage. J Clin Invest. Feb. 1989;83(2):444-55.
Muscle Synergy: Advanced Nitric Oxide and muscle building supplement. Beverly International. Accessed on Oct. 18, 2012.

(56) References Cited

OTHER PUBLICATIONS

Available at: https://web.archive.org/web/20121018004354/http://www.beverlyinternational.com/products/muscle-synergy.html.

Musso, G. et al., Impact of current treatments on liver disease, glucose metabolism and cardiovascular risk in non-alcoholic fatty liver disease (NAFLD): a systematic review and meta-analysis of randonmised trials. Diabetologia (2012) 55:885-904.

Nagao, et al. Dietary diacylglycerol suppresses accumulation of body fat compared to triacylglycerol in men in a double-blind controlled trial. J Nutr. Apr. 2000;130(4):792-7.

Nakagawa, I. Effect of an excess intake of leucine, with and without additions of vitamin B6 and/or niacin, on tryptophan and niacin metabolism in rats. Journal of nutritional science and vitaminology. 23(6). Jan. 1, 1977. p. 535-548.

Nin, et al., Role of deleted in breast cancer 1 (DBC1) protein in SIRT1 deacetylase activation induced by protein kinase A and AMP-activated protein kinase. J Biol Chem. Jul. 6, 2012;287(28):23489-501. doi: 10.1074/jbc.M112.365874. Epub May 2, 2012.

Notice of allowance dated Feb. 27, 2017 for U.S. Appl. No. 15/164,647.

Notice of Allowance dated Mar. 23, 2017 for U.S. Appl. No. 15/206,125.

Notice of allowance dated Apr. 11, 2016 for U.S. Appl. No. 14/472,081.

Notice of Allowance dated Apr. 27, 2017 for U.S. Appl. No. 15/119,695.

Notice of Allowance dated Aug. 18, 2017 for U.S. Appl. No. 15/595,911.

Notice of Allowance dated Oct. 26, 2016 for U.S. Appl. No. 14/772,366.

Office Action dated Apr. 5, 2017 for U.S. Appl. No. 14/843,873.

Office Action dated Jul. 28, 2017 for U.S. Appl. No. 14/442,711.

Office Action dated Dec. 15, 2016 for U.S. Appl. No. 14/770,418.

OpenSource Diets. Product Data D12451. Report Repeat Revise Where NutriPhenomics Begins Research Diets, Inc. 20. Last modified: Feb. 28, 2013.

Ouyang, et al., Metformin Activates AMP Kinase through Inhibition of AMP Deaminase. J Biol Chern 286, 1-11 Jan. 7, 2011.

Park, et al. Resveratrol ameliorates aging-related metabolic phenotypes by inhibiting cAMP phosphodiesterases. Cell. Feb. 3, 2012;148(3):421-33. doi: 10.1016/j.cell.2012.01.017.

Phan, et al. Effects of niacin on glucose levels, coronary stenosis progression, and clinical events in subjects with normal baseline glucose levels (<100 mg/dl): a combined analysis of the Familial Atherosclerosis Treatment Study (FATS), HDL-Atherosclerosis Treatment Study (HATS), Armed Forces Regression Study (AFREGS), and Carotid Plaque Composition by MRI during lipid-lowering (CPC) study. Am J Cardiol. Feb. 1, 2013;111(3):352-5. doi: 10.1016/j.amjcard.2012.09.034. Epub Nov. 17, 2012.

Rogers. A healthy body, a healthy mind: long-term impact of diet on mood and cognitive function. Proc Nutr Soc. Feb. 2001;60(1):135-43.

Saumet, et al. Non-invasive measurement of skin blood flow: comparison between plethysmography, laser-Doppler flowmeter and heat thermal clearance method. Int J Microcirc Clin Exp. 1986;5(1):73-83.

Shalwala, M. B., A novel role of sirtl in sildenafil induced cardioprotection in mice. Virginia Commonwealth University—Master Thesis, May 2010, pp. 1-56.

Shalwala, M., et al., SIRT1 Activation Mediates Sildenafil-Induced Cardioprotection Against Ischemia/Reperfusion Injury in Mice. Circulation, 122(Suppl 21 ), 2010: A 14584-A 14584.

Truswell, A.S. Effect of surplus leucine intake on serum cholesterol in man. Proceedings of the nutrition society. 23(2). Sep. 1, 1964. pp. XLVI-XLVII.

Uckert, S & Oelke, M, Phosphodiesterase (PDE) inhibitors in the treatment of lower urinary tract dysfunction, British Journal of Clinical Pharmacology, 2011, vol. 72, No. 2, p. 197-204.

Sunvold, et al. Dietary fiber for dogs: IV. In vitro fermentation of selected fiber sources by dog fecal inoculum and in vivo digestion and metabolism of fiber-supplemented diets. J Anim Sci. Apr. 1995;73(4):1099-109.

Witters, L.A., The blooming of the French lilac. J Clin Invest. Oct. 15, 2001; 108(8): 1105-1107. doi: 10.1172/JCI14178.

Wojtczak, A., "Prevention" in glossary of medical education terms: Parts 1-7. Ed. Medical Teacher. vol. 24, Nos. 2-6 and vol. 25, No. 1 &2. 2002.

Yalkowsky, et al. Potentiometric titration of monomeric and micellar acylcarnitines. J Pharm Sci. Jun. 1970;59(6):798-802.

Yalkowsky, et al. Some micellar properties of long-chain acylcarnitines. J Colloid Interface Sci. Dec. 1970;34(4):525-33.

Yamka, et al. In vivo measurement of flatulence and nutrient digestibility in dogs fed poultry by-product meal, conventional soybean meal, and low-oligosaccharide low-phytate soybean meal. Am J Vet Res. Jan. 2006;67(1):88-94.

Yudkin, et al. Inflammation, obesity, stress and coronary heart disease: is interleukin-6 the link? Atherosclerosis. Feb. 2000;148(2):209-14.

* cited by examiner

Liver Histology

Liver Fibrosis via Picrosirius Red Staining

COMPOSITIONS AND METHODS FOR THE REDUCTION OR PREVENTION OF HEPATIC STEATOSIS

This application is a continuation-in-part application of International Application No. PCT/US2015/018182, filed on Feb. 27, 2015, which claims priority to U.S. Provisional Patent Application No. 61/945,412, filed on Feb. 27, 2014, the content of each of which is hereby incorporated by reference in their entirety.

INCORPORATION BY REFERENCE

All publications, patents, and patent applications mentioned in this specification are herein incorporated by reference to the same extent as if each individual publication, patent or patent application was specifically and individually indicated to be incorporated by reference. In case of any inconsistency between the incorporated by reference publications and the instant specification, the instant specification will control.

BACKGROUND OF THE INVENTION

Hepatic steatosis, also sometimes referred to as fatty liver disease, is a condition generally characterized by an abnormal retention of lipids in cells of the liver. Hepatic steatosis affects millions of people worldwide. For example, the prevalence of fatty liver disease has been estimated to range from 10-24% in various countries around the globe. Fatty liver disease can have various causes. For example, non-alcoholic fatty liver disease (NAFLD) generally refers to a spectrum of hepatic lipid disorders characterized by hepatic steatosis with no known secondary cause. NAFLD can be subcategorized into (a) non-alcoholic fatty liver (NAFL), defined as the presence of steatosis in the absence of histological evidence of hepatocellular injury, and (b) non-alcoholic steatohepatitis (NASH), hepatic steatosis accompanied by hepatocyte injury and inflammation; NASH may occur with or without fibrosis, but may progress to fibrosis and cirrhosis. NAFLD is generally associated with energy metabolism pathologies, including obesity, dyslipidemia, diabetes and metabolic syndrome. The prevalence of NAFLD is high. Prevalence in the general population is estimated at 20%, with prevalence of NASH estimated to be 3-5%. There is an estimated ~70% prevalence of NAFLD among patients with obesity or diabetes, and an estimated prevalence of ~50% prevalence of NAFLD among patients with dyslipidemias. However, there are presently no approved pharmaceuticals for the treatment of NAFLD/NASH.

Sirtuins are highly conserved protein deacetylases and/or ADP-ribosyltransferases that have been shown to extend lifespan in lower model organisms, such as yeast, *C. elegans*, and *drosophila*. In mammals, sirtuins have been shown to act as metabolic sensors, responding to environmental signals to coordinate the activity of genes that regulate multiple energy homeostasis pathways. For example, studies have shown that sirtuin activation mimics the effects of caloric restriction, an intervention demonstrated to significantly extend lifespan, and activates genes that improve glucose homeostasis and the conversion of fat to energy by fatty acid oxidation.

The sirtuin pathway may be defined as any pathway incorporating or converging upon pathways mediated by phosphodiesterases (PDEs). PDEs are enzymes that interact with cyclic adenosine monophosphates (cAMPs) and cyclic guanosine monophosphates (cGMPs). The PDE family of enzymes comprises multiple subclasses, including PDE 1-11 in humans. Inhibitors of these phosphodiesterases can prevent the inactivation of cAMPs and cGMPs, and can have a variety of different physiological effects. The PDE inhibitors can be selective, by preferentially inhibiting one PDE subclass as compared to another subclass, or non-selective, which have a substantially lower degree of selectivity for individual PDE subclasses. Sildenafil is an example of a selective PDE inhibitor that has shown selective inhibition of PDE 5. Sildenafil is a pharmaceutically active agent that has been used to treat pulmonary hypertension, erectile dysfunction, and altitude sickness.

SUMMARY OF THE INVENTION

The present invention generally relates to regulation of fat accumulation in cells and/or tissue. In some embodiments, the present invention provides for compositions, methods, and kits for reducing, treating, preventing, or sustaining the reduction of non-alcoholic steatohepatitis or hepatic steatosis in a subject in need thereof.

The invention provides a method for reducing non-alcoholic steatohepatitis (NASH) or hepatic steatosis in a subject in need thereof comprises administering to the subject: (a) an amount of leucine in the form of a free amino acid and/or metabolite thereof and (b) an amount of a sirtuin pathway activator, wherein the administering of (a) and (b) reduces non-alcoholic steatohepatitis (NASH) or hepatic steatosis to a greater extent than administration of (a) alone, thereby reducing non-alcoholic steatohepatitis (NASH) or hepatic steatosis in the subject. The invention also provides a method of reducing non-alcoholic steatohepatitis (NASH) or hepatic steatosis in a subject in need thereof, comprising administering to the subject: (a) an amount of leucine in the form of a free amino acid and/or metabolite thereof, and (b) an amount of a PDE-5 specific inhibitor, wherein the administering of a) and b) reduces non-alcoholic steatohepatitis (NASH) or hepatic steatosis to a greater extent than administration of (a) alone, thereby reducing non-alcoholic steatohepatitis (NASH) or hepatic steatosis in the subject. In some embodiments, the subject has been diagnosed with said non-alcoholic steatohepatitis (NASH) or hepatic steatosis. In some embodiments, the subject exhibits a non-alcoholic fatty liver disease (NAFLD). In some embodiments, the NAFLD is selected from the group consisting of non-alcoholic fatty liver (NAFL), non-alcoholic steatohepatitis (NASH) and NASH-related cirrhosis. In some embodiments, the subject exhibits one or more symptoms of non-alcoholic steatohepatitis (NASH) or hepatic steatosis selected from the group consisting of weakness, fatigue, unexplained weight loss, ache and jaundice. In some embodiments, the reduction in non-alcoholic steatohepatitis (NASH) or hepatic steatosis is characterized by a reduction in hepatic liver vacuole number or size or density. In some embodiments, the method can further comprising administering to the subject (c) a second sirtuin pathway activator.

The invention also provides a method of preventing non-alcoholic steatohepatitis (NASH) or hepatic steatosis in a subject exhibiting a propensity to non-alcoholic steatohepatitis (NASH) or hepatic steatosis, comprising administering to the subject prior to manifestation of a non-alcoholic steatohepatitis (NASH) or hepatic steatosis symptom: (a) an amount of leucine in the form of a free amino acid and/or metabolite thereof, and (b) an amount of a sirtuin pathway activator, wherein the administering of (a) and (b) reduces non-alcoholic steatohepatitis (NASH) or hepatic steatosis to a greater extent than administration of (a) alone, thereby preventing non-alcoholic steatohepatitis (NASH) or hepatic steatosis in the subject. The invention also provides a method of preventing non-alcoholic steatohepatitis (NASH) or hepatic steatosis in a subject exhibiting a propensity to non-alcoholic steatohepatitis (NASH) or hepatic steatosis, comprising administering to the subject prior to manifestation of a non-alcoholic steatohepatitis (NASH) or hepatic steatosis symptom: (a) an amount of leucine in the form of a free amino acid and/or metabolite thereof, and (b) an amount of a PDE-5 specific inhibitor, wherein the administering of (a) and (b) reduces non-alcoholic steatohepatitis (NASH) or hepatic steatosis to a greater extent than administration of (a) alone, thereby preventing non-alcoholic steatohepatitis (NASH) or hepatic steatosis in the subject. In some embodiments, the method can further comprising administering to the subject (c) a second sirtuin pathway activator.

The invention also provides a method of reducing non-alcoholic steatohepatitis (NASH) or hepatic steatosis in a subject in need thereof. The method comprises administering to the subject a composition comprising: (a) an amount of leucine in the form of a free amino acid; (b) an amount of metformin; and (c) an amount of sildenafil. In some embodiments, the administering of (a), (b) and (c) reduces non-alcoholic steatohepatitis (NASH) or hepatic steatosis to a greater extent than administration of (a) alone, thereby reducing non-alcoholic steatohepatitis (NASH) or hepatic steatosis in the subject.

The invention also provides a method of preventing non-alcoholic steatohepatitis (NASH) or hepatic steatosis in a subject exhibiting a propensity to non-alcoholic steatohepatitis (NASH) or hepatic steatosis, comprising administering to the subject prior to manifestation of a non-alcoholic steatohepatitis (NASH) or hepatic steatosis symptom a composition comprising: (a) an amount of leucine in the form of a free amino acid; (b) an amount of metformin; and (c) an amount of sildenafil. In some embodiments, the administering of (a), (b) and (c) reduces non-alcoholic steatohepatitis (NASH) or hepatic steatosis to a greater extent than administration of (a) alone, thereby preventing non-alcoholic steatohepatitis (NASH) or hepatic steatosis in the subject. In some embodiments, the method can further comprise administering to the subject a second sirtuin pathway activator.

In some embodiments of any of the foregoing methods, the subject is administered periodically over a course of at least 2 months. In some embodiments, the non-alcoholic steatohepatitis (NASH) or hepatic steatosis is evidenced by accumulation of fat in hepatic cells detectable by one or more methods selected from the group consisting of ultrasonography, computed tomography (CT), magnetic resonance imaging, measurement of serum alanine transaminase and aspartate transaminase, and biopsy. In some embodiments, the reduction of non-alcoholic steatohepatitis (NASH) or hepatic steatosis in the subject is evidenced by a reduction in hepatic fat detectable by one or more methods selected from the group consisting of ultrasonography, computed tomography (CT), magnetic resonance imaging measurement of serum alanine transaminase and aspartate transaminase, and biopsy. In some embodiments, the leucine metabolite thereof is β-hydroxy β-methylbutyrate (HMB) or keto-isocaproic acid (KIC).

In some embodiments, the amount of leucine administered to the subject is about 0.25-3 g/day. In some embodiments, the amount of leucine administered to the subject is about 0.25-3 g. In some embodiments, the amount of leucine metabolite administered to the subject is about 0.2-3 g/day.

In some embodiments, the amount of leucine metabolite administered to the subject is about 0.2-3 g. In some embodiments, a weight (wt) % of the leucine in the composition, excluding fillers, is 50-95 wt %. In some embodiments, a wt % of the leucine metabolite in the composition, excluding fillers, is 50-95 wt %. In some embodiments, a wt % of the sirtuin pathway activator in the composition, excluding fillers, is 5-50 wt %. In some embodiments, the molar ratio of leucine to sirtuin pathway activator is at least about 20. In some embodiments, component (a) is hydroxymethylbutyrate and component (b) is metformin. In some embodiments, (a) is leucine existing in form of a free amino acid and component (b) is metformin.

In some embodiments, the sirtuin pathway activator is a sirtuin activator. In some embodiments, the sirtuin activator is resveratrol. In some embodiments, the sirtuin activator is a polyphenol selected from the group consisting of chlorogenic acid, resveratrol, caffeic acid, cinnamic acid, ferulic acid, piceatannol, ellagic acid, epigallocatechin gallate, grape seed extract, and any analog thereof. In some embodiments, the amount of resveratrol administered to the subject is 0.5-100 mg/day. In some embodiments, the amount of chlorogenic acid, caffeic acid, cinnamic acid, ferulic acid, piceatannol, ellagic acid, epigallocatechin gallate, or grape seed extract, or any analog thereof administered to the subject is 0.5-500 mg/day.

In some embodiments, the PDE-5 specific inhibitor is selected from the group consisting of icariin, sildenafil, tadalafil, vardenafil, avanafil, lodenafil, mirodenafil and udenafil. In some embodiments, the amount of icariin administered to the subject is 1-2000 mg/day. In some embodiments, the amount of sildenafil administered to the subject is 0.05-100 mg/day. In some embodiments, the amount of tadalafil administered to the subject is 0.01-20 mg/day. In some embodiments, the amount of vardenafil administered to the subject is 0.01-20 mg/day. In some embodiments, the amount of avanafil administered to the subject is 1-200 mg/day. In some embodiments, the amount of lodenafil administered to the subject is 1-200 mg/day. In some embodiments, the amount of mirodenafil administered to the subject is 1-100 mg/day. In some embodiments, the amount of udenafil administered to the subject is 1-200 mg/day. In some embodiments, the amount of zaprinast administered to the subject is 1-2000 mg/day.

In some embodiments, the sirtuin pathway activator is an AMPK activator. In some embodiments, AMPK activator is a biguanide. In some embodiments, the biguanide is metformin. In some embodiments, the amount of metformin is a therapeutic amount of metformin. In some embodiments, the therapeutic amount of metformin is about 1 g/day to about 2.55 g/day. In some embodiments, the therapeutic amount of metformin is about 0.5 g to about 1.25 g. In some embodiments, the amount of metformin is a sub-therapeutic amount of metformin. In some embodiments, the sub-therapeutic amount of metformin is about 20-1000 mg metformin/day. In some embodiments, the sub-therapeutic amount of metformin is about 10-500 mg metformin.

In some embodiments, the sirtuin pathway activator is a PGC-1α activator. In some embodiments, the PGC-1α activator is a thiazolidinedione. In some embodiments, the thiazolidinedione is selected from the group consisting of rosiglitazone and pioglitazone. In some embodiments, the amount of rosiglitazone administered is 0.1-4 mg. In some embodiments, the amount of pioglitazone administered is 0.1-45 mg. In some embodiments, the amount of sirtuin pathway activator is a sub-therapeutic amount.

In some embodiments, the method further comprises administering to the subject a second sirtuin pathway activator. In some embodiments, the sirtuin pathway activator comprises a biguanide and the second sirtuin pathway activator comprises a sirtuin activator. In some embodiments, the sirtuin pathway activator comprises a sirtuin activator and the second sirtuin pathway activator comprises a thiazolidinedione. In some embodiments, the sirtuin pathway activator comprises a sirtuin activator and the second sirtuin pathway activator comprises a PDE5-specific inhibitor. In some embodiments, the sirtuin pathway activator comprises a biguanide and the second sirtuin pathway activator comprises a thiazolidinedione. In some embodiments, the sirtuin pathway activator comprises a biguanide and the second sirtuin pathway activator comprises a PDE5-specific inhibitor. In some embodiments, the sirtuin pathway activator comprises a thiazolidinedione and the second sirtuin pathway activator comprises a PDE5-specific inhibitor.

In some embodiments, the amounts of (a) and (b) are co-administered. In some embodiments, the amounts of (a) and (b) are administered simultaneously as a single composition. In some embodiments, the amounts of (a) and (b) are administered sequentially. In some embodiments, all of the amounts are administered sequentially within 15 minutes, 60 minutes or 2 hours. In some embodiments, all components of the composition are administered 15 minutes, 60 minutes or 2 hours. In some embodiments, the method comprises administering (a) and (b) 1, 2, 3, 4, 5 or more times per day. In some embodiments, the method comprises administering (a) and (b) 3 times daily and the liver mass of the subject is decreased by 25% within 6 weeks. In some embodiments, the composition is substantially free of one or more free amino acids selected from the group consisting of alanine, arginine, asparagine, aspartic acid, cysteine, glutamic acid, glutamine, glycine, histidine, isoleucine, lysine, methionine, phenylalanine, proline, serine, threonine, tryptophan, tyrosine, and valine.

In some other embodiments, the present invention relates to a composition comprising: (a) an amount of leucine in the form of a free amino acid; (b) an amount of metformin; and (c) an amount of sildenafil. In some embodiments, the amount of leucine is between about 50-95 wt % of the total wt of (a), (b), and (c), the amount of metformin is between about 5-50 wt % of the total wt of (a), (b), and (c), and the amount of sildenafil is between about 0.01-1 wt % of the total wt of (a), (b), and (c). In some embodiments, the composition is formulated as a unit dose comprising about 900-1200 mg of leucine, about 200-550 mg of metformin, and about 0.1 to 10 mg of sildenafil. In some embodiments, the composition is administered twice a day.

In one aspect, the invention provides a method of sustaining a reduction of non-alcoholic steatohepatitis (NASH) in a subject, the method comprising: (a) measuring a level of one or more biomarkers or physiological indicators of non-alcoholic steatohepatitis (NASH) in the subject; (b) administering to the subject a pharmaceutical composition comprising: (i) an amount of leucine in the form of a free amino acid and/or a metabolite thereof; (ii) an amount of metformin and/or an amount of sildenafil; and (c) monitoring the level of the one or more biomarkers or physiological indicators in the subject, wherein the one or more biomarkers is selected from the group consisting of transforming growth factor (TGF)-β, cytokeratin 18, aspartate transaminase (AST), and gamma glutamyl transferase (GGT). In some cases, the transforming growth factor (TGF)-β, cytokeratin 18, aspartate transaminase (AST), and gamma glutamyl transferase (GGT) are evaluated by measuring their respective serum levels in the subject. In some cases, the physiological indicator is liver stiffness evaluated by performing transient elastography (TE).

The invention also provides a method of sustaining a reduction of non-alcoholic steatohepatitis (NASH) in a subject, the method comprising: (a) measuring a level of one or more biomarkers or physiological indicators of non-alcoholic steatohepatitis (NASH) in a subject; (b) administering to the subject a pharmaceutical composition comprising: (i) an amount of leucine in the form of a free amino acid and/or a metabolite thereof; (ii) an amount of metformin and/or an amount of sildenafil; and (c) monitoring said level of the one or more biomarkers or physiological indicators in the subject, wherein the pharmaceutical composition is administered at least once a day, wherein beginning 2 weeks after commencement of administration of the pharmaceutical composition, the biomarker is reduced by at least 10%, and wherein the reduction of the biomarker is sustained for at least 8 weeks after the commencement. In some cases, the biomarker is sustained for at least 12 weeks. In some cases, the biomarker is reduced by at least 20% beginning 2 weeks after the commencement and sustained at such reduced level until at least 8 weeks after the commencement. In some cases, the biomarker is a serum level of alanine transaminase (ALT).

Practice of any of the foregoing methods can reduce a level of one or more biomarkers or physiological indicators of non-alcoholic steatohepatitis (NASH). In some embodiments, a decrease of level of said one or more biomarkers or physiological indicators in said subject indicates a sustained reduction of non-alcoholic steatohepatitis (NASH) in said subject.

The invention also provides a pharmaceutical composition formulated for reducing non-alcoholic steatohepatitis (NASH) in a subject, the pharmaceutical composition comprising: (a) an amount of leucine in the form of a free amino acid or metabolite thereof; and (b) an amount of sildenafil, wherein leucine is administered in a tablet or a capsule that does not contain sildenafil. The pharmaceutical composition can further comprise (c) an amount of metformin, wherein the amount of leucine, excluding fillers, is between about 50-95 wt % of a total wt of (a), (b) and (c), the amount of metformin, excluding fillers, is between about 5-50 wt % of a total wt of (a), (b), and (c), and the amount of sildenafil, excluding fillers, is between about 0.01-1 wt % of a total wt of (a), (b), and (c).

Subjects benefit from any of the foregoing inventions can include, but are not limited to, subjects who had been diagnosed with or exhibit a propensity to non-alcoholic steatohepatitis (NASH), and subjects who had been diagnosed or exhibit a non-alcoholic fatty liver disease (NAFLD), such as non-alcoholic fatty liver, non-alcoholic steatohepatitis (NASH), and NASH-related cirrhosis. In some cases, the subject has non-alcoholic steatohepatitis (NASH).

In some embodiments, the subject is administered a pharmaceutical composition comprising two or more tablets or capsules. The two or more tablets or capsules can comprise leucine in the form of free amino acid and/or a metabolite thereof, metformin, and/or sildenafil. In some cases, the subject is administered an amount of leucine in a tablet or a capsule that does not contain sildenafil. In some cases, the pharmaceutical composition disclosed herein comprises an amount of metformin and an amount of sildenafil administered in the same tablet or capsule, or in different tablets or capsules. In some cases, the amount of metformin and the amount of sildenafil are administered in the same tablets or capsules. In some cases, the pharmaceutical composition is formulated for oral administration. In some cases, the pharmaceutical composition is administered once a day or twice a day.

The pharmaceutical composition for administration in any of the foregoing methods can comprise various amounts of leucine and/or metabolite thereof, metformin and sildenafil formulated in a tablet or a capsule. In some embodiments, the pharmaceutical composition comprises two or more tablets or capsules comprising different amounts, or the same amount of leucine and/or metabolite thereof. The pharmaceutical composition can comprises between about 0.25-3 g, or between about 0.5-1.1 g of leucine in the form of a free amino acid and/or a metabolite thereof. In some embodiments, the pharmaceutical composition comprises two or more tablets or capsules comprising different amounts, or the same amount of metformin. The pharmaceutical composition comprises between about 0.01-2.55 g, or between about 0.1-0.5 g of metformin. In some embodiments, the pharmaceutical composition comprises two or more tablets or capsules comprising different amounts, or the same amount of sildenafil. The pharmaceutical composition comprises between about 0.1-3 g, or between about 0.3-2 g of sildenafil.

In some embodiments, the pharmaceutical composition for administration in any of the foregoing methods is substantially free of one or more free amino acids selected from the group consisting of alanine, arginine, asparagine, aspartic acid, cysteine, glutamic acid, glutamine, glycine, histidine, isoleucine, lysine, methionine, phenylalanine, proline, serine, threonine, tryptophan, tyrosine, and valine.

INCORPORATION BY REFERENCE

All publications, patents, and patent applications mentioned in this specification are herein incorporated by reference to the same extent as if each individual publication, patent, or patent application was specifically and individually indicated to be incorporated by reference.

BRIEF DESCRIPTION OF THE DRAWINGS

The novel features of the invention are set forth with particularity in the appended claims. A better understanding of the features and advantages of the present invention will be obtained by reference to the following detailed description that sets forth illustrative embodiments, in which the principles of the invention are utilized, and the accompanying drawing(s) of which:

DETAILED DESCRIPTION OF THE INVENTION

Figure 1:
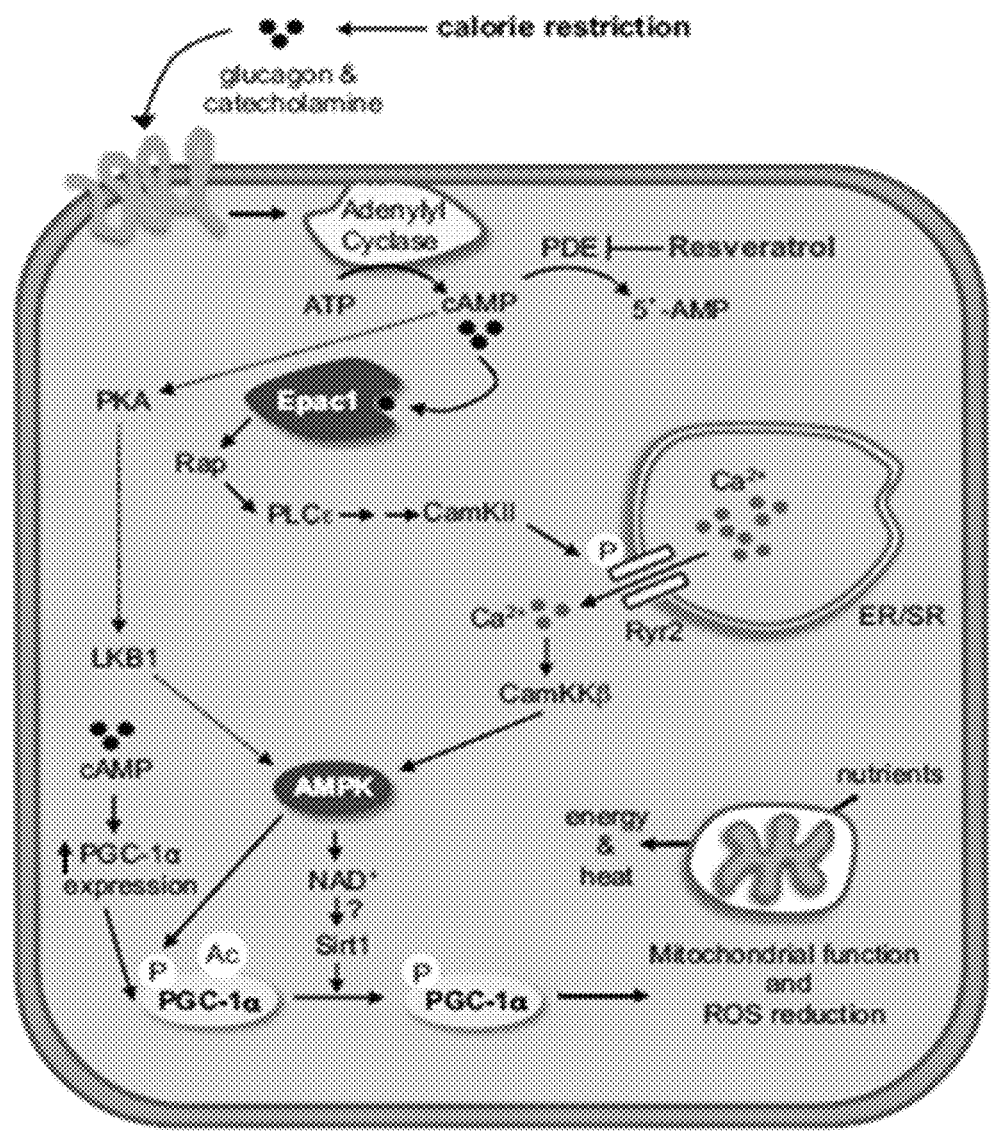
FIG. 1 depicts a sirtuin pathway.

Several aspects of the invention are described below with reference to example applications for illustration. It should be understood that numerous specific details, relationships, and methods are set forth to provide a full understanding of the invention. One having ordinary skill in the relevant art, however, will readily recognize that the invention can be practiced without one or more of the specific details or with other methods. Unless stated otherwise, the present invention is not limited by the illustrated ordering of acts or events, as some acts may occur in different orders and/or concurrently with other acts or events. Furthermore, not all illustrated acts or events are required to implement a methodology in accordance with the present invention. The concentrations of various components in the disclosed compositions are exemplary and not meant to be limited to the recited concentration per se.

As used herein, the singular forms "a", "an" and "the" include plural references unless the context clearly dictates otherwise. For example, the term "a cell" includes a plurality of cells, including mixtures thereof.

The terms "determining", "measuring", "evaluating", "assessing," "assaying," "interrogating," and "analyzing" are used interchangeably herein to refer to any form of measurement, and include determining if an element is present or not. These terms include both quantitative and/or qualitative determinations. Assessing may be relative or absolute.

As used herein, the term "subject" or "individual" includes mammals. Non-limiting examples of mammals include humans and mice, including transgenic and non-transgenic mice. The methods described herein can be useful in both human therapeutics, pre-clinical, and veterinary applications. In some embodiments, the subject is a mammal, and in some embodiments, the subject is human. Other mammals include, and are not limited to, apes, chimpanzees, orangutans, monkeys; domesticated animals (pets) such as dogs, cats, guinea pigs, hamsters, mice, rats, rabbits, and ferrets; domesticated farm animals such as cows, buffalo, bison, horses, donkey, swine, sheep, and goats; or exotic animals typically found in zoos, such as bear, lions, tigers, panthers, elephants, hippopotamus, rhinoceros, giraffes, antelopes, sloth, gazelles, zebras, wildebeests, prairie dogs, koala bears, kangaroo, pandas, giant pandas, hyena, seals, sea lions, and elephant seals.

As used herein, "agent" or "biologically active agent" refers to a biological, pharmaceutical, or chemical compound or other moiety. Non-limiting examples include simple or complex organic or inorganic molecule, a peptide, a protein, a peptide nucleic acid (PNA), an oligonucleotide (including e.g., aptomer and polynucleotides), an antibody, an antibody derivative, antibody fragment, a vitamin derivative, a carbohydrate, a toxin, a branched chain amino acid in free amino acid form or metabolite thereof, or a chemotherapeutic compound. Various compounds can be synthesized, for example, small molecules and oligomers (e.g., oligopeptides and oligonucleotides), and synthetic organic compounds based on various core structures. In addition, various natural sources can provide compounds for screening, such as plant or animal extracts, and the like. A skilled artisan can readily recognize that there is no limit as to the structural nature of the agents of the present invention.

The terms "administer", "administered", "administers" and "administering" are defined as the providing a composition to a subject via a route known in the art, including but not limited to intravenous, intraarterial, oral, parenteral, buccal, topical, transdermal, rectal, intramuscular, subcutaneous, intraosseous, transmucosal, or intraperitoneal routes of administration. In certain embodiments of the subject application, oral routes of administering a composition may be preferred.

As used herein, the terms "co-administration", "administered in combination with" and their grammatical equivalents are meant to encompass administration of the invention composition and additional therapeutic agent to a single subject. Co-administration can encompass administration of two or more agents to an animal so that both agents and/or their metabolites are present in the subject at the same time. Co-administration can encompass treatment regimens in which the composition and additional therapeutic agent are administered by the same or different route of administration or at the same or different times. Co-administration includes simultaneous administration in separate compositions, administration at different times in separate compositions, or administration in a composition in which both agents are present. Co-administration can include simultaneous administration of the agents in separate compositions, administration at different times in separate compositions, and/or administration in a single composition comprising each of the agents to be co-administered.

The term "effective amount" or "therapeutically effective amount" refers to that amount of a compound described herein that is sufficient to effect the intended application including but not limited to disease treatment, as defined below. The therapeutically effective amount may vary depending upon the intended application (in vitro or in vivo), or the subject and disease condition being treated, e.g., the weight and age of the subject, the severity of the disease condition, the manner of administration and the like, which can readily be determined by one of ordinary skill in the art. The term also applies to a dose that will induce a particular response in target cells, e.g., reduction of proliferation or down regulation of activity of a target protein. The specific dose will vary depending on the particular compounds chosen, the dosing regimen to be followed, whether it is administered in combination with other compounds, timing of administration, the tissue to which it is administered, and the physical delivery system in which it is carried.

The term "energy metabolism," as used herein, refers to the transformation of energy that accompanies biochemical reactions in the body, including cellular metabolism and mitochondrial biogenesis. Energy metabolism can be quantified using the various measurements described herein, for example and without limitations, weight-loss, fat-loss, insulin sensitivity, fatty acid oxidation, glucose utilization, triglyceride content, Sirt 1 expression level, AMPK expression level, oxidative stress, and mitochondrial biomass.

The term "isolated", as applied to the subject components, for example a PDE 5 inhibitor, including but not limited to sildenafil and icariin, leucine and leucine metabolites (such as HMB), and resveratrol, refers to a preparation of the substance devoid of at least some of the other components that may also be present where the substance or a similar substance naturally occurs or is initially obtained from. Thus, for example, an isolated substance may be prepared by using a purification technique to enrich it from a source mixture. Enrichment can be measured on an absolute basis, such as weight per volume of solution, or it can be measured in relation to a second, potentially interfering substance present in the source mixture. Increasing enrichment of the embodiments of this invention are increasingly more preferred. Thus, for example, a 2-fold enrichment is preferred, 10-fold enrichment is more preferred, 100-fold enrichment is more preferred, 1000-fold enrichment is even more preferred. A substance can also be provided in an isolated state by a process of artificial assembly, such as by chemical synthesis.

A "modulator" of a pathway refers to a substance or agent which modulates the activity of one or more cellular proteins mapped to the same specific signal transduction pathway. A modulator may augment or suppress the activity and/or expression level or pattern of a signaling molecule. A modulator can activate a component in a pathway by directly binding to the component. A modulator can also indirectly activate a component in a pathway by interacting with one or more associated components. The output of the pathway can be measured in terms of the expression or activity level of proteins. The expression level of a protein in a pathway can be reflected by levels of corresponding mRNA or related transcription factors as well as the level of the protein in a subcellular location. For instance, certain proteins are activated by translocating in or out of a specific subcellular component, including but not limited to nucleus, mitochondria, endosome, lysosome or other membranous structure of a cell. The output of the pathway can also be measured in terms of physiological effects, such as mitochondrial biogenesis, fatty acid oxidation, or glucose uptake.

An "activator" refers to a modulator that influences a pathway in a manner that increases the pathway output. Activation of a particular target may be direct (e.g. by interaction with the target) or indirect (e.g. by interaction with a protein upstream of the target in a signaling pathway including the target).

The term "selective inhibition" or "selectively inhibit" as referred to a biologically active agent refers to the agent's ability to preferentially reduce the target signaling activity as compared to off-target signaling activity, via direct or interact interaction with the target.

The term "substantially free", as used herein, refers to compositions that have less than about 10%, less than about 5%, less than about 1%, less than about 0.5%, less than 0.1% or even less of a specified component. For example a composition that is substantially free of non-branched chain amino acids may have less than about 1% of the non-branched chain amino acid lysine. For example, substantially free of a non-branched chain amino acid can be evidenced by less than 1% of the non-branched chain amino acid when compared to the rest of the amino acids in a given composition.

A "sub-therapeutic amount" of an agent, an activator or a therapy is an amount less than the effective amount for that agent, activator or therapy, but when combined with an effective or sub-therapeutic amount of another agent or therapy can produce a desired result, due to, for example, synergy in the resulting efficacious effects, and/or reduced side effects. A sub-therapeutic amount of the agent or component can be such that it is an amount below which would be considered therapeutic. For example, FDA guidelines can suggest a specified level of dosing to treat a particular condition, and a sub-therapeutic amount would be any level that is below the FDA suggested dosing level. The sub-therapeutic amount can be about 1, 5, 10, 15, 20, 25, 30, 35, 50, 75, 90, or 95% less than the amount that is considered to be a therapeutic amount. The therapeutic amount can be assessed for individual subjects, or for groups of subjects. The group of subjects can be all potential subjects, or subjects having a particular characteristic such as age, weight, race, gender, or physical activity level.

A "synergistic" or "synergizing" effect can be such that the one or more effects of the combination compositions are greater than the one or more effects of each component alone at a comparable dosing level, or they can be greater than the predicted sum of the effects of all of the components at a comparable dosing level, assuming that each component acts independently. The synergistic effect can be about, or greater than about 10, 20, 30, 50, 75, 100, 110, 120, 150, 200, 250, 350, or 500% or even more than the effect on a subject with one of the components alone, or the additive effects as measured when each of the components when administered individually. The effect can be any of the measurable effects described herein.

The terms "free amino acid form" or "individual amino acid form", as used herein, can refer to amino acids that are not bound to other amino acids, for example, by peptide bonds. For example, "free" or "individual" leucine refers to leucine not bound to other amino acids by peptide bonds.

As described herein, a "biological marker", or a "biomarker", generally refers to a measurable indicator of some biological state or condition. Biological markers are often measured and evaluated to examine normal biological processes, pathogenic processes, or pharmacologic responses to a therapeutic intervention. Accordingly, the biomarkers can relate to genes, mRNAs, and proteins corresponding to the biomarkers as described herein.

The invention provides methods, compositions, and kits for reducing or preventing NASH or hepatic steatosis in a subject in need thereof. In some embodiments, the invention provides a method of reducing NASH or hepatic steatosis in a subject in need thereof, comprising administering to the subject a composition comprising an amount of a sirtuin pathway activator such as, e.g., metformin. Another exemplary method of reducing or preventing NASH or hepatic steatosis comprises administering (a) an amount of a branched chain amino acid and/or metabolite thereof existing in form of a free amino acid, and (b) an additional agent.

In some embodiments, the branched chain amino acid and/or metabolite thereof is leucine. In some embodiments, the additional agent is one or more sirtuin pathway activators. In some embodiments, the additional agent is metformin, and/or a PDE inhibitor, e.g. sildenafil. In some embodiments, co-administration of such the branched chain amino acid and/or metabolite thereof and the additional agent reduces or prevents hepatic steatosis to a greater extent than administration of any one of the agents alone. In some embodiments, co-administration of the branched chain amino acid in free amino acid form (or metabolite thereof) and the additional agent has a synergistic effect, e.g., reduces or prevents hepatic steatosis to a greater extent than an additive effect of administering the branched chain amino acid in free amino acid form (or metabolite thereof) alone and administering the additional agent alone.

The invention described herein provides methods for sustaining a reduction of non-alcoholic steatohepatitis (NASH) in a subject in need thereof. In some cases, the disclosed invention also provides methods for reducing liver fibrosis, reducing macrophage infiltration, reducing expression of lipogenic genes, reducing expression of hepatic inflammatory genes, and/or increasing expression of liver fatty acid oxidation genes. The effectiveness of reduction of non-alcoholic steatohepatitis or hepatic steatosis can be ascertained by measuring and monitoring a level of one or more biomarkers or physiological indicators in the subject. The effectiveness of treatment using the disclosed invention can be assessed in various ways. For example, measuring, monitoring and comparing expression levels of biomarkers indicative of liver inflammation genes, macrophage infiltration makers, liver fatty acid oxidation genes, and/or lipogenic genes in the subject prior to, during and after said treatment, each of which is discussed in detail herein. In some embodiments, a reduction of a physiological indicator or a biomarker indicates a sustained reduction of non-alcoholic steatohepatitis (NASH) in the subject after commencement of said methods and compositions described herein.

Reduction and sustained reduction of non-alcoholic steatohepatitis (NASH) can be ascertained by assessing NALFD, NASH and/or hepatic steatosis in a subject. In one aspect, assessment of NALFD, NASH and/or hepatic steatosis in a subject is used to determine if a subject has reduced non-alcoholic steatohepatitis (NASH), and/or to what extent NALFD, NASH and/or hepatic steatosis is prevented or reduced in a subject. In some embodiments, reduction of one or more biomarkers or physiological indicators described herein indicates a sustained reduction of non-alcoholic steatohepatitis (NASH). In some embodiments, assessment of NALFD, NASH and/or hepatic steatosis in a subject is used to determine if a subject is in need of reduction of NAFLD, NASH and/or hepatic steatosis.

Assessment of NAFLD, NASH and Hepatic Steatosis

NALFD, NASH and/or hepatic steatosis can be assessed by any means known to those of skill in the art or otherwise described herein. In some embodiments, reduction of NALFD, NASH and/or hepatic steatosis by assessing a change of one or more physiological indicators. Non-limiting physiological indicator can include a change of liver morphology, liver stiffness, accumulation of fat in the liver, and size or weight of the liver. Non-alcoholic steatohepatitis (NASH) or hepatic steatosis in a subject can be evidenced, e.g., by an accumulation of fat in the liver of the subject (e.g., by an accumulation of fat in hepatic cells of the subject). Accumulation of fat in the liver can be indicated by several means, for example, by ultrasonography, computed tomography (CT), and magnetic resonance imaging, measurement of liver size or weight, or biopsy. For example, a subject with NASH or hepatic steatosis can exhibit a hepatic fat content of 5% or higher, a hepatic fat content of 10% or higher, a hepatic fat content of 20% or higher, a hepatic fat content of 30% or higher, a hepatic fat content of 40% or higher, a hepatic fat content of 50% or higher, a hepatic fat content of 60% or higher, or a hepatic fat content of 70% or higher. In general, a subject with stage 1 hepatic steatosis typically exhibit 5%-33% fat accumulation in liver. A subject with stage 2 hepatic steatosis can exhibit 33%-66% fat accumulation in liver. A subject with stage 3 hepatic steatosis can exhibit over 66% fat accumulation in liver.

Techniques used for assessing hepatic steatosis (including those described herein) can be used in conjunction with measurements of alcohol consumption to assess NAFLD. In some embodiments, NAFLD is assessed by determination of an average daily amount of alcohol consumption by the subject. In some cases, a subject with NAFLD has hepatic steatosis and is assessed by determination of an average of less than 20 grams of alcohol consumption per day (e.g., an average of less than 25 ml alcohol/day). NAFLD in a subject may progress to non-alcoholic steatohepatitis (NASH).

Techniques used for assessing NALFD in conjunction with measurements of liver inflammation can be used to assess NASH. In some embodiments, NASH is assessed by determination of inflammation in the liver of a subject concurrent with hepatic steatosis, for example, upon detection of hepatic fat accumulation (steatosis) and one or more of the following liver conditions: inflammation, ballooning degeneration of hepatocytes (sometimes with identifiable Mallory bodies), glycogenated hepatocyte nuclei, and pericellular fibrosis. Pericellular fibrosis can be identified by trichome strain. Pericellular fibrosis can exhibit upon trichrome staining, for example, a characteristic "chicken wire" pattern. NASH in a subject may progress to cirrhosis.

A subject with NASH or hepatic steatosis can be suffering from a symptom of NASH or hepatic steatosis. Exemplary symptoms include, but are not limited to fatigue, malaise, unexplained weight loss, weakness, lack of appetite, nausea, appearance of small, red spider veins under the skin, easy bruising, jaundice, internal bleeding (e.g., bleeding from engorged veins in the esophagus or intestines), loss of sex drive, ascites, itching, edema, mental confusion, and pain or ache (e.g., pain or ache of the upper right abdomen). In some embodiments, the subject is asymptomatic.

Reduction and sustained reduction of NASH can be assessed by any ultrasonography methods known to those of skill in the art or otherwise described herein. Ultrasonography assessment of NASH and/or hepatic steatosis (e.g., fat accumulation in liver) can comprise use of conventional B-mode ultrasonography. Assessment of various hepatic ultrasonography parameters can be used for the assessment of hepatic steatosis. Exemplary ultrasonography parameters for the assessment of NASH and/or hepatic steatosis include, but are not limited to (1) parenchymal brightness, (2) liver-to-kidney contrast, (3) deep beam attenuation, (4) bright vessel walls, and (5) gallbladder wall definition. Assessment of such ultrasonography parameters can be used to calculate an ultrasonographic steatosis score (USS). USS can be calculated, e.g., as follows: absent (score 0) steatosis was defined as normal liver echotexture; mild (score 1) steatosis as slight and diffuse increase in fine parenchymal echoes with normal visualization of diaphragm and portal vein borders; moderate (score 2) steatosis as moderate and diffuse increase in fine echoes with slightly impaired visualization of portal vein borders and diaphragm; and severe (score 3) steatosis as fine echoes with poor or no visualization of portal vein borders, diaphragm, and posterior portion of the right lobe.

Reduction and sustained reduction of NASH can be assessed by any computed tomography (CT) known to those of skill in the art or otherwise described herein. CT images can be assessed by, e.g., a radiologist. CT images of the liver of a subject can be assessed by, e.g., measuring density of regions of interest in the images. Regions of interest within images can be selected so as not to contain blood vessels or other artifacts (e.g., motion artifacts). Density of regions of interest in a CT image can be measured in Hounsfield units (HU). Normal liver tissue can have a HU measurement of 40-60 HU. By contrast, fat typically has a lower density. For example, fat can have an HU measurement of, e.g., about −100 to about −500. NASH or hepatic steatosis can be evidenced by an HU measurement less than 40 HU. NASH or hepatic steatosis can be evidenced by an HU measurement that is between −500 and 40 HU, for example, an HU measurement that is −500-1 HU, −100-10 HU, 0-20 HU, 5-30 HU, or 20-39.9 HU. NASH or hepatic steatosis can be assessed by a subject exhibiting an HU measurement of 39, 38, 37, 36, 35, 34, 33, 32, 31, 30, 29, 28, 27, 26, 25, 24, 23, 22, 21, 20, 19, 18, 17, 16, 15, 14, 13, 12, 11, 10, 9, 8, 7, 6, 5, 4, 3, 2, 1, 0, or less than 0 HU. NASH or hepatic steatosis can be evidenced by a difference in HU measurement between spleen and liver (e.g., $HU_{spleen}-HU_{liver}$) For example, hepatic steatosis can be evidenced if $HU_{spleen}-HU_{liver}$ is greater than 0, for example, if $HU_{spleen}-HU_{liver}$ is between 1-10, 10-20, or more than 20. In some embodiments, a difference in HU measurement between spleen and liver of 18.5 is used to determine NASH or hepatic steatosis in a subject. In some embodiments, a reduction of difference in $HU_{spleen}-HU_{liver}$ indicates a sustained reduction of NASH or hepatic steatosis.

Reduction and sustained reduction of NASH can be assessed by any MRI methods known to those of skill in the art or otherwise described herein. Exemplary methods of using MRI to determine steatosis, e.g., hepatic steatosis, are described in US Patent Application Pub. No. 20050215882, which is hereby incorporated by reference.

Reduction and sustained reduction of NASH or hepatic steatosis can be evidenced by measurement of liver weight and/or size. Methods of measuring liver weight and/or size can be any known to those of skill in the art or otherwise described herein. Reduction of NASH or hepatic steatosis can be indicated by a decrease in liver weight and/or size as compared to the subject before commencement of methods and compositions described herein, or to a control subject with NASH or hepatic steatosis. In some embodiments, a decrease in liver weight/size by 10% or more, 15% or more, 20%, or more, 25% or more, 30%, or more, 35% or more, 40% or more, 45% or more, 50%, or more, 55% or more, 60%, or more, 65% or more, 70% or more, 75% or more, 80% or more, 85% or more, 90%, or more, 95% or more, 100%, or more than 100% as compared to the subject before commencement of methods and compositions described herein, or to a control subject with NASH or hepatic steatosis can indicate sustained reduction of NASH or hepatic steatosis in a subject.

Reduction and sustained reduction of NASH or hepatic steatosis can be evidenced by tissue biopsy. A liver biopsy sample can be obtained by any means known to those of skill in the art, for example, by needle biopsy. The sample can be processed by any means known to those of skill in the art or otherwise described herein. The sample can be fixed (e.g., with formalin) or may be unfixed. The sample may be snap-frozen. For example, the sample may be sectioned into thin sections. The sections may be stained, e.g., with hematoxylin and eosin. Accumulation of fat in the liver can be evidenced by appearance of vacuoles which are filled with lipids such as, by way of example only, triglycerides. Such vacuoles can be appear to be optically "empty", since fats can dissolve during histological tissue processing. Accordingly, levels of NASH or hepatic steatosis can be determined by measuring the number, size, or density of hepatic lipid vacuoles.

Liver stiffness can be evaluated by performing Transient Elastography (TE) (Fibroscan®, Echosens®, Paris, France). TE (Fibroscan®, Echosens®, Paris, France) is probably one of the most widely used noninvasive method detecting liver disease. TE is painless and can provide results in as less than 5 minutes and is highly acceptable for patients. The volume of liver tissue evaluated by TE approximates a cylinder 4×1 cm which is usually at least 100 times bigger than a liver biopsy. In general, vibrations of mild amplitude and low frequency are transmitted by the transducer inducing an elastic shear wave that propagates within the liver. Pulse-echo ultrasonic acquisitions are performed to follow the shear wave and measure its speed, which is directly related to the tissue stiffness (the harder the tissue, the faster the shear propagates). Results are usually expressed in Kilopascals (Kpa) and correspond to the median value of ten validated measurements ranging from 2.5 to 75 Kpa, with 5.5 Kpa reported to define normality.

Levels of reduction and sustained reduction of NASH or hepatic steatosis can be determined using any of the assessment methods described herein. Levels of reduction and sustained reduction of NASH or hepatic steatosis can be quantified, by way of non-limiting example only, as a percentage of fat accumulation (e.g., fat content) in the liver. In some embodiments, NASH or hepatic steatosis is scored according to a 0-3 score, with 0=<5% fat accumulation in the liver, 1=5%-33% fat accumulation in the liver, 2=33%-66% fat accumulation in the liver, and 3=>66% fat accumulation in the liver. Liver fat content can be assessed by any means known to those of skill in the art, including, e.g., by proton magnetic resonance spectroscopy, by biopsy, or by any other methods described herein.

In one aspect, reduction and sustained reduction of NASH or hepatic steatosis can be evaluated by measuring one or more biomarkers selected from the group consisting of transforming growth factor (TGF)-β, cytokeratin 18, serum aspartate transaminase (AST), serum alanine transaminase (ALT), and gamma glutamyl transferase (GGT). Methods of measuring biomarkers can be any known to those of skill in the art or otherwise described herein. Reduction and sustained reduction of NASH or hepatic steatosis can be indicated by a decrease of expression level of one or more biomarkers as compared to the subject before commencement of methods and compositions described herein, or to a control subject with NASH or hepatic steatosis. In some cases, reduction and sustained reduction of NASH or hepatic steatosis is indicated by a aspartate transaminase to alanine transaminase ratio that is greater than at least 1, at least 2, at least 3, at least 4, at least 5, at least 10, or more.

Levels of liver inflammation, indicative of hepatic steatosis and/or NASH, can be determined using any of the assessment methods described herein. Levels of liver inflammation can be quantified, by way of non-limiting example only, as a percentage, a fold change or a ratio, of biomarkers such as expression level of liver inflammation biomarkers in the liver. Expression of a biomarker can be achieved by way of measuring, quantifying, and monitoring the expression level of the gene or mRNA encoding said biomarker, and/or the peptide, or protein of said biomarker. In general, assessment of biomarker expression can be achieved by way of measuring, quantifying, monitoring or comparing results prior to, during and after treatment. Exemplary of biomarkers indicative of liver inflammation include, but are not limited to, interleukin-(IL) 6, interleukin-(IL) 1β, tumor necrosis factor (TNF)-α, transforming growth factor (TGF)-β, monocyte chemotactic protein (MCP)-1, C-reactive protein (CRP), PAI-1, collagen isoforms such as Col1a1, Col1a2, and Col4a1. Liver inflammation can also be assessed by change of macrophage infiltration, For example, measuring a change of CD68 expression level. In some cases, liver inflammation can be assessed by examining liver fibrosis and using liver picrosirius red staining. In some cases, liver inflammation can be assessed by measuring or monitoring serum levels or circulating levels of interleukin-(IL) 6, interleukin-(IL) 1β, tumor necrosis factor (TNF)-α, transforming growth factor (TGF)-β, monocyte chemotactic protein (MCP)-1, and C-reactive protein (CRP).

Levels of liver fat content can be determined using any of the assessment methods described herein. Levels of liver fat content can be quantified, by way of non-limiting example only, as a percentage, a fold change or a ratio, of liver lipogenic gene expression in the liver. In general, assessment of gene expression can be achieved by way of measuring, quantifying, monitoring or comparing results prior to, during and after treatment. Exemplary of biomarkers indicative of liver fat content include, but are not limited to, acetyl-CoA carboxylase (ACC), stearoyl-CoA desaturase 1 (SCD1), fatty acid synthase (FAS), and liver fatty oxidation genes such as PPAR-α, ACOX1, COX1, and CPT1B.

Level of reduction of biomarkers using the methods and composition described herein can indicate a sustained reduction of NASH or hepatic steatosis. In some embodiments, a decrease in biomarker expression by 10% or more, 15% or more, 20%, or more, 25% or more, 30%, or more, 35% or more, 40% or more, 45% or more, 50%, or more, 55% or more, 60%, or more, 65% or more, 70% or more, 75% or more, 80% or more, 85% or more, 90%, or more, 95% or more, 100%, or more than 100% as compared to the subject before commencement of methods and compositions described herein, or to a control subject with NASH or hepatic steatosis can indicate sustained reduction of NASH or hepatic steatosis in a subject.

In some embodiments, the reduction of one or more biomarkers or physiological indicators is monitored for a period time before, during or after commencement of the methods and compositions described herein. The biomarker expression can be measured and monitored for at least 1 week, at least 2 weeks, at least 3 weeks, at least 4 weeks, at least 5 weeks, at least 6 weeks, at least 7 weeks, at least 8 weeks, at least 9 weeks, at least 10 weeks, at least 11 weeks, at least 12 weeks, at least 1 month, at least 2 months, at least 3 months, at least 4 months, at least 5 months, at least 6 months, at least 7 months, at least 8 months, at least 9 months, at least 10 months, at least 11 months, at least 12 months, at least 2 years, at least 5 years, at least 10 years, or more. In some embodiments, the sustained reduction of one or more biomarkers or physiological indicators is monitored periodically before, during or after commencement of the methods or compositions described herein. The biomarker expression can be measured and monitored for every week, every 2 weeks, every 3 weeks, every 4 weeks, every 5 weeks, every 6 weeks, every 7 weeks, every 8 weeks, every 9 weeks, every 10 weeks, every 11 weeks, every 12 weeks, every month, every 2 months, every 3 months, every 4 months, every 5 months, every 6 months, every 7 months, every 8 months, every 9 months, every 10 months, every 11 months, every 12 months, every 2 years, every 5 years, every 10 years, or more.

Administration and/or co-administration of any of the compounds described herein can reduce NASH or hepatic steatosis in a subject in need thereof. Exemplary subjects in need of NASH or hepatic steatosis reduction can include subjects who have NASH or hepatic steatosis.

Reduction of NASH or hepatic steatosis can be determined by comparison to the subject before commencement of the methods and compositions described herein, or to a control subject and/or control population. Reduction of NASH or hepatic steatosis in a subject can be considered if any one or more of hepatic fat content, as measured by any of the methods described herein, liver size or weight, liver vacuole number, size of a liver vacuole, liver vacuole density, expression of biomarkers such as, interleukin-(IL) 6, interleukin-(IL) 1β, tumor necrosis factor (TNF)-α, transforming growth factor (TGF)-β, monocyte chemotactic protein (MCP)-1, C-reactive protein (CRP), PAI-1, Col1a1, Col1a2, Col4a1, CD68, acetyl-CoA carboxylase (ACC), stearoyl-CoA desaturase 1 (SCD1), fatty acid synthase (FAS), PPAR-α, ACOX1, COX1, CPT1B, cytokeratin 18, gamma glutamyl transferase (GGT), serum alanine transaminase (ALT) and/or serum aspartate transaminase levels in the subject are reduced as compared to a control subject and/or control population. A control subject can be an individual that has not been administered one or more compounds described herein. Likewise, a control population can encompass a plurality of individuals that have not been administered one or more compounds described herein. The control subject can be a subject having hepatic steatosis, that is not administered one or more compounds described herein. The control subject can be a different subject.

It is not necessary for the control subject to be a different individual from said subject. For example, the control subject can be the same subject at an earlier time point, for example, prior to receiving a first dose of any of the compounds described herein. In some embodiments, a level of hepatic steatosis in the subject following administration of one or more compounds described herein is compared to a level of hepatic steatosis in the subject prior to first administration of the one or more compounds.

An exemplary method of assessing NASH or hepatic steatosis reduction in a subject can comprise measuring a level of NASH hepatic steatosis in the subject or in a biological sample derived from the subject at a first time point. The first time point may be a time point prior to administration of one or more compounds described herein. The method may further comprise measuring a level of NASH or hepatic steatosis in the subject or in a biological sample derived from the subject at a second time point. The second time point may follow administration of the one or more compounds described herein. The level measured at the second time point may be compared to the level measured at the first time point to determine whether reduction has occurred. Reduction of NASH hepatic steatosis can indicate clinical efficacy of the administration of the one or more compounds described herein. Reduction of NASH hepatic steatosis can indicate a sustained reduction of NASH or hepatitis steatosis. The method may further comprise administering additional doses of the one or more compounds described herein if the level of NASH or hepatic steatosis in the subject is reduced.

Practice of any one of the methods of the invention can reduce NASH or hepatic steatosis by at least 5%, 10%, 15%, 20%, 25%, 30%, 35%, 40%, 45%, 50%, 55%, 60%, 65%, 70%, 75%, 80%, 85%, 90%, 95%, 96%, 97%, 98%, 99%, or more than 99%. For example, practice of any one of the methods of the invention can reduce NASH or hepatic steatosis by 5-20%, 10-40%, 30-60%, 40-80%, 60-95%, or 75-99%. In some embodiments, administration of any combination of agents described herein reduces NASH or hepatic steatosis in about 1 week, 2 weeks, 3 weeks, 4 weeks, 5 weeks, 6 weeks, 8 weeks, or less. Administration of any combination of agents described herein can, for example, reduce liver weight by at least 10% in about 1 week, 2 weeks, 3 weeks, 4 weeks, 5 weeks, 6 weeks, 8 weeks, or less. In some cases, administration of any combination of agents described herein can, for example, reduce liver weight by at least 20% in about six weeks. Administration of any combination of agents described herein can, by way of example only, reduce liver vacuole number, size, and/or density by over 10%, 20%, 25%, over 50%, over 75%, or over 90% in about 1 week, 2 weeks, 3 weeks, 4 weeks, 5 weeks, 6 weeks, 8 weeks, or less.

Practice of any one of the methods of the invention can sustain reduction of NASH or hepatic steatosis by at least 5%, 10%, 15%, 20%, 25%, 30%, 35%, 40%, 45%, 50%, 55%, 60%, 65%, 70%, 75%, 80%, 85%, 90%, 95%, 96%, 97%, 98%, 99%, or more than 99%. For example, practice of any one of the methods of the invention can sustain reduction of NASH or hepatic steatosis by 5-20%, 10-40%, 30-60%, 40-80%, 60-95%, or 75-99%. In some embodiments, administration of any combination of agents described herein sustains reduction of NASH or hepatic steatosis in about 1 week, 2 weeks, 3 weeks, 4 weeks, 5 weeks, 6 weeks, 8 weeks, or less. Administration of any combination of agents described herein can, for example, sustain reduction of liver weight by at least 10% in about 1 week, 2 weeks, 3 weeks, 4 weeks, 5 weeks, 6 weeks, 8 weeks, or less. In some cases, administration of any combination of agents described herein can, for example, sustain reduction of liver weight by at least 20% in about six weeks. Administration of any combination of agents described herein can, by way of example only, sustain reduction of liver vacuole number, size, and/or density by over 10%, 20%, 25%, over 50%, over 75%, or over 90% in about 1 week, 2 weeks, 3 weeks, 4 weeks, 5 weeks, 6 weeks, 8 weeks, or less.

Practice of any one of the methods of the invention can reduce liver inflammation by at least 5%, 10%, 15%, 20%, 25%, 30%, 35%, 40%, 45%, 50%, 55%, 60%, 65%, 70%, 75%, 80%, 85%, 90%, 95%, 96%, 97%, 98%, 99%, or more than 99%. For example, practice of any one of the methods of the invention can reduce liver inflammation by 5-20%, 10-40%, 30-60%, 40-80%, 60-95%, or 75-99%. In some embodiments, administration of any combination of agents described herein reduces liver inflammation in about 1 week, 2 weeks, 3 weeks, 4 weeks, 5 weeks, 6 weeks, 8 weeks, or less. Administration of any combination of agents described herein can, for example, reduce macrophage infiltration by at least 10% in about six weeks. Administration of any combination of agents described herein can, for example, reduce macrophage infiltration by at least 20% in about six weeks. Administration of any combination of agents described herein can, by way of example only, reduce liver inflammation, macrophage infiltration, and/or liver fibrosis, by number, size or density by over 25%, over 50%, over 75%, or over 90% in about six weeks.

Practice of any one of the methods of the invention can sustain reduction of liver inflammation by at least 5%, 10%, 15%, 20%, 25%, 30%, 35%, 40%, 45%, 50%, 55%, 60%, 65%, 70%, 75%, 80%, 85%, 90%, 95%, 96%, 97%, 98%, 99%, or more than 99%. For example, practice of any one of the methods of the invention can sustain reduction of liver inflammation by 5-20%, 10-40%, 30-60%, 40-80%, 60-95%, or 75-99%. In some embodiments, administration of any combination of agents described herein sustains reduction of liver inflammation in about 1 week, 2 weeks, 3 weeks, 4 weeks, 5 weeks, 6 weeks, 8 weeks, or less. Administration of any combination of agents described herein can, for example, sustain reduction of macrophage infiltration by at least 10% in about six weeks. Administration of any combination of agents described herein can, for example, sustain reduction of macrophage infiltration by at least 20% in about six weeks. Administration of any combination of agents described herein can, by way of example only, sustain reduction of liver inflammation, macrophage infiltration, and/or liver fibrosis, by number, size or density by over 25%, over 50%, over 75%, or over 90% in about six weeks.

Practice of any one of the methods of the invention can reduce liver fat content by at least 5%, 10%, 15%, 20%, 25%, 30%, 35%, 40%, 45%, 50%, 55%, 60%, 65%, 70%, 75%, 80%, 85%, 90%, 95%, 96%, 97%, 98%, 99%, or more than 99%. For example, practice of any one of the methods of the invention can reduce liver fat content by 5-20%, 10-40%, 30-60%, 40-80%, 60-95%, or 75-99%. In some embodiments, administration of any combination of agents described herein reduces liver fat content in about 1 week, 2 weeks, 3 weeks, 4 weeks, 5 weeks, 6 weeks, 8 weeks, or less. Administration of any combination of agents described herein can, for example, reduce lipogenic gene expression by at least 10% in about six weeks. Administration of any combination of agents described herein can, for example, reduce lipogenic gene expression by at least 20% in about six weeks. Administration of any combination of agents described herein can, by way of example only, reduce liver fat content, and/or increase liver fatty acid oxidation, by number, size or density by over 25%, over 50%, over 75%, or over 90% in about six weeks.

Practice of any one of the methods of the invention can sustain reduction of liver fat content by at least 5%, 10%, 15%, 20%, 25%, 30%, 35%, 40%, 45%, 50%, 55%, 60%, 65%, 70%, 75%, 80%, 85%, 90%, 95%, 96%, 97%, 98%, 99%, or more than 99%. For example, practice of any one of the methods of the invention can sustain reduction of liver fat content by 5-20%, 10-40%, 30-60%, 40-80%, 60-95%, or 75-99%. In some embodiments, administration of any combination of agents described herein sustains reduction of liver fat content in about 1 week, 2 weeks, 3 weeks, 4 weeks, 5 weeks, 6 weeks, 8 weeks, or less. Administration of any combination of agents described herein can, for example, sustain reduction of lipogenic gene expression by at least 10% in about six weeks. Administration of any combination of agents described herein can, for example, sustain reduction of lipogenic gene expression by at least 20% in about six weeks. Administration of any combination of agents described herein can, by way of example only, sustain reduction of liver fat content, and/or increase liver fatty acid oxidation, by number, size or density by over 25%, over 50%, over 75%, or over 90% in about six weeks.

In some cases, the effectiveness of reducing NASH, reducing hepatic steatosis, reducing liver fibrosis, reducing macrophage infiltration, reducing expression of lipogenic genes, reducing expression of hepatic inflammatory genes, and increasing expression of liver fatty acid oxidation genes by practice of any one of the methods of the invention can be maintained for at least 1 week, at least 2 weeks, at least 3 weeks, at least 4 weeks, at least 5 weeks, at least 6 weeks, 8 weeks, at least 8 weeks, at least 12 weeks, or more. In some cases, the effectiveness can be maintained for at least 1 month, at least 2 months, at least 3 months, at least 4 months, at least 5 months, at least 6 months, at least 12 months, at least 1 year, at least 2 years, at least 5 years, at least 10 years, or longer. In some cases, the sustainable effect is detectable after administering the composition of the invention for at least 1 dose, at least 2 doses, at least 3 doses, at least 4 doses, at least 5 doses, at least 6 doses, at least 8 doses, at least 10 doses, or more.

In some cases, the effectiveness of sustaining reduction of NASH, sustaining reduction of hepatic steatosis sustaining reduction of liver fibrosis, sustaining reduction of macrophage infiltration, sustaining reduction of expression of lipogenic genes, sustaining reduction of expression of hepatic inflammatory genes, and sustaining reduction of increased expression of liver fatty acid oxidation genes by practice of any one of the methods of the invention can be maintained for at least 1 week, at least 2 weeks, at least 3 weeks, at least 4 weeks, at least 5 weeks, at least 6 weeks, 8 weeks, at least 8 weeks, at least 12 weeks, or more. In some cases, the effectiveness can be maintained for at least 1 month, at least 2 months, at least 3 months, at least 4 months, at least 5 months, at least 6 months, at least 12 months, at least 1 year, at least 2 years, at least 5 years, at least 10 years, or longer. In some cases, the sustainable effect is detectable after administering the composition of the invention for at least 1 dose, at least 2 doses, at least 3 doses, at least 4 doses, at least 5 doses, at least 6 doses, at least 8 doses, at least 10 doses, or more.

Administration and/or co-administration of any of the compounds described herein can prevent NASH or hepatic steatosis in a subject in need thereof. Exemplary subjects in need of hepatic steatosis reduction can include subjects exhibiting a propensity for, or having a high risk of developing, hepatic steatosis.

A number of environmental and genetic risk factors have been found to increase propensity of a subject to develop NASH or hepatic steatosis. A subject can exhibit a propensity for developing NASH or hepatic steatosis if the subject exhibits any combination of risk factors described herein. A greater number of risk factors exhibited by a subject can indicate a higher propensity for developing NASH or hepatic steatosis, as compared to a subject that exhibits a lower number of risk factors. It is understood that a subject can be considered to exhibit a propensity for developing NASH or hepatic steatosis if the subject exhibits even one, two, three, or more of the risk factors described herein.

An exemplary risk factor for developing hepatic steatosis is obesity. Accordingly, a subject can be considered to exhibit an increased propensity to develop NASH or hepatic steatosis if the subject is obese. Obesity in a subject can be assessed using a body mass index (BMI) measurement. A subject's BMI can be calculated by dividing the subject's body weight (in kg) by the square of the subject's height (m2). A subject can be considered obese if the subject exhibits a BMI that is over 25 kg/m2, over 26 kg/m2, over 27 kg/m2, over 28 kg/m2, over 29 kg/m2, over 30 kg/m2, over 31 kg/m2, over 32 kg/m2, over 33 kg/m2, over 34 kg/m2, over 35 kg/m2, over 36 kg/m2, over 37 kg/m2, over 38 kg/m2, over 39 kg/m2, over 40 kg/m2, or over 45 kg/m2. A subject can also be considered to exhibit a propensity to develop NASH or hepatic steatosis if the subject exhibits abdominal obesity. Abdominal obesity can be assessed by measuring the circumference of the subject's waist. For example, if the subject is an adult male, the subject can be considered to exhibit abdominal obesity if the subject exhibits a waist circumference of 102 cm or greater. For other example, if the subject is an adult female, the subject can be considered to exhibit abdominal obesity if the subject exhibits a waist circumference of 88 cm or greater.

Another exemplary risk factor for developing NASH or hepatic steatosis is high blood pressure. Accordingly, a subject can be considered to exhibit an increased propensity to develop NASH or hepatic steatosis if the subject exhibits high blood pressure. Blood pressure in a subject can be assessed by measuring a systolic and/or diastolic blood pressure (bp) in the subject. A subject can be considered to exhibit high blood pressure if the subject exhibits a systolic by that is 120 or higher, 121 or higher, 122 or higher, 123 or higher, 124 or higher, 125 or higher, 126 or higher, 127 or higher, 128 or higher, 129 or higher, 130 or higher, 131 or higher, 132 or higher, 133 or higher, 134 or higher, 135 or higher, 136 or higher, 137 or higher, 138 or higher, 139 or higher, or 140 or higher. A subject can be considered to exhibit high blood pressure if the subject exhibits a diastolic by that is 80 or higher, 81 or higher, 82 or higher, 83 or higher, 84 or higher, 85 or higher, 86 or higher, 87 or higher, 88 or higher, 89 or higher, 90 or higher, 91 or higher, 92 or higher, 93 or higher, 94 or higher, 95 or higher, 96 or higher, 97 or higher, 98 or higher, 99 or higher, or 100 or higher.

Another exemplary risk factor for developing NASH or hepatic steatosis is high cholesterol. Accordingly, a subject can be considered to exhibit an increased propensity to develop NASH or hepatic steatosis if the subject exhibits high cholesterol. Cholesterol in a subject can be assessed by measuring total blood cholesterol levels in the subject. A subject can be considered to exhibit high cholesterol if the subject exhibits, e.g., over 200 mg/dl total blood cholesterol, over 210 mg/dl total blood cholesterol, over 220 mg/dl total blood cholesterol, over 230 mg/dl total blood cholesterol, or over 240 mg/dl total blood cholesterol. A subject can be considered to exhibit high cholesterol if the subject exhibits, 200-220 mg/dl total blood cholesterol, 220-240 mg/dl total blood cholesterol, or 240 mg/dl total blood cholesterol or higher. Cholesterol in a subject can also be assessed by measuring blood low density lipoprotein (LDL) levels in the subject. A subject can be considered to exhibit high cholesterol if the subject exhibits, e.g., 130 mg/dl LDL or higher, 135 mg/dl LDL or higher, 140 mg/dl LDL or higher, 145 mg/dl LDL or higher, 150 mg/dl LDL or higher, 155 mg/dl LDL or higher, 160 mg/dl LDL or higher, 165 mg/dl LDL or higher, 170 mg/dl LDL or higher, 175 mg/dl LDL or higher, 180 mg/dl LDL or higher, 185 mg/dl LDL or higher, or 190 mg/dl LDL or higher. Cholesterol in a subject can also be assessed by measuring blood high density lipoprotein (HDL) levels in the subject. A subject can be considered to exhibit high cholesterol if the subject exhibits, e.g., 60 mg/dl HDL or lower, 55 mg/dl HDL or lower, 50 mg/dl HDL or lower, 45 mg/dl HDL or lower, or 40 mg/dl HDL or lower.

Another exemplary risk factor for developing NASH or hepatic steatosis is insulin resistance. Accordingly, a subject can be considered to exhibit an increased propensity to develop NASH or hepatic steatosis if the subject exhibits insulin resistance. Insulin resistance in a subject can be assessed by any means known in the art or otherwise described herein. By way of example only, insulin resistance may be assessed by measuring Homeostatic Assessment of Insulin Resistance ($HOMA_{IR}$) in the subject. $HOMA_{IR}$ can be determined by any means known in the art, for example, by the following equation: $HOMA_{IR}$=Insulin (uU/mL)× glucose (mM)]/22.5. The $HOMA_{IR}$ value increases with increasing insulin resistance, and values above (2.6) are generally considered to be insulin resistant. A subject can be considered to exhibit insulin resistance if the subject exhibits a $HOMA_{IR}$ above the $75^{th}$ percentile, or a $HOMA_{IR}$ value of over 2.6. Insulin resistance may also be assessed by measuring fasting serum insulin levels in the subject. A subject may be considered to exhibit insulin resistance if the subject exhibits a fasting serum insulin level of 60 pmol/L or higher. Insulin resistance may also be assessed by measuring a quantitative insulin sensitivity check index (QUICKI) in the subject. QUICKI can be determined by the following equation: QUICKI=1/(log(fasting insulin µU/mL)+log(fasting glucose mg/dL)). A subject may be considered to exhibit insulin resistance if the subject exhibits a QUICKI of 0.30 or less. For other example, insulin resistance can be determined by measuring blood glucose levels in a subject, in some cases over a period of time, following administration of a bolus of insulin. Subjects with insulin resistance typically exhibit an attenuated drop in blood glucose levels following insulin administration, as compared to subject without insulin resistance.

Another exemplary risk factor for developing NASH or hepatic steatosis is diabetes. Accordingly, a subject can be considered to exhibit an increased propensity to develop NASH or hepatic steatosis if the subject has or is diagnosed with diabetes. The diabetes can be Type I or Type II diabetes. Diabetes may be diagnosed by any means known to those of skill in the art, or otherwise described herein. For example, a subject may be diagnosed with diabetes if the subject exhibits high fasting plasma glucose levels (e.g., 126 mg/dl or higher). A subject may be diagnosed with diabetes if the subject exhibits high plasma glucose levels following administration of a bolus of glucose (e.g., in a glucose tolerance test). For example, a subject may be diagnosed with diabetes if the subject exhibits 200 mg/dl plasma glucose or higher two hours after administration of a 75 g bolus of glucose.

Genetics may be a risk factor for developing NASH or hepatic steatosis. For example, males of Indian, Asian, and/or Mexican descent may have a higher risk of developing hepatic steatosis. Accordingly, a subject can be considered to exhibit an increased propensity to develop NASH or hepatic steatosis if the subject is a male of African, Asian, and/or Mexican descent. Genetic polymorphisms may also be associated with an increased propensity to develop NASH or hepatic steatosis. For example, a subject may be considered to exhibit an increased propensity to develop NASH or hepatic steatosis if the subject exhibits a T455C or C482T polymorphism in the APOC3 gene.

Certain medications increase risk for developing NASH or hepatic steatosis. Such medications increase risk for developing NASH or hepatic steatosis include, but are not limited to oral corticosteroids (e.g., prednisone, hydrocortisone, among others), synthetic estrogens (e.g., Premarin, Ortho-Est, tamoxifen, among others), amiodarone (Cordarone, Pacerone), diltiazem, anti-retroviral drugs such as, e.g., indinavir, and methotrexate. Accordingly, a subject may be considered to exhibit an increased propensity to develop NASH or hepatic steatosis if the subject has taken any of the medications described herein as increasing risk for developing NASH or hepatic steatosis.

In some embodiments, the subject exhibiting a propensity for developing NASH or hepatic steatosis has not yet developed hepatic steatosis. For example, the subject may not have exhibited a symptom of NASH or hepatic steatosis. For other example, the subject may not exhibit increased fat content of the liver. In some embodiments, the subject has not been diagnosed with NASH or hepatic steatosis. In some embodiments, the subject does not exhibit an increase in serum ALT levels as compared to a control subject without NASH or hepatic steatosis.

Practice of any one of the methods of the invention can prevent or reduce occurrence of NASH or hepatic steatosis in at least 5%, 10%, 15%, 20%, 25%, 30%, 35%, 40%, 45%, 50%, 55%, 60%, 65%, 70%, 75%, 80%, 85%, 90%, 95%, 96%, 97%, 98%, 99%, or more than 99% of treated subjects. For example, practice of any one of the methods of the invention can prevent NASH or hepatic steatosis or reduce occurrence of hepatic steatosis by 5-20%, 10-40%, 30-60%, 40-80%, 60-95%, or 75-99%. In some embodiments, administration of any combination of agents described herein to a subject prevents or reduces occurrence of NASH or hepatic steatosis in the subjects for at least about 1, 2, 3, 4, 5, 6, 7, 8 weeks or 2, 4, 6, 12 or 24 months. Prevention of NASH or hepatic steatosis can be determined by comparison to a reference subject and/or reference population. NASH or hepatic steatosis in a subject can be considered to be prevented or to have reduced occurrence if any one or more of hepatic fat content, as measured by any of the methods described herein, liver size or weight, liver vacuole number, size of a liver vacuole, liver vacuole density, serum alanine transaminase (ALT) and/or aspartate transaminase levels in the subject does not increase or increases to a lesser extent as compared to a reference subject and/or reference population. The reference subject and/or reference population can be another subject or population of subjects exhibiting a comparable propensity for developing NASH or hepatic steatosis who has not developed NASH or hepatic steatosis, and who is not treated with one or more compounds described herein.

Composition

The invention provides a method of reducing NASH or hepatic steatosis in a subject in need thereof, comprising administering to the subject a composition comprising an amount of a sirtuin pathway activator such as, e.g., metformin. Another exemplary method of reducing or preventing NASH or hepatic steatosis comprises administering (a) an amount of a branched chain amino acid and/or metabolite thereof existing in form of a free amino acid, and (b) an additional agent. In some embodiments, the branched chain amino acid and/or metabolite thereof is leucine. In some embodiments, the additional agent is one or more sirtuin pathway activators. In some embodiments, the additional agent is metformin, and/or a PDE inhibitor, e.g. sildenafil. In some embodiments, co-administration of the branched chain amino acid and/or metabolite thereof and the additional agent reduces or prevents NASH or hepatic steatosis to a greater extent than administration of any one of the agents alone. In some embodiments, co-administration of the branched chain amino acid in free amino acid form (or metabolite thereof) and the additional agent has a synergistic effect, e.g., reduces or prevents NASH or hepatic steatosis to a greater extent than an additive effect of administering the branched chain amino acid in free amino acid form (or metabolite thereof) alone and administering the additional agent alone.

In some embodiments, the composition is formulated in tablet or capsules for administration to a subject in need thereof. The subject may have NASH or hepatic steatosis. In some cases, the subject is diagnosed with NASH or hepatic steatosis, NAFLD or NASH-related cirrhosis. In some cases, the subject exhibits a propensity for having NASH or hepatic steatosis, NAFLD or NASH-related cirrhosis. The composition can be formulated for oral administration. The composition can comprise at least one tablet or capsule. The composition can comprise at least two tablets or capsules. In some embodiments, the composition comprises three tablets or capsules, four tablets or capsules, five tablets or capsules, or more. In some embodiments, the composition is administered at least once a day, twice a day, three times a day, or more. The tablets or capsules in a composition can comprise the same amount or different amount of each of the component. As a non-limiting example, the composition can comprise the same amount or different amount of leucine in the form of a free amino acid or metabolite thereof. As another example, the composition can comprise the same amount or different amount of a sirtuin pathway activator such as metformin. As another example, the composition can comprise the same amount or different amount of a PDE5 inhibitor such as sildenafil.

In some embodiments, a tablet or capsule of the composition described herein comprises leucine in the form of a free amino acid or metabolite. In some embodiments, a tablet or capsule of the composition comprises leucine or metabolite thereof and metformin. In some, a tablet or capsule of the composition comprises leucine in the form of a free amino acid or metabolite thereof, metformin and sildenafil. In some embodiments, a tablet or capsule of the composition comprises metformin and sildenafil.

In some embodiments, a composition described herein comprises (a) an amount of leucine in the form of a free amino acid or metabolite thereof, and (b) an amount of sildenafil. In certain embodiments, the amount of in the form of a free amino acid or metabolite thereof administered in a tablet or capsule that does not contain sildenafil. In some embodiments, the composition further comprises a third component, (c) an amount of metformin. In certain embodiments, the amount of leucine in the form of a free amino acid or metabolite thereof is between about 50-95 wt % of a total wt of (a), (b) and (c), the amount of metformin, excluding fillers, is between about 5-50 wt % of a total wt of (a), (b), and (c), and the amount of sildenafil, excluding fillers, is between about 0.01-1 wt % of a total wt of (a), (b), and (c). In certain embodiments, a wt % of said leucine in the form of a free amino acid and/or a metabolite thereof in said pharmaceutical composition, excluding fillers, is about 50-95 wt %. In certain embodiments, a wt % of said metformin in said pharmaceutical composition, excluding fillers, is about 5-50 wt %. In certain embodiments, a wt % of said sildenafil in said pharmaceutical composition, excluding fillers, is about 0.01-1 wt %.

Exemplary Compounds

The invention provides compounds for the reduction, the sustained reduction of, and/or prevention of NAFLD, NASH and/or hepatic steatosis. For example, co-administration of a branched chain amino acid in free amino acid form or metabolite thereof, and an additional agent can reduce and/or prevent NAFLD, NASH and/or hepatic steatosis in a subject. The additional agent can be a sirtuin pathway activator and/or a PDE inhibitor, such as a PDE5 inhibitor.

Branched Chain Amino Acids

Branched chain amino acids may have aliphatic side chains with a branch carbon atom that is bound to two or more other atoms. The other atoms may be carbon atoms. Examples of branched chain amino acids include leucine, isoleucine, and valine. Branched chain amino acids may also include other compounds, such as 4-hydroxyisoleucine. Such branched chain amino acids may be administered to a subject in free amino acid form. In some embodiments, the branched chain amino acid in free amino acid form is leucine in free amino acid form. In some embodiments, a composition comprising a branched chain amino acid in free amino acid form is substantially free of one or more, or all of non-branched chain amino acids. In some embodiments, the compositions are substantially free of one or more, or all of non-branched chain amino acids in free amino acid form. For example, the composition can be substantially free of alanine, arginine, asparagine, aspartic acid, cysteine, glutamic acid, glutamine, glycine, histidine, lysine, methionine, phenylalanine, proline, serine, threonine, tryptophan, and/or tyrosine. The composition can be substantially free of alanine, arginine, asparagine, aspartic acid, cysteine, glutamic acid, glutamine, glycine, histidine, lysine, methionine, phenylalanine, proline, serine, threonine, tryptophan, and/or tyrosine in free amino acid form. In some embodiments, the composition is substantially free of isoleucine and/or valine in free form.

In some embodiments, a method described herein can include administration of a salt, derivative, metabolite, catabolite, anabolite, precursor, and/or analog of any branched chain amino acids. The metabolite can be a metabolite of leucine, such as HMB. Metabolites of branched chain amino acids can include hydroxymethylbutyrate (HMB), α-hydroxyisocaproic acid, and keto-isocaproic acid (KIC), keto isovalerate, and keto isocaproate. Non-limiting exemplary anabolites of branched chain amino acids can include glutamate, glutamine, threonine, α-ketobytyrate, α-aceto-α-hydroxy butyrate, α,β-dihydroxy-β-methylvalerate, α-keto-β-methylvalerate, α,β-dihydroxy isovalerate, and α-keto isovalerate.

In certain embodiments of the invention, any of the compositions to be administered to a subject can be formulated such that they do not contain (or exclude) one or more amino acids selected from the group consisting of lysine, glutamate, proline, arginine, valine, isoleucine, aspartic acid, asparagine, glycine, threonine, serine, phenylalanine, tyrosine, histidine, alanine, tryptophan, methionine, glutamine, taurine, carnitine, cystine and cysteine. Any of the compositions disclosed herein can be formulated such that they do not contain (or exclude) one or more free amino acids selected from the group consisting of lysine, glutamate, proline, arginine, valine, isoleucine, aspartic acid, asparagine, glycine, threonine, serine, phenylalanine, tyrosine, histidine, alanine, tryptophan, methionine, glutamine, taurine, carnitine, cystine and cysteine. In some cases, a composition does not contain any non-branched chain amino acids. In some cases, a composition does not contain any non-branched chain amino acids in free amino acid form. The mass or molar amount of a non-branched chain amino acid in a composition can be less than 0.01, 0.1, 0.5, 1, 2, or 5% of the total composition. The mass or molar amount of a non-branched chain amino acid in free amino acid form can be less than 0.01, 0.1, 0.5, 1, 2, or 5% of the total composition. The mass or molar amount of any branched-chain amino acid or metabolite thereof, aside from leucine or its metabolites can be less than 0.01, 0.1, 0.5, 1, 2, or 5% of the total composition. The mass or molar amount of any branched-chain amino acid in free amino acid form or metabolite thereof, aside from leucine or its metabolites can be less than 0.01, 0.1, 0.5, 1, 2, or 5% of the total composition.

Exemplary Sirtuin Pathway Activators

Sirtuin pathway activators can include any agents which activate one or more components of a sirtuin pathway. The sirtuin pathway includes, without limitation, signaling molecules such as, Sirt1, Sirt3, and AMPK. The output of the pathway can be determined by the expression level and/or the activity of the pathway and/or a physiological effect. In some embodiments, activation of the Sirt1 pathway includes stimulation of PGC1-α and/or subsequent stimulation of mitochondrial biogenesis and fatty acid oxidation. An increase or activation of a sirtuin pathway can be observed by an increase in the activity of a pathway component protein. For example, the protein can be Sirt1, PGC1-α, AMPK, Epac1, Adenylyl cyclase, Sirt3, or any other proteins and their respective associated proteins along the signaling pathway depicted in FIG. 1 (Park et. al., "Resveratrol Ameliorates Aging-Related Metabolic Phenotypes by Inhibiting cAMP Phosphodiesterases," Cell 148, 421-433 Feb. 3, 2012. Non-limiting examples of physiological effects that can serve as measures of sirtuin pathway output include mitochondrial biogenesis, fatty acid oxidation, glucose uptake, palmitate uptake, oxygen consumption, carbon dioxide production, weight loss, heat production, visceral adipose tissue loss, respiratory exchange ratio, insulin sensitivity, inflammation marker level, vasodilation, browning of fat cells, and irisin production. Examples of indicia of browning of fat cells include, without limitation, increased fatty acid oxidation, and expression of one or more brown-fat-selective genes (e.g. Ucp1, Cidea, Prdm16, and Ndufs1). In some embodiments, changes in one or more physiological effects that can serve as measures of sirtuin pathway output are induced by increasing irisin production.

An increase in mitochondrial biogenesis can be evidenced by an increase in the formation of new mitochondria and/or by an increase in mitochondrial functions, such as increased fatty acid oxidation, increased heat generation, increased insulin sensitivity, increased in glucose uptake, increased in vasodilation, decreased in weight, decreased in adipose volume, and decreased inflammatory response or markers in a subject.

In some embodiments the sirtuin pathway activator is a sirtuin activator. The sirtuin activator can be a Sirt1 activator, a Sirt2 activator, and/or Sirt3 activator. Sirt1 activity can be determined by measuring deacetylation of a substrate, which can be detected using a fluorophore. An increase in sirt1, sirt2, or sirt3 is observed by applying a corresponding substrate in a deacylation assay conducted in vitro. The substrate for measuring SIRT1 activity can be any substrate known in the art (for example a peptide containing amino acids 379-382 of human p53 (Arg-His-Lys-Lys[Ac]). The substrate for measuring SIRT3 activity can be any substrate known in the art (for example a peptide containing amino acids 317-320 of human p53 (Gln-Pro-Lys-Lys[Ac])).

Exemplary sirtuin activators can include those described in Howitz et al. (2003) Nature 425: 191 and include, for example, resveratrol (3,5,4'-Trihydroxy-trans-stilbene), butein (3,4,2',4'-Tetrahydroxychalcone), piceatannol (3,5,3',4'-Tetrahydroxy-trans-stilbene), isoliquiritigenin (4,2',4'-Trihydroxychalcone), fisetin (3,7,3',4'-Tetrahyddroxyflavone), quercetin (3,5,7,3',4'-Pentahydroxyflavone), Deoxyrhapontin (3,5-Dihydroxy-4'-methoxystilbene 3-O-β-D-glucoside); trans-Stilbene; Rhapontin (3,3',5-Trihydroxy-4'-methoxystilbene 3-O-β-D-glucoside); cis-Stilbene; Butein (3,4,2',4'-Tetrahydroxychalcone); 3,4,2'4'6'-Pentahydroxychalcone; Chalcone; 7,8,3',4'-Tetrahydroxyflavone; 3,6,2',3'-Tetrahydroxyflavone; 4'-Hydroxyflavone; 5,4'-Dihydroxyflavone 5,7-Dihydroxyflavone; Morin (3,5,7,2',4'-Pentahydroxyflavone); Flavone; 5-Hydroxyflavone; (−)-Epicatechin (Hydroxy Sites: 3,5,7,3',4'); (−)-Catechin (Hydroxy Sites: 3,5,7,3',4'); (−)-Gallocatechin (Hydroxy Sites: 3,5,7,3',4',5') (+)-Catechin (Hydroxy Sites: 3,5,7,3',4'); 5,7,3',4',5'-pentahydroxyflavone; Luteolin (5,7,3',4'-Tetrahydroxyflavone); 3,6,3',4'-Tetrahydroxyflavone; 7,3',4',5'-Tetrahydroxyflavone; Kaempferol (3,5,7,4'-Tetrahydroxyflavone); 6-Hydroxyapigenin (5,6,7,4'-Tetrahydoxyflavone); Scutellarein); Apigenin (5,7,4'-Trihydroxyflavone); 3,6,2',4'-Tetrahydroxyflavone; 7,4'-Dihydroxyflavone; Daidzein (7,4'-Dihydroxyisoflavone); Genistein (5,7,4'-Trihydroxyflavanone); Naringenin (5,7,4'-Trihydroxyflavanone); 3,5,7,3',4'-Pentahydroxyflavanone; Flavanone; Pelargonidin chloride (3,5,7,4'-Tetrahydroxyflavylium chloride); Hinokitiol (b-Thujaplicin; 2-hydroxy-4-isopropyl-2,4,6-cycloheptatrien-1-one); L-(+)-Ergothioneine ((S)-a-Carboxy-2,3-dihydro-N,N,N-trimethyl-2-thioxo-1H-imidazole-4-ethanaminium inner salt); Caffeic Acid Phenyl Ester; MCI-186 (3-Methyl-1-phenyl-2-pyrazolin-5-one); HBED (N,N'-Di-(2-hydroxybenzyl) ethylenediamine-N,N'-diacetic acid-H2O); Ambroxol (trans-4-(2-Amino-3,5-dibromobenzylamino) cyclohexane-HCl; and U-83836E ((−)-2-((4-(2,6-di-1-Pyrrolidinyl-4-pyrimidinyl)-1-piperzainyl)methyl)-3,4-dihydro-2,5,7,8-tetramethyl-2H-1-benzopyran-6-ol.2HCl). Analogs and derivatives thereof can also be used.

In some embodiments the sirtuin pathway activator is an AMPK pathway activator. AMPK activity can be determined by any means known in the art, such as, e.g., measuring AMPK phosphorylation via an ELISA assay or by Western blot. The AMPK pathway activator can be a biguanide. Examples of biguanides include and are not limited to metformin, buformin, phenformin, proguanil or the like.

In some embodiments, the sirtuin pathway activator (e.g., AMPK pathway activator) is a polyphenol. Exemplary polyphenols include, e.g., chlorogenic acid, resveratrol, caffeic acid, piceatannol, ellagic acid, epigallocatechin gallate (EGCG), stilbene, hydroxycinnamic acid, grape seed extract, or any analog thereof. In some embodiments, the sirtuin pathway activator is resveratrol, an analog thereof, or a metabolite thereof. For example, the activator can be pterostilbene or a small molecule analog of resveratrol. Examples of small molecule analogs of resveratrol are described in U.S. Patent Application Nos. 20070014833, 20090163476, and 20090105246, which are incorporated herein by reference in its entirety.

The polyphenol can be a substantially homogeneous population of polyphenols. The polyphenol can be one type of polyphenol, wherein the composition can exclude all other types of polyphenols. In some embodiments, an invention method comprises administration one type of polyphenol, and exclude all other types of polyphenols. In some embodiments, an invention method comprises administration of two, three, or four types of polyphenols, and exclude all other types of polyphenols. In some embodiments, an invention method comprises administration of 1, 2, 3, or 4 types of polyphenols and less than 0.1, 0.5, 1, or 2% of any other types of polyphenols.

Sirtuin pathway activators can also include PDE inhibitors. PDE inhibitors can include non-specific PDE inhibitors. PDE inhibitors can be naturally occurring or non-naturally occurring (e.g. manufactured), and may be provided in the form of a natural source comprising the PDE inhibitor, or an extract thereof (e.g. purified). Examples of non-specific PDE inhibitors include, but are not limited to, caffeine, theophylline, theobromine, 3-isobutyl-1-methylxanthine (IBMX), pentoxifylline (3,7-dihydro-3,7-dimethyl-1-(5oxohexyl)-1H-purine-2, 6-dione), aminophylline, paraxanthine, and salts, derivatives, metabolites, catabolites, anabolites, precursors, and analogs thereof. Non-limiting examples of natural sources of PDE inhibitors include coffee, tea, guarana, verba mate, cocoa, and chocolate (e.g. dark chocolate).

Sirtuin pathway activators can include irisin, quinic acid, cinnamic acid, ferulic acid, fucoxanthin, rosiglitazone, or any analog thereof. Sirtuin-pathway activators can also include isoflavones, pyroloquinoline (PQQ), quercetin, L-carnitine, lipoic acid, coenzyme Q10, pyruvate, 5-aminoimidazole-4-carboxamide ribotide (ALCAR), bezfibrate, oltipraz, and/or genistein.

Sirtuin pathway activators can agents that stimulate expression of the Fndc5, PGC1-α, or UCP1. The expression can be measured in terms of the gene or protein expression level. Alternatively, the sirtuin pathway activator can be irisin. Methods for increasing the level of irisin are described in Bostrom et al., "A PGC1-α-dependent myokine that drives brown-fat-like development of white fat and thermogenesis," Nature, Jan. 11, 2012.

Sirtuin pathway activators can include thiazolidinediones. Exemplary thiazolidinediones include, e.g., rosiglitazone, pioglitazone, troglitazone, and any analogs thereof.

Exemplary PDE Inhibitors

One or more methods of the invention can further comprise administering to a subject a PDE inhibitor. A PDE inhibitor can act as a sirtuin pathway activator. The PDE inhibitor can be selective or non-selective. The PDE inhibitor can exhibit selective inhibition to a PDE subclass, for example PDE 5. Examples of selective PDE inhibitors include inhibitors to PDE 1, 2, 3, 4, 5, 6, 7, 8, 9, 10, or 11. A non-selective PDE inhibitor can be one that does not distinguish among sub-classes of phosphodiesterases. In addition, some non-selective PDE inhibitors may interact with more than one metabolic pathway. For examine, some non-selective PDE inhibitors may be xanthine derivatives and serve as adenosine antagonists and have unknown interactions with other metabolic pathways. Selective PDE inhibitors can be PDE inhibitors that exhibit preferential interaction with a selected PDE. For example, a PDE inhibitor can have a strong interaction with PDE 5, and very little interaction with other PDE sub-classes.

PDE inhibitors can be naturally occurring or non-naturally occurring (e.g. manufactured), and may be provided in the form of a natural source comprising the PDE inhibitor, or an extract thereof (e.g. purified). In some embodiments, the PDE inhibitor is a non-specific PDE inhibitor. Examples of non-specific PDE inhibitors include, but are not limited to, caffeine, theophylline, theobromine, 3-isobutyl-1-methylxanthine (IBMX), pentoxifylline (3,7-dihydro-3,7-dimethyl-1-(5oxohexyl)-1H-purine-2, 6-dione), aminophylline, paraxanthine, and salts, derivatives, metabolites, catabolites, anabolites, precursors, and analogs thereof. The PDE inhibitor can be sourced from a natural source of PDE inhibitors. Non-limiting examples of natural sources of PDE inhibitors include coffee, tea, guarana, verba mate, cocoa, and chocolate (e.g. dark chocolate).

Any agents that selectively and negatively regulate a PDE subclass, such as PDE 5, expression or activity can be used as selective PDE inhibitors in the compositions and methods of the invention.

For example, a selective PDE inhibitor alternatively can be an agent that exhibits a 50% inhibitory concentration (IC50) with respect to a PDE subclass, such as PDE 5, that is at least at least 10-fold, at least 20-fold, at least 50-fold, at least 100-fold, at least 1000-fold at least 10,000-fold, or more, lower than the inhibitor's IC50 with respect to one, two, three, or more other PDE subclasses. In some embodiment, a selective PDE inhibitor can be an agent that exhibits a 50% inhibitory concentration (IC50) with respect to a PDE subclass, such as PDE 5, that is at least at least 10-fold, at least 20-fold, at least 50-fold, at least 100-fold, at least 1000-fold, at least 10,000-fold, or more, lower than the inhibitor's IC50 with respect to all other PDE subclasses.

In one aspect, IC50 is a determination of the concentration at which 50% of a given PDE is inhibited in a cell-based assay. IC50 determinations can be accomplished using any conventional techniques known in the art. In general, an IC50 can be determined by measuring the activity of a given enzyme in the presence of a range of concentrations of the inhibitor under study. The experimentally obtained values of enzyme activity then are plotted against the inhibitor concentrations used. The concentration of the inhibitor that shows 50% enzyme activity (as compared to the activity in the absence of any inhibitor) is taken as the "IC50" value. Analogously, other inhibitory concentrations can be defined through appropriate determinations of activity. For example, in some settings it can be desirable to establish a 90% inhibitory concentration, i.e., IC90, etc.

Methods for measuring selectivity of PDE inhibitors are described in "Phosphodiesterase-5 Gln-817 is critical for cGMP, vardenafil, or sildenafil affinity: its orientation impacts cGMP but not cAMP affinity" by Zoraghi (2006) and "Cyclic Nucleotide Phosphodiesterases: Molecular Regulation to Clinical Use" by Bender (2006) which are incorporated herein in its entirety by reference.

The subject biologically active agent may inhibit PDE activity with an IC50 value of about 100 nM or less, preferably about 50 nM, about 25 nM, about 10 nM, about 5 nM, about 1 nM, 100 pM, 50 pM, 25 pM, 10 pM, 1 pM, or less, as ascertained in a cell-based assay or an in vitro kinase assay.

In some embodiments, the PDE inhibitor is a PDE1 inhibitor such as nimodipine, vinopocetine, and IC224. The PDE 1 inhibitor can interact with PDE1, which is a Ca2+/calmodulin-regulated phosphodiesterase that serves to degrade both cAMP and cGMP. The vinopocetine can be derived from periwinkle extract, and it can serve as a cerebrovascularvasodilator. Vinopocetine can be in the form of a dietary supplement.

In other embodiments, the PDE inhibitor is a PDE3 inhibitor such as meribendan, arinone and cilostamide. The PDE inhibitor can be a PDE4 inhibitor, such as apremilast, mesembrine, ibudilast, piclamilast, luteolin, roflumilast, cilomilast, diazepam, rolipram and YM796. The PDE inhibitor can be a PDE4 inhibitor, such as rolipram and YM796. The PDE4 inhibitor can interact with PDE 4, which is a cAMP-specific phosphodiesterase that predominates in immune cells.

In some embodiments, the PDE inhibitor is a PDE5 specific inhibitor, icariin, sildenafil, tadalafil, vardenafil, avanafil, iodenafil, mirodenafil, udenafil, and zaprinast. In some embodiments, the PDE5 inhibitor is icariin. In some embodiments, the PDE5 inhibitor is sildenafil. In some embodiments, the PDE5 inhibitor is tadalafil. In some embodiments, the PDE5 inhibitor is vardenafil. In some embodiments, the PDE5 inhibitor is avanafil. In some embodiments, the PDE5 inhibitor is iodenafil. In some embodiments, the PDE5 inhibitor is mirodenafil. In some embodiments, the PDE5 inhibitor is udenafil. In some embodiments, the PDE5 inhibitor is zaprinast. The PDE 5 inhibitor can interact with PDE 5, which is a cGMP-specific PDE. Increases in cGMP signaling can increase mitochondrial biogenesis both in vitro and in vivo. A PDE 5 inhibitor can increase nitric oxide signaling and be an effective vasodilator. Other examples of PDE 5 inhibitors are described in U.S. Pat. Nos. 5,250,534 and 6,469,012, which are each incorporated by reference in their entirety.

In some embodiments, a PDE inhibitor is administered in place of or in addition to resveratrol or other sirtuin pathway activator. In some embodiments, compositions comprising one or more components described herein comprise a PDE inhibitor in place of or in addition to resveratrol or other sirtuin pathway activator.

A method of reducing, the sustained reduction of, and/or preventing NASH or hepatic steatosis in a subject can comprise co-administering to the subject (a) a sirtuin pathway activator, (b) a branched chain amino acid in free amino acid form or metabolite thereof, and optionally (c) a PDE inhibitor. In some embodiments, the sirtuin pathway activator is an AMPK activator. In some embodiments, the AMPK activator is a biguanide. In particular embodiments, the biguanide is metformin. In some embodiments, the branched chain amino acid in free amino acid form is leucine. In some embodiments, the PDE inhibitor is a PDE5 inhibitor. Exemplary PDE5 inhibitors are described herein. The PDE5 inhibitor can be, for example, icariin. The PDE5 inhibitor can be any one of sildenafil, tadalafil, vardenafil, udenafil, or zaprinast. In some embodiments, metformin is co-administered with a metabolite of leucine. In particular embodiments, the metabolite of leucine is HMB. In particular embodiments, the metabolite of leucine is KIC. In some embodiments, more than one sirtuin pathway activator is co-administered with a branched chain amino acid in free amino acid form or metabolite thereof (e.g., co-administered with leucine in free amino acid form, HMB, or KIC). For instance, a method of the invention may comprise co-administering a biguanide, a polyphenol, and a branched chain amino acid in free amino acid form or metabolite thereof. For example, a method of the invention can comprise co-administering to a subject metformin, resveratrol, and leucine in free amino acid form. A method of the invention can comprise co-administering to a subject metformin, resveratrol, and HMB. A method of the invention can comprise co-administering to a subject metformin, resveratrol, and KIC. In some embodiments, a method of the invention can comprise co-administering to a subject metformin, leucine, and sildenafil.

Another method of reducing, the sustained reduction of, and/or preventing NASH or hepatic steatosis in a subject can comprise co-administering to the subject (a) a PDE inhibitor, and (b) a branched chain amino acid in free amino acid form or a metabolite thereof. In some embodiments, the branched chain amino acid in free amino acid form is leucine. In some embodiments, a metabolite of leucine is co-administered. The metabolite can be, e.g., HMB or KIC. In some embodiments, the PDE inhibitor is a PDE5 inhibitor. Exemplary PDE5 inhibitors are described herein. The PDE5 inhibitor can be, for example, icariin. The PDE5 inhibitor can be any one of sildenafil, tadalafil, vardenafil, udenafil, or zaprinast.

In some embodiments, the particular choice of compounds depends upon the diagnosis of the attending physicians and their judgment of the condition of the individual and the appropriate treatment protocol. The compounds are optionally administered concurrently (e.g., simultaneously, essentially simultaneously or within the same treatment protocol) or sequentially, depending upon the nature of the disease, disorder, or condition, the condition of the individual, and the actual choice of compounds used. In certain instances, the determination of the order of administration, and the number of repetitions of administration of each therapeutic agent during a treatment protocol, is based on an evaluation of the disease being treated and the condition of the individual.

In some embodiments, therapeutically-effective dosages vary when the drugs are used in treatment combinations. Methods for experimentally determining therapeutically-effective dosages of drugs and other agents for use in combination treatment regimens are described in the literature.

In some embodiments of the combination therapies described herein, dosages of the co-administered compounds vary depending on the type of co-drug employed, on the specific drug employed, on the disease or condition being treated and so forth. In addition, when co-administered with one or more biologically active agents, the compound provided herein is optionally administered either simultaneously with the biologically active agent(s), or sequentially. In certain instances, if administered sequentially, the attending physician will decide on the appropriate sequence of therapeutic compound described herein in combination with the additional therapeutic agent.

The multiple therapeutic agents are optionally administered in any order or even simultaneously. If simultaneously, the therapeutic agents are optionally provided in a single, unified form, or in multiple forms (by way of example only, either as a single pill or as two separate pills). In certain instances, one of the therapeutic agents is optionally given in multiple doses. In other instances, both are optionally given as multiple doses. If not simultaneous, the timing between the multiple doses is any suitable timing, e.g., from more than zero weeks to less than four weeks. In addition, the combination methods, compositions and formulations are not to be limited to the use of only two agents; the use of multiple therapeutic combinations is also envisioned (including two or more compounds described herein).

In certain embodiments, a dosage regimen to treat, prevent, or ameliorate the condition(s) for which relief is sought, is modified in accordance with a variety of factors. These factors include the disorder from which the subject suffers, as well as the age, weight, sex, diet, and medical condition of the subject. Thus, in various embodiments, the dosage regimen actually employed varies and deviates from the dosage regimens set forth herein.

In some embodiments, the pharmaceutical agents that make up the combination therapy described herein are provided in a combined dosage form or in separate dosage forms intended for substantially simultaneous administration. In certain embodiments, the pharmaceutical agents that make up the combination therapy are administered sequentially, with either therapeutic compound being administered by a regimen calling for two-step administration. In some embodiments, two-step administration regimen calls for sequential administration of the active agents or spaced-apart administration of the separate active agents. In certain embodiments, the time period between the multiple administration steps varies, by way of non-limiting example, from a few minutes to several hours, depending upon the properties of each pharmaceutical agent, such as potency, solubility, bioavailability, plasma half-life and kinetic profile of the pharmaceutical agent.

In various other embodiments, compositions for use in practicing one or more methods of the invention are formulated such that they do not contain (or exclude) one or more of the following ingredients: caffeine, green tea extract or extracts from guarana seed or guarana plants. Compositions can also be formulated such that they are substantially free of high glycemic index carbohydrate, such as, e.g., simple carbohydrates, including sugars such as but not limited to sucrose, glucose, dextrose, maltose, fructose, and galactose, among others.

Dosing Amounts

The amount of pharmaceutical agent, or any other component used in a combination composition described herein, can be an amount that is therapeutically effective. The amount of pharmaceutical agent, or any other component used in a combination composition described herein, can be an amount that is sub-therapeutic. In some embodiments, using sub-therapeutic amounts of an agent or component can reduce the side-effects of the agent. Use of sub-therapeutic amounts can still be effective, particularly when used in synergy with other agents or components.

A sub-therapeutic amount of the agent or component can be such that it is an amount below which would be considered therapeutic. For example, FDA guidelines can suggest a specified level of dosing to treat a particular condition, and a sub-therapeutic amount would be any level that is below the FDA suggested dosing level. The sub-therapeutic amount can be about 1, 5, 10, 15, 20, 25, 30, 35, 50, 75, 90, or 95% less than the amount that is considered to be a therapeutic amount. The therapeutic amount can be assessed for individual subjects, or for groups of subjects. The group of subjects can be all potential subjects, or subjects having a particular characteristic such as age, weight, race, gender, or physical activity level.

In the case of metformin, a physician suggested starting dose can be 1000 mg daily, with subject specific dosing having a range of 500 mg to a maximum of 2550 mg daily (metformin hydrochloride extended-release tablets label www.accessdata.fda.gov/drugsatfda docs/label/2008/021574s0101bl.pdf). The particular dosing for a subject can be determined by a clinician by titrating the dose and measuring the therapeutic response. The therapeutic dosing level can be determined by measuring fasting plasma glucose levels and measuring glycosylated hemoglobin. A sub-therapeutic amount can be any level that would be below the recommended dosing of metformin. For example, if a subject's therapeutic dosing level is determined to be 700 mg daily, a dose of 600 mg would be a sub-therapeutic amount. Alternatively, a sub-therapeutic amount can be determined relative to a group of subjects rather than an individual subject. For example, if the average therapeutic amount of metformin for subjects with weights over 300 lbs is 2000 mg, then a sub-therapeutic amount can be any amount below 2000 mg. In some embodiments, the dosing can be recommended by a healthcare provider including, but not limited to a patient's physician, nurse, nutritionist, pharmacist, or other health care professional. A health care professional may include a person or entity that is associated with the health care system. Examples of health care professionals may include surgeons, dentists, audiologists, speech pathologists, physicians (including general practitioners and specialists), physician assistants, nurses, midwives, pharmaconomists/pharmacists, dietitians, therapists, psychologists, physical therapists, phlebotomists, occupational therapists, optometrists, chiropractors, clinical officers, emergency medical technicians, paramedics, medical laboratory technicians, radiographers, medical prosthetic technicians social workers, and a wide variety of other human resources trained to provide some type of health care service.

The invention provides for compositions that can comprise any combination of agents, such as leucine, metabolites of leucine, such as HMB or KIC, PDE inhibitors (e.g., PDE5 inhibitors such as, by way of example only, sildenafil, icariin), sirtuin pathway activators such as, e.g., AMPK activators, polyphenols such as, e.g., resveratrol, and sirtuin activators, that have been isolated from one or more sources. The agents can be isolated from natural sources or created from synthetic sources and then enriched to increase the purity of the components. For example, sildenafil can be created from a synthetic source and then enriched by one or more purification methods. Additionally, leucine (e.g., free leucine), can be isolated from a natural source and then enriched by one or more separations. The isolated and enriched components, such as, e.g., metformin, resveratrol, icariin, sildenafil, free leucine, HMB, and KIC can then be formulated for administration to a subject in any combination.

Dosage of Branched Chain Amino Acid

Any of the invention methods can comprise administering a dose of a branched chain amino acid in free amino acid form, and/or a dose of a metabolite thereof. The dose of the branched chain amino acid in free amino acid form, or metabolite thereof, can be a therapeutic dose. The dose of the branched chain amino acid in free amino acid form or metabolite thereof can be a sub-therapeutic dose. A sub-therapeutic dose of leucine in free amino acid form can be about, less than about, or more than about 0.25-3.0 g (e.g. 0.25, 0.5, 0.75, 1, 1.25, 1.5, 1.75, 2, 2.5, 3, or more g). A sub-therapeutic dose of leucine in free amino acid form can be about, less than about, or more than about 0.25-3.0 g/day (e.g. 0.25, 0.5, 0.75, 1, 1.25, 1.5, 1.75, 2, 2.5, 3, or more g/day). In some embodiments, the method comprises administering less than 3.0 g leucine in free amino acid form per day. A sub-therapeutic dose of HMB can be about, less than about, or more than about 0.05-3.0 g (e.g. 0.05, 0.1, 0.2, 0.4, 0.5, 0.75, 1, 1.5, 2, 2.5, 3, or more g). A sub-therapeutic dose of HMB can be about, less than about, or more than about 0.05-3.0 g/day (e.g. 0.05, 0.1, 0.2, 0.4, 0.5, 0.75, 1, 1.5, 2, 2.5, 3, or more g/day). A sub-therapeutic dose of KIC can be about, less than about, or more than about 0.1-3.0 g (e.g. 0.1, 0.2, 0.4, 0.5, 0.75, 1, 1.25, 1.5, 1.75, 2, 2.5, 3, or more g). A sub-therapeutic dose of KIC can be about, less than about, or more than about 0.1-3.0 g/day (e.g. 0.1, 0.2, 0.4, 0.5, 0.75, 1, 1.25, 1.5, 1.75, 2, 2.5, 3, or more g/day).

Any of the invention methods can comprise administering a dose of metformin. The dose of metformin can be a therapeutic dose. The therapeutic dose can be above 500 mg, above 600 mg, above 700 mg, above 800 mg, above 900 mg, or above 1000 mg (1 g). A therapeutic dose of metformin can be about 1 g, about 1.1 g, about 1.2 g, about 1.3 g, about 1.4 g, about 1.5 g, about 1.6 g, about 1.7 g, about 1.8 g, about 1.9 g, about 2 g, or more than 2 g. The therapeutic dose can be above 500 mg/day, above 600 mg/day, above 700 mg/day, above 800 mg/day, above 900 mg/day, above 1000 mg/day (1 g/day). A therapeutic dose of metformin can be about 1 g/day, about 1.1 g/day, about 1.2 g/day, about 1.3 g/day, about 1.4 g/day, about 1.5 g/day, about 1.6 g/day, about 1.7 g/day, about 1.8 g/day, about 1.9 g/day, about 2 g/day, or more than 2 g/day. The dose of metformin can be a sub-therapeutic dose. The sub-therapeutic dose of metformin can be about 1-1000 mg, about 5-500 mg, about 10-100 mg, about 30-90 mg, about 50-70 mg, or about 62.5 mg. The sub-therapeutic dose of metformin can be, e.g., 1, 5, 10, 15, 25, 50, 125, 250, or 500 mg. The dose of metformin can be a sub-therapeutic dose. The sub-therapeutic dose of metformin can be about 40-70, 25-1000 mg/day, about 50-500 mg/day, about 100-500 mg/day. The sub-therapeutic dose of metformin can be about, less than about, or greater than about 1, 5, 10, 15, 25, 50, 60 125, 250, or 500 mg/day. The metformin can be administered as a unit dose. The unit dose of metformin can be 1, 5, 10, 15, 25, 50, 62.5, 125 or 250 mg.

Dosage of Polyphenols

Any of the invention methods can comprise administering a dose of a polyphenol, e.g., resveratrol. The dose may be administered daily. The dose can be a low dose, a medium dose, or a high dose. A low dose of resveratrol may comprise about, less than about, or more than about 0.5 mg, 1 mg, 2.5 mg, 5 mg, 7.5 mg, 10 mg, 12.5 mg, 15 mg, 20 mg, 25 mg, 50 mg, 75 mg, 100 mg, or more; a medium dose of resveratrol may comprise about, less than about, or more than about 20 mg, 25 mg, 50 mg, 75 mg, 100 mg, 125 mg, 150 mg, 175 mg, 200 mg, 250 mg, or more; and a high dose of resveratrol may comprise about, less than about, or more than about 150 mg, 175 mg, 200 mg, 225 mg, 250 mg, 300 mg, 350 mg, 400 mg, or more. A daily low dose of resveratrol may comprise about, less than about, or more than about 0.5 mg, 1 mg, 2.5 mg, 5 mg, 7.5 mg, 10 mg, 12.5 mg, 15 mg, 20 mg, 25 mg, 50 mg, 75 mg, 100 mg, or more; a daily medium dose of resveratrol may comprise about, less than about, or more than about 20 mg, 25 mg, 50 mg, 75 mg, 100 mg, 125 mg, 150 mg, 175 mg, 200 mg, 250 mg, or more; and a daily high dose of resveratrol may comprise about, less than about, or more than about 150 mg, 175 mg, 200 mg, 225 mg, 250 mg, 300 mg, 350 mg, 400 mg, or more.

Dosage of Thiazoladinediones

Any of the invention methods can comprise administering a dose of a thiazolidinedione. Exemplary thiazoladinediones are described herein. The dose of thiazolidinedione can be a therapeutic dose or a sub-therapeutic dose. The thiazolidinedione can be rosiglitazone. The dose of the rosiglitazone can be at least 100 µg. The dose of the rosiglitazone can be about or less than about 4 mg. The dose of the rosiglitazone can be 100 µg-4 mg, can be 200 µg-2 mg, can be 400 µg to 1000 µg. The thiazolidinedione can be pioglitazone. The dose of the pioglitazone can be at least 100 µg. The dose of the pioglitazone can be about or less than about 15 mg. The dose of the pioglitazone can be 100 µg-45 mg, can be 200 µg-10 mg, can be 400 µg to 5 mg, can be 500 µg to 1 mg.

Dosages of PDE Inhibitor

In some embodiments, a composition comprises an amount of a selective PDE inhibitor (e.g., PDE-5 inhibitor including but not limited to sildenafil or icariin). The amount of a PDE inhibitor may be a subtherapeutic amount, and/or an amount that is synergistic with one or more other compounds in the composition or one or more of the compounds administered simultaneously or in close temporal proximity with the composition. In some embodiments, the PDE inhibitor is administered in a low dose, a medium dose, or a high dose, which describes the relationship between two doses, and generally do not define any particular dose range.

A dose of sildenafil can be about or less than about 0.05, 0.1, 0.5, 1, 2, 5, 10, 20, 40, 60, 80, or 100 mg of sildenafil. A dose of sildenafil can be about 0.05-100, 1-50, or 5-20 mg of sildenafil. A dose of icariin can be about or less than about 1, 10, 12.5, 20, 25, 50, 100, 150, 300, 400, 500, 750, 1000, 1500, or 2000 mg of icariin. A dose of icariin can be about 1-100, 5-60, or 10-30 mg of icariin. A dose of tadalafil can be about 0.01, 0.05, 0.1, 0.5, 1, 15, 2, 2.5, 5, 10, 15, or 20 mg. A dose of tadalafil can be about 0.1-50, 0.5-20, or 1-10 mg. A dose of vardenafil can be about 0.01, 0.05, 0.1, 0.5, 1, 15, 2, 2.5, 5, 10, 15, or 20 mg. A dose of vardenafil can be about 0.1-50, 0.5-20, or 1-10 mg. A dose of avanafil can be about 1, 10, 20, 50, 100, 150, 300, 400, 500, 750, 1000, 1500, or 2000 mg. A dose of avanafil can be about 1-100, 5-50, or 10-40 mg. A dose of lodenafil can be about 0.05, 0.1, 0.5, 1, 2, 5, 10, 20, 50, 80, 100, 150, 300, 400, 500, 750, 1000, 1500, or 2000 mg. A dose of lodenafil can be about 0.05-100, 1-50, or 5-20 mg. A dose of mirodenafil can be about 0.05, 0.1, 0.5, 1, 2, 5, 10, 20, 50, 80, 100, 150, 300, 400, 500, 750, 1000, 1500, or 2000 mg. A dose of mirodenafilcan be about 0.05-100, 1-50, or 5-20 mg. A dose of udenafil can be about 0.05, 0.1, 0.5, 1, 2, 5, 10, 20, 50, 80, 100, 150, 300, 400, 500, 750, 1000, 1500, or 2000 mg. A dose of udenafil can be about 0.05-100, 1-50, or 5-20 mg.

A daily dose of sildenafil can be about or less than about 0.05, 0.1, 0.5, 1, 2, 5, 10, 20, 40, 60, 80, or 100 mg of sildenafil. A daily dose of sildenafil can be about 0.05-100, 1-50, or 5-20 mg of sildenafil. A daily dose of icariin can be about or less than about 1, 10, 20, 25, 50, 100, 150, 300, 400, 500, 750, 1000, 1500, or 2000 mg of icariin. A daily dose of icariin can be about 1-100, 10-75, or 20-40 mg of icariin. A daily dose of tadalafil can be about 0.01, 0.05, 0.1, 0.5, 1, 15, 2, 2.5, 5, 10, 15, or 20 mg. A daily dose of tadalafil can be about 0.1-50, 0.5-20, or 1-10 mg. A daily dose of vardenafil can be about 0.01, 0.05, 0.1, 0.5, 1, 15, 2, 2.5, 5, 10, 15, or 20 mg. A daily dose of vardenafil can be about 0.1-50, 0.5-20, or 1-10 mg. A daily dose of avanafil can be about 1, 10, 20, 50, 100, 150, 300, 400, 500, 750, 1000, 1500, or 2000 mg. A daily dose of avanafil can be about 1-100, 5-50, or 10-40 mg. A daily dose of lodenafil can be about 0.05, 0.1, 0.5, 1, 2, 5, 10, 20, 50, 80, 100, 150, 300, 400, 500, 750, 1000, 1500, or 2000 mg. A daily dose of lodenafil can be about 0.05-100, 1-50, or 5-20 mg. A daily dose of mirodenafil can be about 0.05, 0.1, 0.5, 1, 2, 5, 10, 20, 50, 80, 100, 150, 300, 400, 500, 750, 1000, 1500, or 2000 mg. A daily dose of mirodenafilcan be about 0.05-100, 1-50, or 5-20 mg. A daily dose of udenafil can be about 0.05, 0.1, 0.5, 1, 2, 5, 10, 20, 50, 80, 100, 150, 300, 400, 500, 750, 1000, 1500, or 2000 mg. A daily dose of udenafil can be about 0.05-100, 1-50, or 5-20 mg.

In some embodiments, a dose of sildenafil can be about or less than about 4 mg. In some embodiments, a daily dose of sildenafil can be about or less than about 4 mg.

Another aspect of the invention provides compositions comprising synergizing amounts of PDE-5 inhibitor, such as, e.g., sildenafil, icariin, tadalafil, vardenafil, avanafil, lodenafil, mirodenafil and udenafil, in combination with leucine, HMB, KIC, and/or resveratrol. Thus, one embodiment provides a composition comprising leucine in an amount of about 0.25 to about 3.0 g and sildenafil in an amount of about 0.05 to about 100 mg. Another embodiment provides a composition comprising HMB in an amount of 0.40-3.0 g and sildenafil in an amount of about 0.05-100 mg. Another embodiment provides for a composition comprising leucine in an amount of about 0.25-about 3.0 g, HMB in an amount of about 0.10 to about 3.0 g and sildenafil in an amount of about 0.05-100 mg. In compositions comprising a PDE inhibitor or methods comprising administration of a PDE inhibitor (separately from or concurrently with one or more other components), the PDE inhibitor may be provided in an amount that produces a peak plasma concentration of about, less than about, or more than about 0.1, 1, 5, 10, 25, 50, 100, 500, 1000, 2500, 5000, 10000, or more nM.

Thus, embodiments of a method of the invention comprise co-administering leucine in free amino acid form in an amount of about 0.25 to about 3.0 g/day and resveratrol in an amount of about 50 to about 500 mg/day. Other embodiments comprise co-administering HMB in an amount of 0.10-3.0 g/day and resveratrol in an amount of about 50-500 mg/day. Other embodiments comprise co-administering KIC in an amount of 0.20-3.0 g/day and resveratrol in an amount of about 50-500 mg/day (or 50 to 500 mg/day).

Other embodiments comprise co-administering leucine in free amino acid form in an amount of about 0.5-about 3.0 g/day, HMB in an amount of about 0.10 to about 3.0 g/day and resveratrol in an amount of about 50 to about 500 mg/day. Other embodiments comprise co-administering leucine in free amino acid form in an amount of about 0.5-about 3.0 g/day, KIC in an amount of about 0.20 to about 3.0 g/day and resveratrol in an amount of about 50 to about 500 mg/day. Other embodiments comprise co-administering leucine in free amino acid form in an amount of about 0.25-about 3.0 g/day, HMB in an amount of about 0.10 to about 3.0 g/day, KIC in an amount of about 0.20 to about 3.0 g/day, and resveratrol in an amount of about 50 to about 500 mg/day.

Some embodiments of a method of the invention comprise co-administering leucine in free amino acid form in an amount of about 0.25 to about 3.0 g/day and metformin in an amount of about 25 to about 500 mg/day. Other embodiments comprise co-administering HMB in an amount of 0.10-3.0 g/day and metformin in an amount of about 25-500 mg/day. Other embodiments comprise co-administering KIC in an amount of 0.20-3.0 g/day and metformin in an amount of about 25-500 mg/day. Other embodiments comprise co-administering leucine in free amino acid form in an amount of about 0.25-about 3.0 g/day, HMB in an amount of about 0.40 to about 3.0 g/day and metformin in an amount of about 25 to about 500 mg/day. Other embodiments comprise co-administering leucine in free amino acid form in an amount of about 0.25-about 3.0 g/day, KIC in an amount of about 0.20 to about 3.0 g/day and metformin in an amount of about 25 to about 500 mg/day. Other embodiments comprise co-administering leucine in free amino acid form in an amount of about 0.25-about 3.0 g/day, HMB in an amount of about 0.10 to about 3.0 g/day, KIC in an amount of about 0.20 to about 3.0 g/day, and metformin in an amount of about 25 to about 500 mg/day. In some embodiments, such methods further comprise co-administering resveratrol in an amount of about 50 to about 500 mg/day.

Some embodiments of a method of the invention comprise co-administering leucine in free amino acid form in an amount of about 0.25 to about 3.0 g/day and a PDE5 inhibitor in an amount of about 0.05 to about 2000 mg/day. Other embodiments comprise co-administering HMB in an amount of 0.10-3.0 g/day and a PDE5 inhibitor in an amount of about 0.05 to about 2000 mg/day. Other embodiments comprise co-administering KIC in an amount of 0.20-3.0 g/day and a PDE5 inhibitor in an amount of about 0.05 to about 2000 mg/day. Other embodiments comprise co-administering leucine in free amino acid form in an amount of about 0.25-about 3.0 g/day, HMB in an amount of about 0.40 to about 3.0 g/day and a PDE5 inhibitor in an amount of about 0.05 to about 2000 mg/day. Other embodiments comprise co-administering leucine in free amino acid form in an amount of about 0.25-about 3.0 g/day, KIC in an amount of about 0.20 to about 3.0 g/day and a PDE5 inhibitor in an amount of about 0.05 to about 2000 mg/day. Other embodiments comprise co-administering leucine in free amino acid form in an amount of about 0.25-about 3.0 g/day, HMB in an amount of about 0.10 to about 3.0 g/day, KIC in an amount of about 0.20 to about 3.0 g/day, and a PDE5 inhibitor in an amount of about 0.05 to about 2000 mg/day. The PDE5 inhibitor can be any of the PDE5 inhibitors described herein. The daily dose of the PDE5 inhibitor can be as described herein. In some embodiments, such methods further comprise co-administering resveratrol in an amount of about 50 to about 500 mg/day or co-administering metformin in an amount of about 25 and about 500 mg/day.

Some embodiments of a method of the invention comprise co-administering leucine in free amino acid form in an amount of about 0.25 to about 3.0 g/day, metformin in an amount of about 25 to about 500 mg/day, and a PDE5 inhibitor in an amount of about 0.05 to about 2000 mg/day. In some embodiments, the PDE5 inhibitor is sildenafil. Other embodiments comprise co-administering HMB in an amount of 0.10-3.0 g/day, metformin in an amount of about 25-500 mg/day, and a PDE5 inhibitor, e.g. sildenafil, in an amount of about 0.05 to about 2000 mg/day. Other embodiments comprise co-administering KIC in an amount of 0.20-3.0 g/day, metformin in an amount of about 25-500 mg/day, and a PDE5 inhibitor, e.g. sildenafil, in an amount of about 0.05 to about 2000 mg/day. Other embodiments comprise co-administering leucine in free amino acid form in an amount of about 0.25-about 3.0 g/day, HMB in an amount of about 0.40 to about 3.0 g/day, metformin in an amount of about 25 to about 500 mg/day, and a PDE5 inhibitor, e.g. sildenafil, in an amount of about 0.05 to about 2000 mg/day. Other embodiments comprise co-administering leucine in free amino acid form in an amount of about 0.25-about 3.0 g/day, KIC in an amount of about 0.20 to about 3.0 g/day, metformin in an amount of about 25 to about 500 mg/day, and a PDE5 inhibitor, e.g. sildenafil, in an amount of about 0.05 to about 2000 mg/day. Other embodiments comprise co-administering leucine in free amino acid form in an amount of about 0.25-about 3.0 g/day, HMB in an amount of about 0.10 to about 3.0 g/day, KIC in an amount of about 0.20 to about 3.0 g/day, metformin in an amount of about 25 to about 500 mg/day, and a PDE5 inhibitor, e.g. sildenafil, in an amount of about 0.05 to about 2000 mg/day. In some embodiments, such methods further comprise co-administering resveratrol in an amount of about 50 to about 500 mg/day.

Any of the above agents can be administered in unit doses. Any of the above agents in the amounts described herein can be administered in unit doses. A unit dose can be a fraction of the daily dose, such as the daily dose divided by the number of unit doses to be administered per day. A unit dose can be a fraction of the daily dose that is the daily dose divided by the number of unit doses to be administered per day and further divided by the number of unit doses (e.g. tablets) per administration. The number of unit doses per administration may be about, less than about, or more than about 1, 2, 3, 4, 5, 6, 7, 8, 9, 10, or more. The number of doses per day may be about, less than about, or more than about 1, 2, 3, 4, 5, 6, 7, 8, 9, 10, or more. The number of unit doses per day may be determined by dividing the daily dose by the unit dose, and may be about, less than about, or more than about 1, 2, 3, 4, 5, 6, 7, 8, 9, 10, 11, 12, 13, 14, 15, 6, 17, 18, 19, 20, or more unit doses per day. For example, a unit dose can be about the daily dose or about ½, ⅓, ¼, ⅕, ⅙, ⅐, ⅛, ⅑, ⅒ of the daily dose. A unit dose can be about one-third of the daily amount and administered to the subject three times daily. A unit dose can be about one-half of the daily amount and administered to the subject twice daily. A unit dose can be about one-fourth of the daily amount with two unit doses administered to the subject twice daily. In some embodiments, a unit dose comprises about, less than about, or more than about 50 mg resveratrol. In some embodiments, a unit dose comprises about, less than about, or more than about 50 mg metformin. In some embodiments, a unit dose comprises about, less than about, or more than about 550 mg leucine. In some embodiments, a unit dose comprises about, less than about, or more than about 200 mg of one or more leucine metabolites. In some embodiments, a unit dose (e.g. a unit dose comprising leucine) is administered as two unit doses two times per day. In some embodiments, a unit dose (e.g. a unit dose comprising one or more leucine metabolites, such as HMB) is administered as one unit dose two timer per day.

The agents described herein (e.g., branched chain amino acid in free amino acid form, metabolites thereof, sirtuin pathway activators, PDE inhibitors) can be administered to a subject orally or by any other methods. Methods of oral administration include administering the composition as a liquid, a solid, or a semi-solid that can be taken in the form of a dietary supplement or a food stuff.

The agents described herein can be co-administered. The agents can be administered simultaneously, e.g., in a single composition, or can be administered sequentially. The agents can be administered sequentially within 1, 2, 3, 4, 5, 6, 7, 8, 9, 10, 11, 12, 13, 14, 15, 30, 60, 90, or 120 minutes from each other.

The agents described herein can be administered periodically. For example, the agents can be administered one, two, three, four times a day, or even more frequent. The subject can be administered every 1, 2, 3, 4, 5, 6 or 7 days. In some embodiments, the agents are administered three times daily. The administration can be concurrent with meal time of a subject. The period of treatment or diet supplementation can be for about 1, 2, 3, 4, 5, 6, 7, 8, or 9 days, 2 weeks, 1-11 months, or 1 year, 2 years, 5 years or even longer. In some embodiments, the subject is administered the agents for six weeks or more. In some embodiments of the invention, the dosages that are administered to a subject can change or remain constant over the period of treatment. For example, the daily dosing amounts can increase or decrease over the period of administration.

The length of the period of administration and/or the dosing amounts can be determined by a physician, a nutritionist, or any other type of clinician. The physician, nutritionist, or clinician can observe the subject's response to the administered compositions and adjust the dosing based on the subject's performance. For example, dosing for subjects that show reduced effects in energy regulation can be increased to achieve desired results.

Any of the agents described herein can be administered to the subject in one or more compositions. A composition for use in practicing any of the methods of the invention can comprise any combination of the agents described herein. For example, an invention composition can comprise one, two, three, four, or more than four of the agents described herein.

Compositions described herein can be compounded into a variety of different dosage forms. For example, compositions can be formulated for oral administration, e.g., as a tablet, chewable tablet, caplets, capsule, soft gelatin capsules, lozenges or solution. Compositions can be formulated as a nasal spray or for injection when in its solution form. In some embodiments, the composition is a liquid composition suitable for oral consumption.

In some embodiments, the agents are formulated into a composition suitable for oral administration. Compositions of the invention suitable for oral administration can be presented as discrete dosage forms, such as capsules, cachets, or tablets, or liquids or aerosol sprays each containing a predetermined amount of an active ingredient as a powder or in granules, a solution, or a suspension in an aqueous or non-aqueous liquid, an oil-in-water emulsion, or a water-in-oil liquid emulsion, including liquid dosage forms (e.g., a suspension or slurry), and oral solid dosage forms (e.g., a tablet or bulk powder). Oral dosage forms may be formulated as tablets, pills, dragees, capsules, emulsions, lipophilic and hydrophilic suspensions, liquids, gels, syrups, slurries, suspensions and the like, for oral ingestion by an individual or a patient to be treated. Such dosage forms can be prepared by any of the methods of formulation. For example, the active ingredients can be brought into association with a carrier, which constitutes one or more necessary ingredients. Capsules suitable for oral administration include push-fit capsules made of gelatin, as well as soft, sealed capsules made of gelatin and a plasticizer, such as glycerol or sorbitol. The push-fit capsules can contain the active ingredients in admixture with filler such as lactose, binders such as starches, and/or lubricants such as talc or magnesium stearate and, optionally, stabilizers. Optionally, the inventive composition for oral use can be obtained by mixing a composition a solid excipient, optionally grinding a resulting mixture, and processing the mixture of granules, after adding suitable auxiliaries, if desired, to obtain tablets or dragee cores. Suitable excipients are, in particular, fillers such as sugars, including lactose, sucrose, mannitol, or sorbitol; cellulose preparations such as, for example, maize starch, wheat starch, rice starch, potato starch, gelatin, gum tragacanth, methyl cellulose, hydroxypropylmethyl-cellulose, sodium carboxymethylcellulose, and/or polyvinylpyrrolidone (PVP). In general, the compositions are prepared by uniformly and intimately admixing the active ingredient with liquid carriers or finely divided solid carriers or both, and then, if necessary, shaping the product into the desired presentation. For example, a tablet can be prepared by compression or molding, optionally with one or more accessory ingredients. Compressed tablets can be prepared by compressing in a suitable machine the active ingredient in a free-flowing form such as powder or granules, optionally mixed with an excipient such as, but not limited to, a binder, a lubricant, an inert diluent, and/or a surface active or dispersing agent. Molded tablets can be made by molding in a suitable machine a mixture of the powdered compound moistened with an inert liquid diluent.

The compositions may be in liquid form. Exemplary liquid forms, which may be formulated for oral administration or for administration by injection, include aqueous solution, suitably flavored syrups, aqueous or oil suspensions, and flavored emulsions with edible oils such as cottonseed oil, sesame oil, coconut oil, or peanut oil as well as elixirs and similar pharmaceutical vehicles. Suitable dispersing or suspending agents for aqueous suspensions include synthetic natural gums, such as tragacanth, acacia, alginate, dextran, sodium carboxymethyl cellulose, methylcellulose, polyvinylpyrrolidone or gelatin. A method of the invention may comprise administering to a subject a combination of an injectable composition and a composition for oral administration.

Liquid preparations for oral administration may take the form of, for example, solutions, syrups or suspensions, or they may be presented as a dry product for reconstitution with water or other suitable vehicles before use. Such liquid preparations may be prepared by conventional means with pharmaceutically acceptable additives such as suspending agents (e.g., sorbitol syrup, methyl cellulose or hydrogenated edible fats); emulsifying agents (e.g., lecithin or acacia); non-aqueous vehicles (e.g., almond oil, oily esters or ethyl alcohol); preservatives (e.g., methyl or propyl p-hydroxybenzoates or sorbic acid); and artificial or natural colors and/or sweeteners.

The preparation of pharmaceutical compositions of this invention can be conducted in accordance with generally accepted procedures for the preparation of pharmaceutical preparations. See, for example, Remington's Pharmaceutical Sciences 18th Edition (1990), E. W. Martin ed., Mack Publishing Co., PA. Depending on the intended use and mode of administration, it may be desirable to process the magnesium-counter ion compound further in the preparation of pharmaceutical compositions. Appropriate processing may include mixing with appropriate non-toxic and non-interfering components, sterilizing, dividing into dose units, and enclosing in a delivery device.

Embodiments of the invention further encompass anhydrous compositions and dosage forms comprising an active ingredient, since water can facilitate the degradation of some compounds. For example, water may be added (e.g., 5%) in the arts as a means of simulating long-term storage in order to determine characteristics such as shelf-life or the stability of formulations over time Anhydrous compositions and dosage forms of the invention can be prepared using anhydrous or low moisture containing ingredients and low moisture or low humidity conditions. Compositions and dosage forms of the invention which contain lactose can be made anhydrous if substantial contact with moisture and/or humidity during manufacturing, packaging, and/or storage is expected. An anhydrous composition may be prepared and stored such that its anhydrous nature is maintained. Accordingly, anhydrous compositions may be packaged using materials known to prevent exposure to water such that they can be included in suitable formulary kits. Examples of suitable packaging include, but are not limited to, hermetically sealed foils, plastic or the like, unit dose containers, blister packs, and strip packs.

An agent described herein can be combined in an intimate admixture with a pharmaceutical carrier according to conventional pharmaceutical compounding techniques. The carrier can take a wide variety of forms depending on the form of preparation desired for administration. In preparing the compositions for an oral dosage form, any of the usual pharmaceutical media can be employed as carriers, such as, for example, water, glycols, oils, alcohols, flavoring agents, preservatives, coloring agents, and the like in the case of oral liquid preparations (such as suspensions, solutions, and elixirs) or aerosols; or carriers such as starches, sugars, micro-crystalline cellulose, diluents, granulating agents, lubricants, binders, and disintegrating agents can be used in the case of oral solid preparations, in some embodiments without employing the use of lactose. For example, suitable carriers include powders, capsules, and tablets, with the solid oral preparations. If desired, tablets can be coated by standard aqueous or nonaqueous techniques.

Some examples of materials which may serve as pharmaceutically acceptable carriers include: (1) sugars, such as lactose, glucose and sucrose; (2) starches, such as corn starch and potato starch; (3) cellulose, and its derivatives, such as sodium carboxymethyl cellulose, ethyl cellulose and cellulose acetate; (4) powdered tragacanth; (5) malt; (6) gelatin; (7) talc; (8) excipients, such as cocoa butter and suppository waxes; (9) oils, such as peanut oil, cottonseed oil, safflower oil, sesame oil, olive oil, corn oil and soybean oil; (10) glycols, such as propylene glycol; (11) polyols, such as glycerin, sorbitol, mannitol and polyethylene glycol; (12) esters, such as ethyl oleate and ethyl laurate; (13) agar; (14) buffering agents, such as magnesium hydroxide and aluminum hydroxide; (15) alginic acid; (16) pyrogen-free water; (17) isotonic saline; (18) Ringer's solution; (19) ethyl alcohol; (20) phosphate buffer solutions; and (21) other non-toxic compatible substances employed in pharmaceutical formulations.

Binders suitable for use in dosage forms include, but are not limited to, corn starch, potato starch, or other starches, gelatin, natural and synthetic gums such as acacia, sodium alginate, alginic acid, other alginates, powdered tragacanth, guar gum, cellulose and its derivatives (e.g., ethyl cellulose, cellulose acetate, carboxymethyl cellulose calcium, sodium carboxymethyl cellulose), polyvinyl pyrrolidone, methyl cellulose, pre-gelatinized starch, hydroxypropyl methyl cellulose, microcrystalline cellulose, and mixtures thereof.

Lubricants which can be used to form compositions and dosage forms of the invention include, but are not limited to, calcium stearate, magnesium stearate, mineral oil, light mineral oil, glycerin, sorbitol, mannitol, polyethylene glycol, other glycols, stearic acid, sodium lauryl sulfate, talc, hydrogenated vegetable oil (e.g., peanut oil, cottonseed oil, sunflower oil, sesame oil, olive oil, corn oil, and soybean oil), zinc stearate, ethyl oleate, ethylaureate, agar, or mixtures thereof. Additional lubricants include, for example, a syloid silica gel, a coagulated aerosol of synthetic silica, or mixtures thereof. A lubricant can optionally be added, in an amount of less than about 1 weight percent of the composition. Lubricants can be also used in conjunction with tissue barriers which include, but are not limited to, polysaccharides, polyglycans, seprafilm, interceed and hyaluronic acid.

Disintegrants may be used in the compositions of the invention to provide tablets that disintegrate when exposed to an aqueous environment. Too much of a disintegrant may produce tablets which may disintegrate in the bottle. Too little may be insufficient for disintegration to occur and may thus alter the rate and extent of release of the active ingredient(s) from the dosage form. Thus, a sufficient amount of disintegrant that is neither too little nor too much to detrimentally alter the release of the active ingredient(s) may be used to form the dosage forms of the compounds disclosed herein. The amount of disintegrant used may vary based upon the type of formulation and mode of administration, and may be readily discernible to those of ordinary skill in the art. About 0.5 to about 15 weight percent of disintegrant, or about 1 to about 5 weight percent of disintegrant, may be used in the pharmaceutical composition. Disintegrants that can be used to form compositions and dosage forms of the invention include, but are not limited to, agar-agar, alginic acid, calcium carbonate, microcrystalline cellulose, croscarmellose sodium, crospovidone, polacrilin potassium, sodium starch glycolate, potato or tapioca starch, other starches, pre-gelatinized starch, other starches, clays, other algins, other celluloses, gums or mixtures thereof.

Examples of suitable fillers for use in the compositions and dosage forms disclosed herein include, but are not limited to, talc, calcium carbonate (e.g., granules or powder), microcrystalline cellulose, powdered cellulose, dextrates, kaolin, mannitol, silicic acid, sorbitol, starch, pre-gelatinized starch, and mixtures thereof.

When aqueous suspensions and/or elixirs are desired for oral administration, the active ingredient therein may be combined with various sweetening or flavoring agents, coloring matter or dyes and, if so desired, emulsifying and/or suspending agents, together with such diluents as water, ethanol, propylene glycol, glycerin and various combinations thereof.

The tablets can be uncoated or coated by known techniques to delay disintegration and absorption in the gastrointestinal tract and thereby provide a sustained action over a longer period. For example, a time delay material such as glyceryl monostearate or glyceryl distearate can be employed. Formulations for oral use can also be presented as hard gelatin capsules wherein the active ingredient is mixed with an inert solid diluent, for example, calcium carbonate, calcium phosphate or kaolin, or as soft gelatin capsules wherein the active ingredient is mixed with water or an oil medium, for example, peanut oil, liquid paraffin or olive oil.

Compositions may include a solubilizer to ensure good solubilization and/or dissolution of the compound of the present invention and to minimize precipitation of the compound of the present invention. This can be useful for compositions for non-oral use, e.g., compositions for injection. A solubilizer may also be added to increase the solubility of the hydrophilic drug and/or other components, such as surfactants, or to maintain the composition as a stable or homogeneous solution or dispersion.

The composition can further include one or more pharmaceutically acceptable additives and excipients. Such additives and excipients include, without limitation, detackifiers, anti-foaming agents, buffering agents, polymers, antioxidants, preservatives, chelating agents, viscomodulators, tonicifiers, flavorants, colorants, odorants, opacifiers, suspending agents, binders, fillers, plasticizers, lubricants, and mixtures thereof. A non-exhaustive list of examples of excipients includes monoglycerides, magnesium stearate, modified food starch, gelatin, microcrystalline cellulose, glycerin, stearic acid, silica, yellow beeswax, lecithin, hydroxypropylcellulose, croscarmellose sodium, and crospovidone.

The compositions described herein can also be formulated as extended-release, sustained-release or time-release such that one or more components are released over time. Delayed release can be achieved by formulating the one or more components in a matrix of a variety of materials or by microencapsulation. The compositions can be formulated to release one or more components over a time period of 4, 6, 8, 12, 16, 20, or 24 hours. The release of the one or more components can be at a constant or changing rate.

Using the controlled release dosage forms provided herein, the one or more cofactors can be released in its dosage form at a slower rate than observed for an immediate release formulation of the same quantity of components. In some embodiments, the rate of change in the biological sample measured as the change in concentration over a defined time period from administration to maximum concentration for an controlled release formulation is less than about 80%, 70%, 60%, 50%, 40%, 30%, 20%, or 10% of the rate of the immediate release formulation. Furthermore, in some embodiments, the rate of change in concentration over time is less than about 80%, 70%, 60%, 50%, 40%, 30%, 20%, or 10% of the rate for the immediate release formulation.

In some embodiments, the rate of change of concentration over time is reduced by increasing the time to maximum concentration in a relatively proportional manner. For example, a two-fold increase in the time to maximum concentration may reduce the rate of change in concentration by approximately a factor of 2. As a result, the one or more cofactors may be provided so that it reaches its maximum concentration at a rate that is significantly reduced over an immediate release dosage form. The compositions of the present invention may be formulated to provide a shift in maximum concentration by 24 hours, 16 hours, 8 hours, 4 hours, 2 hours, or at least 1 hour. The associated reduction in rate of change in concentration may be by a factor of about 0.05, 0.10, 0.25, 0.5 or at least 0.8. In certain embodiments, this is accomplished by releasing less than about 30%, 50%, 75%, 90%, or 95% of the one or more cofactors into the circulation within one hour of such administration.

Optionally, the controlled release formulations exhibit plasma concentration curves having initial (e.g., from 2 hours after administration to 4 hours after administration) slopes less than 75%, 50%, 40%, 30%, 20% or 10% of those for an immediate release formulation of the same dosage of the same cofactor.

In some embodiments, the rate of release of the cofactor as measured in dissolution studies is less than about 80%, 70%, 60% 50%, 40%, 30%, 20%, or 10% of the rate for an immediate release formulation of the same cofactor over the first 1, 2, 4, 6, 8, 10, or 12 hours.

The controlled release formulations provided herein can adopt a variety of formats. In some embodiments, the formulation is in an oral dosage form, including liquid dosage forms (e.g., a suspension or slurry), and oral solid dosage forms (e.g., a tablet or bulk powder), such as, but not limited to those, those described herein.

The controlled release tablet of a formulation disclosed herein can be of a matrix, reservoir or osmotic system. Although any of the three systems is suitable, the latter two systems can have more optimal capacity for encapsulating a relatively large mass, such as for the inclusion of a large amount of a single cofactor, or for inclusion of a plurality of cofactors, depending on the genetic makeup of the individual. In some embodiments, the slow-release tablet is based on a reservoir system, wherein the core containing the one or more cofactors is encapsulated by a porous membrane coating which, upon hydration, permits the one or more cofactors to diffuse through. Because the combined mass of the effective ingredients is generally in gram quantity, an efficient delivery system can provide optimal results.

Thus, tablets or pills can also be coated or otherwise compounded to provide a dosage form affording the advantage of prolonged action. For example, the tablet or pill can comprise an inner dosage an outer dosage component, the latter being in the form of an envelope over the former. The two components can be separated by an enteric layer which serves to resist disintegration in the stomach and permits the inner component to pass intact into the duodenum or to be delayed in release. A variety of materials can be used for such enteric layers or coatings such materials including a number of polymeric acids and mixtures of polymeric acids with such materials as shellac, cetyl alcohol and cellulose acetate. In some embodiments, a formulation comprising a plurality of cofactors may have different cofactors released at different rates or at different times. For example, there can be additional layers of cofactors interspersed with enteric layers.

Methods of making sustained release tablets are known in the art, e.g., see U.S. Patent Publications 2006/051416 and 2007/0065512, or other references disclosed herein. Methods such as described in U.S. Pat. Nos. 4,606,909, 4,769,027, 4,897,268, and 5,395,626 can be used to prepare sustained release formulations of the one or more cofactors determined by the genetic makeup of an individual. In some embodiments, the formulation is prepared using OROS® technology, such as described in U.S. Pat. Nos. 6,919,373, 6,923,800, 6,929,803, and 6,939,556. Other methods, such as described in U.S. Pat. Nos. 6,797,283, 6,764,697, and 6,635,268, can also be used to prepare the formulations disclosed herein.

In some embodiments, the compositions can be formulated in a food composition. For example, the compositions can be a beverage or other liquids, solid food, semi-solid food, with or without a food carrier. For example, the compositions can include a black tea supplemented with any of the compositions described herein. The composition can be a dairy product supplemented any of the compositions described herein. In some embodiments, the compositions can be formulated in a food composition. For example, the compositions can comprise a beverage, solid food, semi-solid food, or a food carrier.

In some embodiments, liquid food carriers, such as in the form of beverages, such as supplemented juices, coffees, teas, sodas, flavored waters, and the like can be used. For example, the beverage can comprise the formulation as well as a liquid component, such as various deodorant or natural carbohydrates present in conventional beverages. Examples of natural carbohydrates include, but are not limited to, monosaccharides such as, glucose and fructose; disaccharides such as maltose and sucrose; conventional sugars, such as dextrin and cyclodextrin; and sugar alcohols, such as xylitol and erythritol. Natural deodorant such as taumatin, stevia extract, levaudioside A, glycyrrhizin, and synthetic deodorant such as saccharin and aspartame may also be used. Agents such as flavoring agents, coloring agents, and others can also be used. For example, pectic acid and the salt thereof, alginic acid and the salt thereof, organic acid, protective colloidal adhesive, pH controlling agent, stabilizer, a preservative, glycerin, alcohol, or carbonizing agents can also be used. Fruit and vegetables can also be used in preparing foods or beverages comprising the formulations discussed herein.

Alternatively, the compositions can be a snack bar supplemented with any of the compositions described herein. For example, the snack bar can be a chocolate bar, a granola bar, or a trail mix bar. In yet another embodiment, the present dietary supplement or food compositions are formulated to have suitable and desirable taste, texture, and viscosity for consumption. Any suitable food carrier can be used in the present food compositions. Food carriers of the present invention include practically any food product. Examples of such food carriers include, but are not limited to food bars (granola bars, protein bars, candy bars, etc.), cereal products (oatmeal, breakfast cereals, granola, etc.), bakery products (bread, donuts, crackers, bagels, pastries, cakes, etc.), beverages (milk-based beverage, sports drinks, fruit juices, alcoholic beverages, bottled waters), pastas, grains (rice, corn, oats, rye, wheat, flour, etc.), egg products, snacks (candy, chips, gum, chocolate, etc.), meats, fruits, and vegetables. In an embodiment, food carriers employed herein can mask the undesirable taste (e.g., bitterness). Where desired, the food composition presented herein exhibit more desirable textures and aromas than that of any of the components described herein. For example, liquid food carriers may be used according to the invention to obtain the present food compositions in the form of beverages, such as supplemented juices, coffees, teas, and the like. In other embodiments, solid food carriers may be used according to the invention to obtain the present food compositions in the form of meal replacements, such as supplemented snack bars, pasta, breads, and the like. In yet other embodiments, semi-solid food carriers may be used according to the invention to obtain the present food compositions in the form of gums, chewy candies or snacks, and the like.

The dosing of the combination compositions can be administered about, less than about, or more than about 1, 2, 3, 4, 5, 6, 7, 8, 9, 10 or more times a daily. A subject can receive dosing for a period of about, less than about, or greater than about 1, 2, 3, 4, 5, 6, 7, 8, 9, 10, 11, 12, 13, 14 or more days, weeks or months. A unit dose can be a fraction of the daily dose, such as the daily dose divided by the number of unit doses to be administered per day. A unit dose can be a fraction of the daily dose that is the daily dose divided by the number of unit doses to be administered per day and further divided by the number of unit doses (e.g. tablets) per administration. The number of unit doses per administration may be about, less than about, or more than about 1, 2, 3, 4, 5, 6, 7, 8, 9, 10, or more. The number of doses per day may be about, less than about, or more than about 1, 2, 3, 4, 5, 6, 7, 8, 9, 10, or more. The number of unit doses per day may be determined by dividing the daily dose by the unit dose, and may be about, less than about, or more than about 1, 2, 3, 4, 5, 6, 7, 8, 9, 10, 11, 12, 13, 14, 15, 6, 17, 18, 19, 20, or more unit doses per day. For example, a unit dose can be about ½, ⅓, ¼, ⅕, ⅙, ⅐, ⅛, ⅑, ⅒. A unit dose can be about one-third of the daily amount and administered to the subject three times daily. A unit dose can be about one-half of the daily amount and administered to the subject twice daily. A unit dose can be about one-fourth of the daily amount with two unit doses administered to the subject twice daily. In some embodiments, a unit dose comprises about, less than about, or more than about 50 mg resveratrol. In some embodiments, a unit dose comprises about, less than about, or more than about 550 mg leucine. In some embodiments, a unit dose comprises about, less than about, or more than about 200 mg of one or more leucine metabolites. In some embodiments, a unit dose (e.g. a unit dose comprising leucine) is administered as two unit doses two times per day. In some embodiments, a unit dose (e.g. a unit dose comprising one or more leucine metabolites, such as HMB) is administered as one unit dose two timer per day. Compositions disclosed herein can further comprise a flavorant and can be a solid, liquid, gel or emulsion.

Exemplary Compositions:

A composition comprising a unit dosage form can be formulated to provide a dosage of a branched chain amino acid in free amino acid form, or a metabolite thereof. The dosage of the branched chain amino acid in free amino acid form or metabolite thereof can be a therapeutic dose or sub-therapeutic dose. For example, a unit dosage composition can comprise about 10-3000 mg (e.g., 50, 100, 200, 250, 300, 400, 500, 750, 1000, 1125, 1500, or 3000 mg) of leucine in free amino acid form, 5-500 mg of HMB (e.g., 5, 10, 20, 50, 100, 200, 300, 400, or 500 mg of HMB), about 20 to about 300 mg of KIC (e.g., 20, 50, 100, 200, 300 mg of KIC), or any combination thereof. In some embodiments, a weight % of the branched amino acid in free amino acid form or metabolite thereof (e.g., leucine, HMB, or KIC) in the composition, excluding excipients (e.g., fillers), is 50-95%.

Any of the above unit dosage compositions can further comprise an additional agent. The additional agent can be a sirtuin pathway activator and/or PDE inhibitor. Exemplary sirtuin pathway activators and PDE inhibitors are described herein. In some embodiments, a weight % of the additional agent in the composition, excluding excipients (e.g., fillers) is 5-50%. In particular embodiments, the additional agent is metformin. The metformin can be present in the unit dosage composition in a therapeutic or sub-therapeutic dose. For example, the unit dosage composition can further comprise about 2.5 to about 500 mg of metformin (e.g., about 2.5, 5, 10, 20, 25, 50, 100, 125, 150, 175, 200, 250, 300, 350, 400, 450, or 500 mg of metformin). In some embodiments, the additional agent is a PDE inhibitor (e.g., a PDE5 inhibitor).

In some embodiments, the additional agent is icariin. The icariin can be present in the unit dosage composition in a therapeutic or sub-therapeutic dose. For example, the unit dosage composition can further comprise about 1 to about 2000 mg of icariin (e.g., about 1, 10, 25, 50, 100, 500, 600, 700, 800, 900, 1000, 1500, or 2000 mg of icariin). In some embodiments, the additional agent is sildenafil. The sildenafil can be present in the unit dosage composition in a therapeutic or sub-therapeutic dose. For example, the unit dosage composition can further comprise about 1 to about 2000 mg of sildenafil (e.g., about 1, 10, 25, 50, 100, 500, 600, 700, 800, 900, 1000, 1500, or 2000 mg of sildenafil).

The unit dosage can comprise about 250 to about 2000 mg of leucine. The unit dosage can comprise about 500 to about 1500 mg of leucine. The unit dosage can comprise about 900 to about 1300 mg of leucine. The unit dosage can further comprise metformin. The weight ratio of metformin relative to leucine can be 0.01-0.6. The weight ratio of metformin relative to leucine can be 0.1-0.5. The weight ratio of metformin relative to leucine can be 0.15-0.3. The unit dosage can optionally further comprise resveratrol. An exemplary unit dosage composition comprises about 125 mg metformin, 1.125 g leucine and, optionally, 50 mg resveratrol. A unit dosage can comprise about 50 mg metformin, 1.125 g leucine and optionally 50 mg resveratrol. A unit dosage can comprise about 250 mg metformin, 1.125 g leucine and optionally 50 mg resveratrol. A unit dosage can comprise about 500 mg metformin, 1.125 g leucine and optionally 50 mg resveratrol. An exemplary formulation of a unit dosage comprising leucine and metformin is shown in Table 1:

TABLE 1

Formulation 1

| Component | Mass (mg) | Wt ratio (relative to Leucine) |
| --- | --- | --- |
| Leucine | 1110 | 1 |
| Metformin | 125 | 0.1126 |

Another exemplary formulation of a unit dosage comprising leucine, metformin, and resveratrol is shown in Table 2:

TABLE 2

Formulation 2

| Component | Mass (mg) | Wt ratio (relative to Leucine) |
| --- | --- | --- |
| Leucine | 1110 | 1 |
| Metformin | 125 | 0.1126 |
| Resveratrol | 50 | 0.045 |

In some embodiments, a unit dosage comprises leucine and icariin. The unit dosage can comprise about 250 to about 2000 mg of leucine. The unit dosage can comprise about 500 to about 1500 mg of leucine. The unit dosage can comprise about 900 to about 1300 mg of leucine. The weight ratio of icariin relative to leucine can be 0.01-0.1. The weight ratio of icariin relative to leucine can be 0.02-0.06. The weight ratio of icariin relative to leucine can be 0.03-0.05. An exemplary formulation of a unit dosage comprising leucine and icariin is shown in Table 3.

TABLE 3

Formulation 3

| Component | Mass (mg) | Wt ratio (relative to Leucine) |
| --- | --- | --- |
| Leucine | 1110 | 1 |
| Icariin | 50 | 0.045 |

In some embodiments, a unit dosage comprises leucine, icariin, and resveratrol. The unit dosage can comprise about 250 to about 2000 mg of leucine. The unit dosage can comprise about 500 to about 1500 mg of leucine. The unit dosage can comprise about 900 to about 1300 mg of leucine. The weight ratio of icariin relative to leucine can be 0.01-0.1. The weight ratio of icariin relative to leucine can be 0.02-0.06. The weight ratio of icariin relative to leucine can be 0.03-0.05. The weight ratio of resveratrol relative to leucine can be 0.01-0.1. The weight ratio of resveratrol relative to leucine can be 0.02-0.06. The weight ratio of resveratrol relative to leucine can be 0.03-0.05. An exemplary formulation of a unit dosage comprising leucine, icariin, and resveratrol is shown in Table 4.

TABLE 4

Formulation 4

| Component | Mass (mg) | Wt ratio (relative to Leucine) |
| --- | --- | --- |
| Leucine | 1110 | 1 |
| Icariin | 50 | 0.045 |
| Resveratrol | 50 | 0.045 |

In some embodiments, a unit dosage comprises leucine, icariin, and metformin. The unit dosage can comprise about 250 to about 2000 mg of leucine. The unit dosage can comprise about 500 to about 1500 mg of leucine. The unit dosage can comprise about 900 to about 1300 mg of leucine. The weight ratio of icariin relative to leucine can be 0.01-0.1. The weight ratio of icariin relative to leucine can be 0.02-0.06. The weight ratio of icariin relative to leucine can be 0.03-0.05. The weight ratio of metformin relative to leucine can be 0.01-0.6. The weight ratio of metformin relative to leucine can be 0.1-0.5. The weight ratio of metformin relative to leucine can be 0.15-0.3. The weight ratio of metformin relative to leucine can be 0.22-0.23. An exemplary formulation of a unit dosage comprising leucine, icariin, and metformin is shown in Table 5.

TABLE 5

Formulation 5

| Component | Mass (mg) | Wt ratio (relative to Leucine) |
| --- | --- | --- |
| Leucine | 1110 | 1 |
| Icariin | 50 | .045 |
| metformin | 250 | .225 |

In some embodiments, a unit dosage comprises leucine, sildenafil, and optionally, resveratrol. The unit dosage can comprise about 250 to about 2000 mg of leucine. The unit dosage can comprise about 500 to about 1500 mg of leucine. The unit dosage can comprise 900-1300 mg of leucine. The weight ratio of resveratrol relative to leucine can be 0.00001-0.05. The weight ratio of resveratrol relative to leucine can be 0.0001-0.03. The weight ratio of resveratrol relative to leucine can be 0.001-0.02. The weight ratio of sildenafil relative to leucine can be 0.00001-0.05. The weight ratio of sildenafil relative to leucine can be 0.0001-0.03. The weight ratio of sildenafil relative to leucine can be 0.001-0.02. The weight ratio of sildenafil relative to leucine can be 0.005-0.015. Two exemplary formulations of a unit dosage comprising leucine and sildenafil, and another unit dosage comprising leucine, resveratrol, and sildenafil are shown in Table 6.

TABLE 6

| Component | Mass (mg) | Wt ratio (relative to Leucine) |
|---|---|---|
| Formulation 6A | | |
| Leucine | 1110 | 1 |
| Sildenafil | 10 | 0.009 |
| Formulation 6B | | |
| Leucine | 1110 | 1 |
| Resveratrol | 10 | 0.009 |
| Sildenafil | 10 | 0.009 |

The unit dosage can comprise about 5-1000 mg of HMB. The unit dosage can comprise about 100-500 mg of HMB. The unit dosage can comprise 150-400 mg of HMB. The unit dosage can comprise 200-300 mg of HMB. The unit dosage can further comprise metformin. The weight ratio of metformin relative to HMB can be 0.01-1. The weight ratio of metformin relative to HMB can be 0.5-0.5. The weight ratio of metformin relative to HMB can be 0.1-0.3. The unit dosage can optionally further comprise resveratrol. An exemplary unit dosage composition comprises about 125 mg metformin, 250 mg HMB and, optionally, 50 mg resveratrol. A unit dosage can comprise about 50 mg metformin, 1250 mg HMB, and optionally 50 mg resveratrol. A unit dosage can comprise about 250 mg metformin, 250 mg HMB and optionally 50 mg resveratrol. A unit dosage can comprise about 500 mg metformin, 500 mg HMB and optionally 50 mg resveratrol. An exemplary formulation of a unit dosage comprising HMB and metformin is shown in Table 7:

TABLE 7

| Component | Mass (mg) | Wt ratio (relative to HMB) |
|---|---|---|
| Formulation 7 | | |
| HMB | 250 | 1 |
| Metformin | 125 | 0.5 |

Another exemplary formulation of a unit dosage comprising HMB, metformin, and resveratrol is shown in Table 8:

TABLE 8

| Component | Mass (mg) | Wt ratio (relative to HMB) |
|---|---|---|
| Formulation 8 | | |
| HMB | 250 | 1 |
| Metformin | 125 | 0.5 |
| Resveratrol | 50 | 0.2 |

In some embodiments, a unit dosage comprises HMB and icariin. The unit dosage can comprise about 5-1000 mg of HMB. The unit dosage can comprise about 100-500 mg of HMB. The unit dosage can comprise 150-400 mg of HMB. The unit dosage can comprise 200-300 mg of HMB. The weight ratio of icariin relative to HMB can be 0.05-0.5. The weight ratio of icariin relative to HMB can be 0.07-0.4. The weight ratio of icariin relative to HMB can be 0.1-0.3. An exemplary formulation of a unit dosage comprising HMB and icariin is shown in Table 9:

TABLE 9

| Component | Mass (mg) | Wt ratio (relative to HMB) |
|---|---|---|
| Formulation 9 | | |
| HMB | 250 | 1 |
| Icariin | 50 | 0.2 |

In some embodiments, a unit dosage comprises HMB, icariin, and resveratrol. The unit dosage can comprise about 5-1000 mg of HMB. The unit dosage can comprise about 100-500 mg of HMB. The unit dosage can comprise about 150-400 mg of HMB. The unit dosage can comprise 200-300 mg of HMB. The weight ratio of icariin relative to HMB can be 0.05-0.5. The weight ratio of icariin relative to HMB can be 0.07-0.4. The weight ratio of icariin relative to HMB can be 0.1-0.3. The weight ratio of resveratrol relative to HMB can be 0.05-0.5. The weight ratio of resveratrol relative to HMB can be 0.07-0.4. The weight ratio of resveratrol relative to HMB can be 0.1-0.3. An exemplary formulation of a unit dosage comprising HMB, icariin, and resveratrol is shown in Table 10.

TABLE 10

| Component | Mass (mg) | Wt ratio (relative to HMB) |
|---|---|---|
| Formulation 10 | | |
| HMB | 250 | 1 |
| Icariin | 50 | 0.2 |
| Resveratrol | 50 | 0.2 |

In some embodiments, a unit dosage comprises HMB, icariin, and metformin. The unit dosage can comprise about 5 to about 1000 mg of HMB. The unit dosage can comprise about 100 to about 500 mg of HMB. The unit dosage can comprise about 150 to about 400 mg of HMB. The unit dosage can comprise about 200 to about 300 mg of HMB. The weight ratio of icariin relative to HMB can be 0.05-0.5. The weight ratio of icariin relative to HMB can be 0.07-0.4.

The weight ratio of icariin relative to HMB can be 0.1-0.3. The weight ratio of metformin relative to HMB can be 0.2-4. The weight ratio of metformin relative to HMB can be 0.5-2. The weight ratio of metformin relative to HMB can be 0.75-1.25. An exemplary formulation of a unit dosage comprising HMB, icariin, and metformin is shown in Table 11.

TABLE 11

Formulation 11

| Component | Mass (mg) | Wt ratio (relative to HMB) |
|---|---|---|
| HMB | 250 | 1 |
| Icariin | 50 | 0.2 |
| Metformin | 250 | 1 |

In some embodiments, a unit dosage comprises HMB and sildenafil. The unit dosage can comprise about 5-1000 mg of HMB. The unit dosage can comprise about 100-500 mg of HMB. The unit dosage can comprise about 150-400 mg of HMB. The unit dosage can comprise 200-300 mg of HMB. The weight ratio of sildenafil relative to HMB can be 0.01-0.1. The weight ratio of sildenafil relative to HMB can be 0.02-0.08. The weight ratio of sildenafil relative to HMB can be 0.03-0.05. An exemplary formulation of a unit dosage comprising HMB and sildenafil is shown in Table 12.

TABLE 12

Formulation 12

| Component | Mass (mg) | Wt ratio (relative to HMB) |
|---|---|---|
| HMB | 250 | 1 |
| Sildenafil | 10 | 0.04 |

In some embodiments, a unit dosage comprises HMB, sildenafil, and resveratrol. The unit dosage can comprise about 5-1000 mg of HMB. The unit dosage can comprise about 100-500 mg of HMB. The unit dosage can comprise about 150-400 mg of HMB. The unit dosage can comprise 200-300 mg of HMB. The weight ratio of sildenafil relative to HMB can be 0.01-0.1. The weight ratio of sildenafil relative to HMB can be 0.02-0.08. The weight ratio of sildenafil relative to HMB can be 0.03-0.05. The weight ratio of resveratrol relative to HMB can be 0.01-0.1. The weight ratio of resveratrol relative to HMB can be 0.02-0.08. The weight ratio of resveratrol relative to HMB can be 0.03-0.05. An exemplary formulation of a unit dosage comprising HMB and sildenafil is shown in Table 13.

TABLE 13

Formulation 13

| Component | Mass (mg) | Wt ratio (relative to HMB) |
|---|---|---|
| HMB | 250 | 1 |
| Sildenafil | 10 | 0.04 |
| Resveratrol | 10 | 0.04 |

The unit dosage can comprise about 20-1000 mg of KIC. The unit dosage can comprise about 100-500 mg of KIC. The unit dosage can comprise 150-400 mg of KIC. The unit dosage can comprise 200-300 mg of KIC. The unit dosage can further comprise metformin. The weight ratio of metformin relative to KIC can be 0.01-1. The weight ratio of metformin relative to KIC can be 0.5-0.5. The weight ratio of metformin relative to KIC can be 0.1-0.3. The unit dosage can optionally further comprise resveratrol. An exemplary unit dosage composition comprises about 50 mg metformin, 250 mg KIC and, optionally, 50 mg resveratrol. A unit dosage can comprise about 100 mg metformin, 1250 mg KIC, and optionally 50 mg resveratrol. A unit dosage can comprise about 250 mg metformin, 250 mg KIC and optionally 50 mg resveratrol. A unit dosage can comprise about 500 mg metformin, 500 mg KIC and optionally 50 mg resveratrol. An exemplary formulation of a unit dosage comprising KIC and metformin is shown in Table 14:

TABLE 14

Formulation 14

| Component | Mass (mg) | Wt ratio (relative to KIC) |
|---|---|---|
| KIC | 250 | 1 |
| Metformin | 50 | 0.2 |

Another exemplary formulation of a unit dosage comprising KIC, metformin, and resveratrol is shown in Table 15:

TABLE 15

Formulation 15

| Component | Mass (mg) | Wt ratio (relative to KIC) |
|---|---|---|
| KIC | 250 | 1 |
| Metformin | 50 | 0.2 |
| Resveratrol | 50 | 0.2 |

In some embodiments, a unit dosage comprises KIC and icariin. The unit dosage can comprise about 20-1000 mg of KIC. The unit dosage can comprise about 100-500 mg of KIC. The unit dosage can comprise 150-400 mg of KIC. The unit dosage can comprise 200-300 mg of KIC. The weight ratio of icariin relative to KIC can be 0.05-0.5. The weight ratio of icariin relative to KIC can be 0.07-0.4. The weight ratio of icariin relative to KIC can be 0.1-0.3. An exemplary formulation of a unit dosage comprising KIC and icariin is shown in Table 16.

TABLE 16

Formulation 16

| Component | Mass (mg) | Wt ratio (relative to KIC) |
|---|---|---|
| KIC | 250 | 1 |
| Icariin | 50 | 0.2 |

In some embodiments, a unit dosage comprises KIC, icariin, and resveratrol. The unit dosage can comprise about 20-1000 mg of KIC. The unit dosage can comprise about 100-500 mg of KIC. The unit dosage can comprise about 150-400 mg of KIC. The unit dosage can comprise 200-300 mg of KIC. The weight ratio of icariin relative to KIC can be 0.05-0.5. The weight ratio of icariin relative to KIC can be 0.07-0.4. The weight ratio of icariin relative to KIC can be 0.1-0.3. The weight ratio of resveratrol relative to KIC can be 0.05-0.5. The weight ratio of resveratrol relative to KIC can be 0.07-0.4. The weight ratio of resveratrol relative to KIC can be 0.1-0.3. An exemplary formulation of a unit dosage comprising KIC, icariin, and resveratrol is shown in Table 17.

TABLE 17

Formulation 17

| Component | Mass (mg) | Wt ratio (relative to KIC) |
|---|---|---|
| KIC | 250 | 1 |
| Icariin | 50 | 0.2 |
| Resveratrol | 50 | 0.2 |

In some embodiments, a unit dosage comprises KIC, icariin, and metformin. The unit dosage can comprise about 50 to about 1000 mg of KIC. The unit dosage can comprise about 100 to about 500 mg of KIC. The unit dosage can comprise about 150 to about 400 mg of KIC. The unit dosage can comprise about 200 to about 300 mg of KIC. The weight ratio of icariin relative to KIC can be 0.05-0.5. The weight ratio of icariin relative to KIC can be 0.07-0.4. The weight ratio of icariin relative to KIC can be 0.1-0.3. The weight ratio of metformin relative to KIC can be 0.2-4. The weight ratio of metformin relative to KIC can be 0.5-2. The weight ratio of metformin relative to KIC can be 0.75-1.25. An exemplary formulation of a unit dosage comprising KIC, icariin, and metformin is shown in Table 18.

TABLE 18

Formulation 18

| Component | Mass (mg) | Wt ratio (relative to KIC) |
|---|---|---|
| KIC | 250 | 1 |
| Icariin | 50 | 0.2 |
| Metformin | 250 | 1 |

In some embodiments, a unit dosage comprises KIC and sildenafil. The unit dosage can comprise about 20-1000 mg of KIC. The unit dosage can comprise about 100-500 mg of KIC. The unit dosage can comprise about 150-400 mg of KIC. The unit dosage can comprise 200-300 mg of KIC. The weight ratio of sildenafil relative to KIC can be 0.01-0.1. The weight ratio of sildenafil relative to KIC can be 0.02-0.08. The weight ratio of sildenafil relative to KIC can be 0.03-0.05. An exemplary formulation of a unit dosage comprising KIC and sildenafil is shown in Table 19.

TABLE 19

Formulation 19

| Component | Mass (mg) | Wt ratio (relative to KIC) |
|---|---|---|
| KIC | 250 | 1 |
| Sildenafil | 10 | 0.04 |

In some embodiments, a unit dosage comprises KIC, sildenafil, and resveratrol. The unit dosage can comprise about 20-1000 mg of KIC. The unit dosage can comprise about 100-500 mg of KIC. The unit dosage can comprise about 150-400 mg of KIC. The unit dosage can comprise 200-300 mg of KIC. The weight ratio of sildenafil relative to KIC can be 0.01-0.1. The weight ratio of sildenafil relative to KIC can be 0.02-0.08. The weight ratio of sildenafil relative to KIC can be 0.03-0.05. The weight ratio of resveratrol relative to KIC can be 0.01-0.1. The weight ratio of resveratrol relative to KIC can be 0.02-0.08. The weight ratio of resveratrol relative to KIC can be 0.03-0.05. An exemplary formulation of a unit dosage comprising KIC and sildenafil is shown in Table 20.

TABLE 20

Formulation 20

| Component | Mass (mg) | Wt ratio (relative to KIC) |
|---|---|---|
| KIC | 250 | 1 |
| Sildenafil | 10 | 0.04 |
| Resveratrol | 10 | 0.04 |

In some embodiments, a unit dosage comprises leucine, metformin, and sildenafil. The unit dosage can comprise about 250 to about 2000 mg of leucine. The unit dosage can comprise about 500 to about 1500 mg of leucine. The unit dosage can comprise 900-1300 mg of leucine. The weight ratio of metformin relative to leucine can be 0.15-0.3. The weight ratio of metformin relative to leucine can be 0.22-0.23. The weight ratio of sildenafil relative to leucine can be 0.00001-0.05. The weight ratio of sildenafil relative to leucine can be 0.0001-0.03. The weight ratio of sildenafil relative to leucine can be 0.001-0.02. The weight ratio of sildenafil relative to leucine can be 0.005-0.015. An exemplary formulation of a unit dosage comprising leucine, metformin and sildenafil is shown in Table 21.

TABLE 21

Formulation 21

| Component | Mass (mg) | Wt ratio (relative to Leucine) |
|---|---|---|
| Leucine | 1110 | 1 |
| Metformin | 250 | 0.225 |
| Sildenafil | 10 | 0.009 |

In some embodiments, the molar ratio of (a) branched chain amino acids and/or metabolites thereof to (b) a selective PDE inhibitor about or greater than about 20, 25, 30, 35, 40, 45, 50, 55, 60, 65, 70, 75, 80, 85, 90, 100, 120, or 150. In other embodiments, the molar ratio of one or more branched chain amino acids and/or metabolites thereof to a selective PDE inhibitor contained in the subject compositions is about or greater than about 20, 30, 40, 50, 60, 70, 80, 90, 95, 90, 95, 100, 105, 110, 120, 130, 140, 150, 160, 170, 180, 190, 200, 220, 250, 300, 350, 400, or 500. In some embodiments, the molar ratio of component (a) to (b) in said composition is greater than about 20, 40, 60, 80, 100, 120, or 150. In some embodiments, the molar ratio of component (a) to (b) in said composition is greater than about 80, 100, 120, or 150. In some embodiments, the molar ratio of component (a) to (b) in said composition is greater than about 80, 100, 120, or 150. In some embodiments, the molar ratio of component (a) to (b) in said composition is greater than about 200, 250, or 300. In some embodiments, the molar ratio of component (a) to (b) in said composition is greater than about 40, 150, 250, or 500.

In some embodiments, the dosing of leucine, any metabolites of leucine, the PDE inhibitor (such as a PDE 5 inhibitor like sildenafil) can be designed to achieve a specified physiological concentration or circulating level of leucine, metabolites of leucine and/or a PDE 5 inhibitor. The physiological concentration can be a circulating level as measured in the blood stream of a subject. The subject can be a human or an animal. A selected dosing can be altered based on the characteristics of the subject, such as weight, rate of energy metabolism, genetics, ethnicity, height, or any other characteristic. The amount of leucine in a unit dose can be such that the circulating level of leucine in a subject is about or greater than about 0.25 mM, 0.5 mM, 0.75 mM, or 1 mM. A dosing of about 1,125 mg leucine (e.g., free leucine), can achieve a circulating level of leucine in a subject that is about 0.5 mM. A dosing of about 300 mg leucine (e.g., free leucine), can achieve a circulating level of leucine in a subject that is about 0.25 mM. The dosing of about sildenafil can achieve a circulating concentration of about or less than about 0.1, 0.5, 1, 2, 5, or 10 nM. In some embodiments, the target or achieved circulating concentration of sildenafil is less than about 1 nM. A unit dose of about 20 mg of sildenafil can achieve a circulating concentration of about 100 nM of sildenafil. A unit dose of about 0.2 mg of sildenafil can achieve a circulating concentration of about 1 nM of sildenafil. The dosing of about icariin can achieve a circulating concentration of about or less than about 0.1, 0.5, 1, 2, 5, or 10 nM. In some embodiments, the target or achieved circulating concentration of icariin is less than about 1 nM. A unit dose of about 20 mg of icariin can achieve a circulating concentration of about 100 nM of icariin. A unit dose of about 0.1 mg of icariin can achieve a circulating concentration of about 1 nM of icariin.

In some embodiments, the molar or mass ratios are circulating molar or mass ratios achieved after administration one or more compositions to a subject. The compositions can be a combination composition described herein. The molar ratio of a combination composition in a dosing form can be adjusted to achieve a desired circulating molar ratio. The molar ratio can be adjusted to account for the bioavailability, the uptake, and the metabolic processing of the one or more components of a combination composition. For example, if the bioavailability of a component is low, then the molar amount of a that component can be increased relative to other components in the combination composition. In some embodiments, the circulating molar or mass ratio is achieved within about 0.1, 0.5, 0.75, 1, 3, 5, or 10, 12, 24, or 48 hours after administration. The circulating molar or mass ratio can be maintained for a time period of about or greater than about 0.1, 1, 2, 5, 10, 12, 18, 24, 36, 48, 72, or 96 hours.

In some embodiments, the circulating molar ratio of leucine to sildenafil is about or greater than about 100,000, 250,000, 500,000, 750,000 or more. In some embodiments, the circulating molar ratio of HMB to sildenafil is about or greater than about 1,000, 2,500, 5,000, 7,500 or more. In some embodiments, the circulating molar ratio of resveratrol to sildenafil is about or greater than about 50, 100, 200, 400, 800 or more.

The compositions can be administered to a subject such that the subject is administered a selected total daily dose of the composition. The total daily dose can be determined by the sum of doses administered over a 24 hour period. The total daily dose of the composition can include about 0.05, 0.1, 0.5, 1, 2, 5, 10, 20, 40, 60, 80, or 100 mg of sildenafil. The total daily dose of the composition can include about 1, 10, 20, 50, 100, 150, 300, 400, 500, 750, 1000, 1500, or 2000 mg of icariin. The total daily dose of the composition can include about 1, 10, 20, 50, 100, 150, 200, 250, 300, 350, 400, 450, 500, 550, 600, 650, 700, 750, 800, 900, or 1000 mg of metformin. The total daily dose of the composition can include at least about 250, 500, 750, 1000, 1125, 2000, 2250 mg, 2550 mg or more of a branched chain amino acid or metabolite thereof. The branched chain amino acid can be leucine, HMB, or any other branched chain amino acid described herein.

In some embodiments, a selected dose of a composition can be administered to a subject such that the subject achieves a desired circulating level of the composition. The desired circulating level of the leucine can be at least about 0.25, 0.5, 0.75, 1 mM or more of leucine. The desired circulating level of the sildenafil can be about 0.1, 0.5, 1, 2, 5, 10 nM or more of sildenafil. The desired circulating level of the icariin can be about 0.1, 0.5, 1, 2, 5, 10 nM or more of icariin. The desired circulating level of the metformin can be about 1, 2, 4, 5 µM or more of metformin. The desired circulating level of the rosiglitazone can be about 1, 10, 25, 50, 100, 400 nM or more of rosiglitazone. The desired circulating level of the pioglitazone can be about 0.25, 0.50, 1.0, 2.0 µM or more of pioglitazone. The selected dose can be chosen based on the characteristics of the subject, such as weight, height, ethnicity, or genetics.

EXAMPLES

Figure 2:
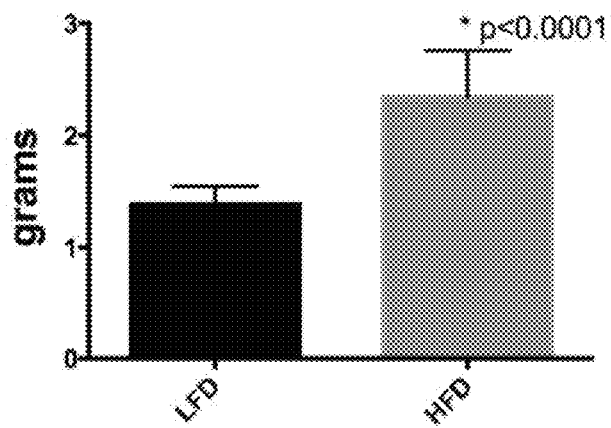
FIG. 2 depicts effects of chronic high fat diet on liver mass in C57Bl/6 mice.
Figure 3:
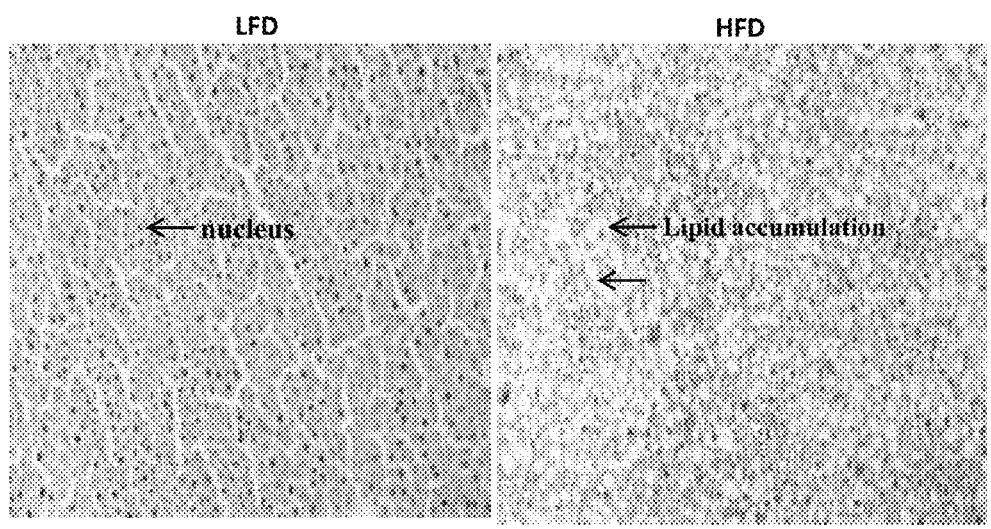
FIG. 3 depicts effects of chronic high fat diet on hepatic lipid accumulation in C57Bl/6 mice.

Example 1: Effects of Chronic High Fat Diet on Liver Mass and Hepatic Lipid Accumulation Chronic high fat diet was used in C57Bl/6 mice as an experimental model of hepatic steatosis. Male C57/BL6 mice were either maintained on standard low-fat diet (control; LFD; 10% energy from fat) or placed on a high fat (HFD; 60% energy from fat, Research Diets #D12492, Research Diets, Inc, New Brunswick, N.J.) at six weeks of age to induce obesity and fatty infiltration of the liver. Following six weeks on the high fat diet, there was a significant, substantial increase in liver mass (p<0.0001, FIG. 2). This increase in liver mass was accompanied by a marked increase in hepatic lipid infiltration, as shown histologically in FIG. 3. Animals fed with LFD have normal cellular structure in liver cells. Black dots denote cell nuclei. Typically, cell nuclei can be illustrated by staining with hematoxylin, methylene blue, nile blue, or neutral/Toluylene red. By contrast, animals fed with HFD have increased liver mass and increased hepatic lipid infiltration are shown in the HFD panel. Numerous lipid vesicles are found in liver cells in the HFD panel, arrows point to exemplary lipid vesicles. Liver cells in the HFD panel also have disrupted cellular structure, as shown by the distribution of nuclei. These results indicate that chronic HFD induces hepatic steatosis in mice. Animals were then randomized to treatments for an additional six weeks, with 10 animals per group, as specified in the following examples. Data for all examples were analyzed via one-way analysis of variance; when ANOVA showed significant differences, means were separated via Tukey's multiple comparison test (Graphpad Prism, Version 6.0).

Example 2: Effect of Various Combinations of Metformin, Resveratrol and Leucine on Liver Mass and Hepatic Steatosis In this study, the effects of metformin alone (therapeutic dose), subtherapeutic metformin alone, subtherapeutic leucine, and various combinations of leucine, metformin, and resveratrol on liver weight and hepatic lipid accumulation were assessed. The 1.5 g/kg diet of metformin corresponds to a therapeutically effective dose of metformin in humans. The remaining metformin doses (0.05-0.5 g/kg) represent sub-therapeutic doses that exert no independent effects. Likewise, the 24 g/kg dose of leucine represents a sub-therapeutic dose that was predicted to exert no significant independent effects on liver mass or hepatic steatosis. Following induction of hepatic steatosis as described in Example 1, animals were treated according to the following treatment groups as depicted in Table 21:

TABLE 21

Example 2 Treatment Groups

Low fat diet (LFD) control
High fat diet (HFD) control
HFD + therapeutic metformin alone (1.5 g/kg diet; calculated human equivalent dose, 1,500 mg/day)
HFD + leucine alone (24 g leucine/kg diet)
HFD + leucine (24 g/kg diet) + resveratrol (12.5 mg/kg diet)
HFD + Leucine (24 g/kg diet) + resveratrol (12.5 mg/kg diet) + metformin (0.05 g/kg diet; calculated human equivalent dose, 50 mg/day)
HFD + Leucine (24 g/kg diet) + resveratrol (12.5 mg/kg diet) + metformin (0.15 g/kg diet; calculated human equivalent dose, 125 mg/day)
HFD + Leucine (24 g/kg diet) + resveratrol (12.5 mg/kg diet) + metformin (0.25 g/kg diet; calculated human equivalent dose, 250 mg/day)

Figure 4:
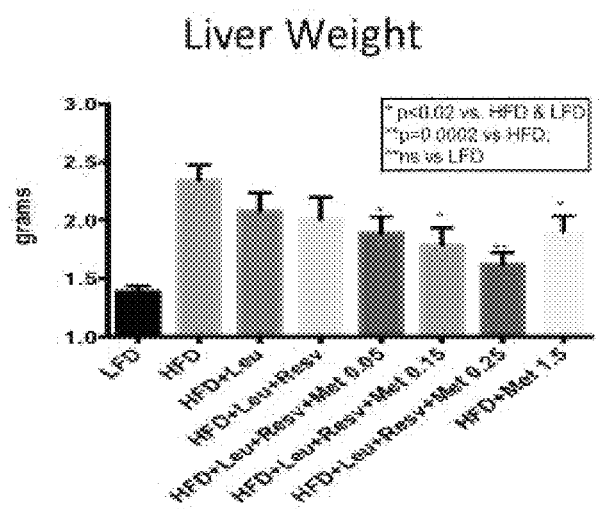
FIG. 4 depicts effects of administration of leucine, administration of therapeutic amounts of metformin, and administration of various combinations of low dose leucine, resveratrol, and metformin on liver mass following a chronic high fat diet.
Figure 5:
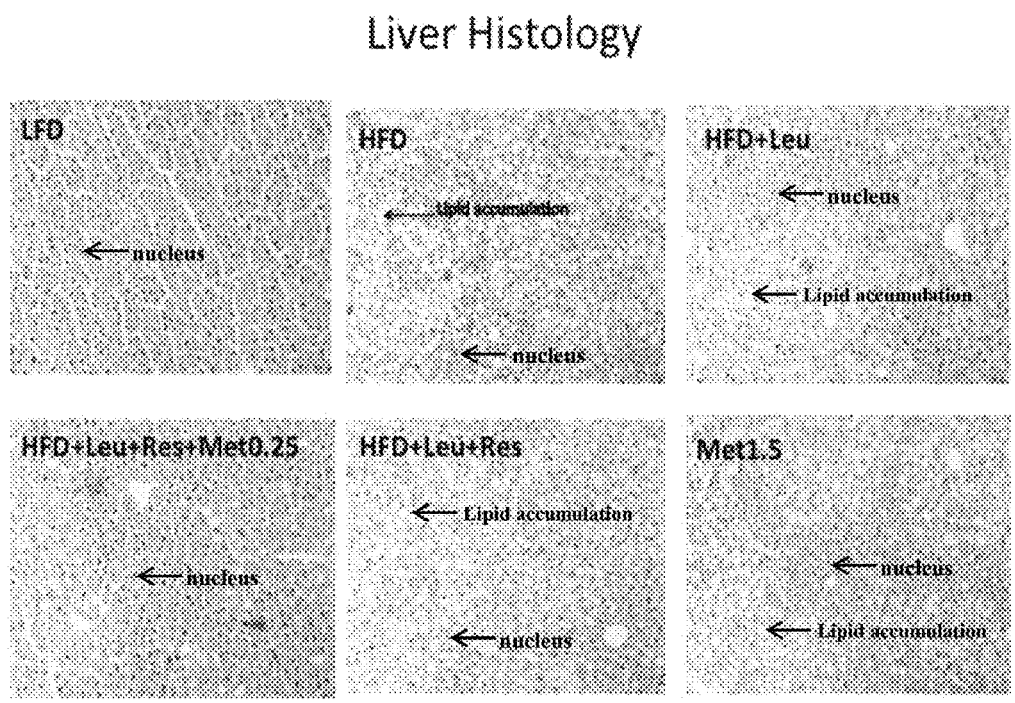
FIG. 5 depicts effects of administration of leucine, administration of therapeutic amounts of metformin, and administration of various combinations of low dose leucine, resveratrol, and metformin on hepatic lipid accumulation following a chronic high fat diet.

FIGS. 4 and 5 depict results of the above study. High fat diet increased liver weight by approximately 70% (FIG. 4). Administration of therapeutic dosages of metformin partially reverse the effect of high fat diet on liver weight back to control levels ($p<0.02$ vs. HFD and LFD, FIG. 4). Administration of sub-therapeutic leucine alone had no significant effect on liver weight (FIG. 4). Likewise, administration of sub-therapeutic leucine+sub-therapeutic resveratrol had no significant effect on liver weight (FIG. 4). Surprisingly, combining subtherapeutic leucine, subtherapeutic resveratrol, and sub-therapeutic metformin (0.15 g/kg) significantly reduced the effect of high fat diet on liver weight ($p<0.02$ vs. HFD and LFD, FIG. 4). Furthermore, combining sub-therapeutic leucine, sub-therapeutic resveratrol and 0.25 g/kg metformin effected a complete reversal of the effects of high fat diet on liver weight back to control levels ($p<0.0002$ vs. HFD; n.s. vs. LFD, FIG. 4).

Histological analysis reveals that animals fed with low fat diet (LFD) have normal cellular structure and show no detectable lipid vesicles. By contrast, animals fed with high fat diet (HFD) induced significant hepatic steatosis (FIG. 5). Administration of therapeutic dosages of metformin effected a partial reversal of the effects of HFD on hepatic steatosis (FIG. 5). The cells appear to have reduced hepatic accumulation and reduced lipid vesicles. Administration of leucine alone nor leucine+resveratrol did not appear to significantly reduce hepatic steatosis, as shown by the appearance lipid vesicles and lipid accumulation (FIG. 5). However, combination therapy with sub-therapeutic dosages of leucine, resveratrol, and metformin appeared to reverse hepatic steatosis, as shown by decreased hepatic lipid accumulation and decreased lipid vesicles (FIG. 5). Cells also appear to show comparable cellular structure to cells in the LFD panel.

Example 3: Effect of Various Combinations of Metformin and Leucine on Liver Mass and Hepatic Steatosis In this study, the effects of metformin alone (therapeutic dose) vs. combination therapy with sub-therapeutic amounts of metformin and leucine on liver weight and hepatic lipid accumulation were assessed. Following induction of hepatic steatosis as described in Example 1, animals were treated for six weeks according to the following treatment groups as depicted in Table 22:

TABLE 22

Example 3 Treatment Groups
Treatment Group

Low fat diet (LFD) control
High fat diet (HFD) control
HFD + therapeutic metformin alone (1.5 g metformin/kg diet; calculated human equivalent dose, 1,500 mg/day)
HFD + Leucine (24 g/kg diet; calculated human equivalent dose, exclusive of diet, 2-3 g/day) + metformin (0.15 g/kg diet metformin; calculated human equivalent dose, 125 mg/day of metformin)
HFD + Leucine (24 g/kg diet; calculated human equivalent dose, exclusive of diet, 2-3 g/day) + metformin (0.25 g/kg diet; calculated human equivalent dose, 250 mg/day)
HFD + Leucine (24 g/kg diet; calculated human equivalent dose, exclusive of diet, 2-3 g/day) + metformin (0.50 g/kg diet; calculated human equivalent dose, 500 mg/day)

Figure 6:
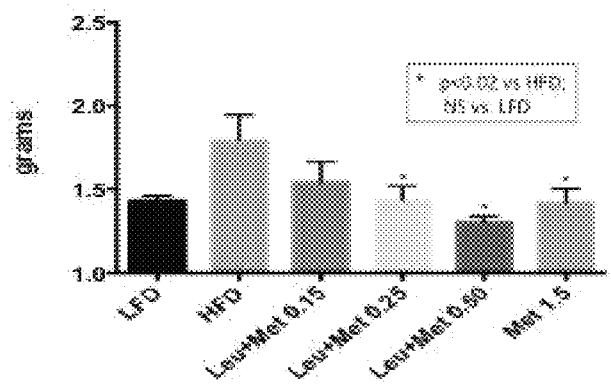
FIG. 6 depicts effects of administration of leucine, administration of therapeutic amounts of metformin, and administration of low dose leucine and metformin on liver mass following a chronic high fat diet.
Figure 7:
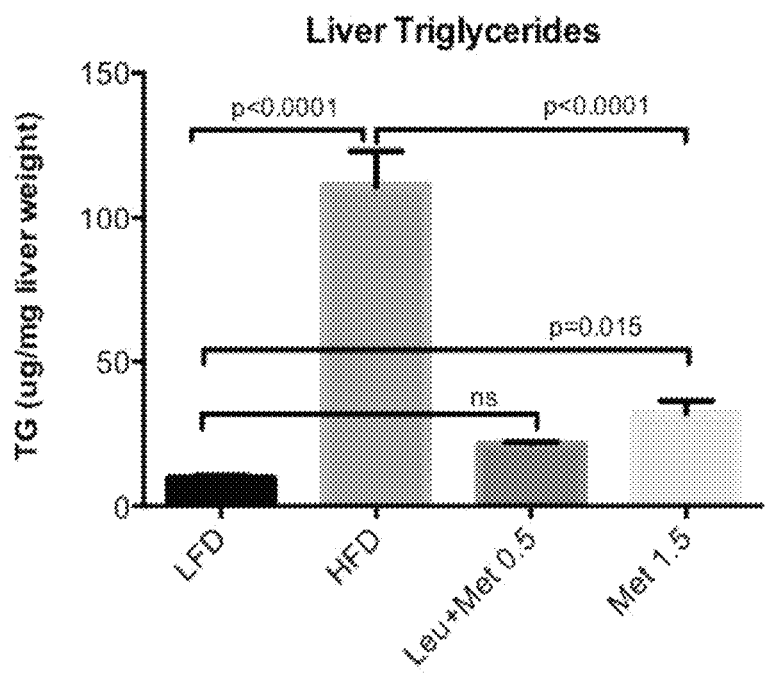
FIG. 7 depicts effects of administration of leucine, administration of therapeutic amounts of metformin, and administration of low dose leucine and metformin on liver triglyceride content following a chronic high fat diet.
Figure 8:
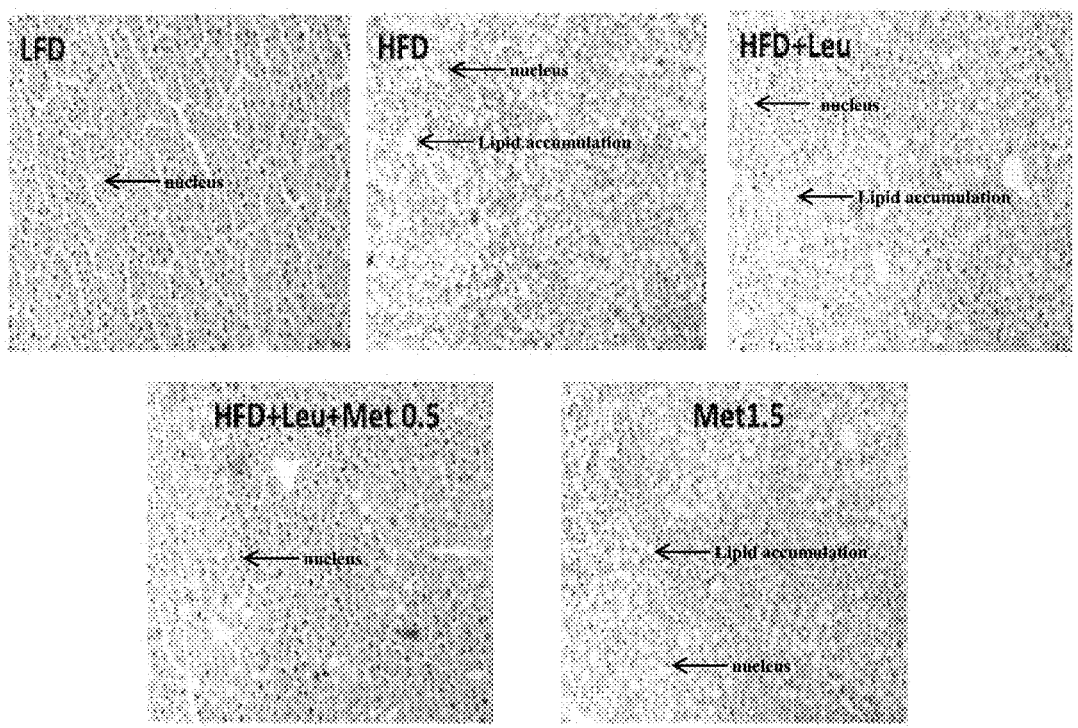
FIG. 8 depicts effects of administration of leucine, administration of therapeutic amounts of metformin, and administration of low dose leucine and metformin on histological evidence of hepatic lipid accumulation following a chronic high fat diet.

FIGS. 6-8 depict the primary results of the above study. High fat diet increased liver weight by approximately 30% (FIG. 6) and liver triglyceride by approximately five-fold (FIG. 7). Administration of therapeutic dosages of metformin reversed the effect of high fat diet on liver weight back to control levels ($p<0.02$ vs. HFD, n.s. compared to LFD, FIG. 6). Surprisingly, combining sub-therapeutic dosages of leucine with sub-therapeutic dosages of metformin (0.25 and 0.5 g/kg) also reversed the effect of high fat diet on liver weight back to control levels ($p<0.02$ vs. HFD, n.s. compared to LFD, FIG. 6). Administration of therapeutic dosages of metformin partially reversed the effect of high fat diet on liver triglycerides (FIG. 7), but the sub-therapeutic dosage of metformin (0.5 g/kg) combined with leucine was significantly more effective and fully reversed the effects of the high fat diet on liver triglycerides (FIG. 7).

Histological analysis reveals that control animals fed with low fat diet (LFD) have no detectable lipid accumulation in liver cells. By contrast, animals fed with high fat diet (HFD) induced significant hepatic steatosis (FIG. 8). Administration of therapeutic dosages of leucine partially reversed hepatic steatosis, as shown by reduced lipid accumulation and lipid vesicles in liver cells. Administration of therapeutic dosages of metformin partially reversed hepatic steatosis, as shown by reduced lipid accumulation and lipid vesicles in liver cells (FIG. 8). Combining subtherapeutic dosage of leucine with metformin (0.5 g/kg) also reversed hepatic steatosis (FIG. 8). The number of lipid vesicles and lipid accumulation in liver cells appeared to be greatly reduced in animals treated with leucine and metformin combination. The cellular structure also appeared to be comparable to the cells in the LFD panel.

Figure 9:
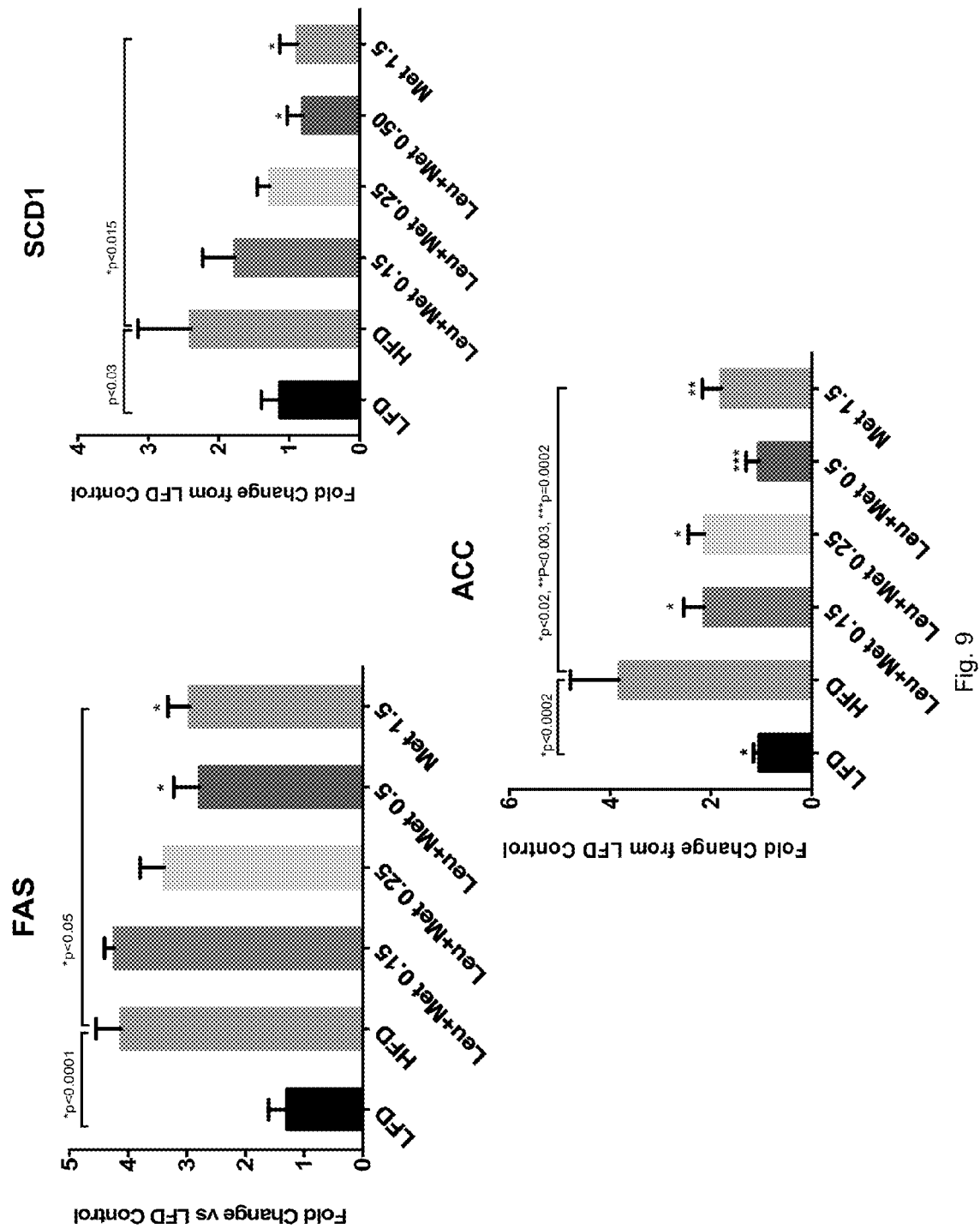
FIG. 9 depicts effects of administration of leucine, administration of therapeutic amounts of metformin, and administration of low dose leucine and metformin on hepatic expression of lipogenic genes.

The high fat diet markedly increased liver expression of lipogenic genes, including acetyl-CoA carboxylase (ACC), stearoyl-CoA desaturase 1 (SCD1) and fatty acid synthase (FAS)(FIG. 9), while adding leucine with low-dos metformin resulted in significant dose-dependent reductions in lipogenic gene expression (FIG. 9). Notably, the combination of metformin (0.5 g/kg) and leucine exerted a significantly greater effect on reducing ACC than did the therapeutic dose of metformin (FIG. 9).

Figure 10:
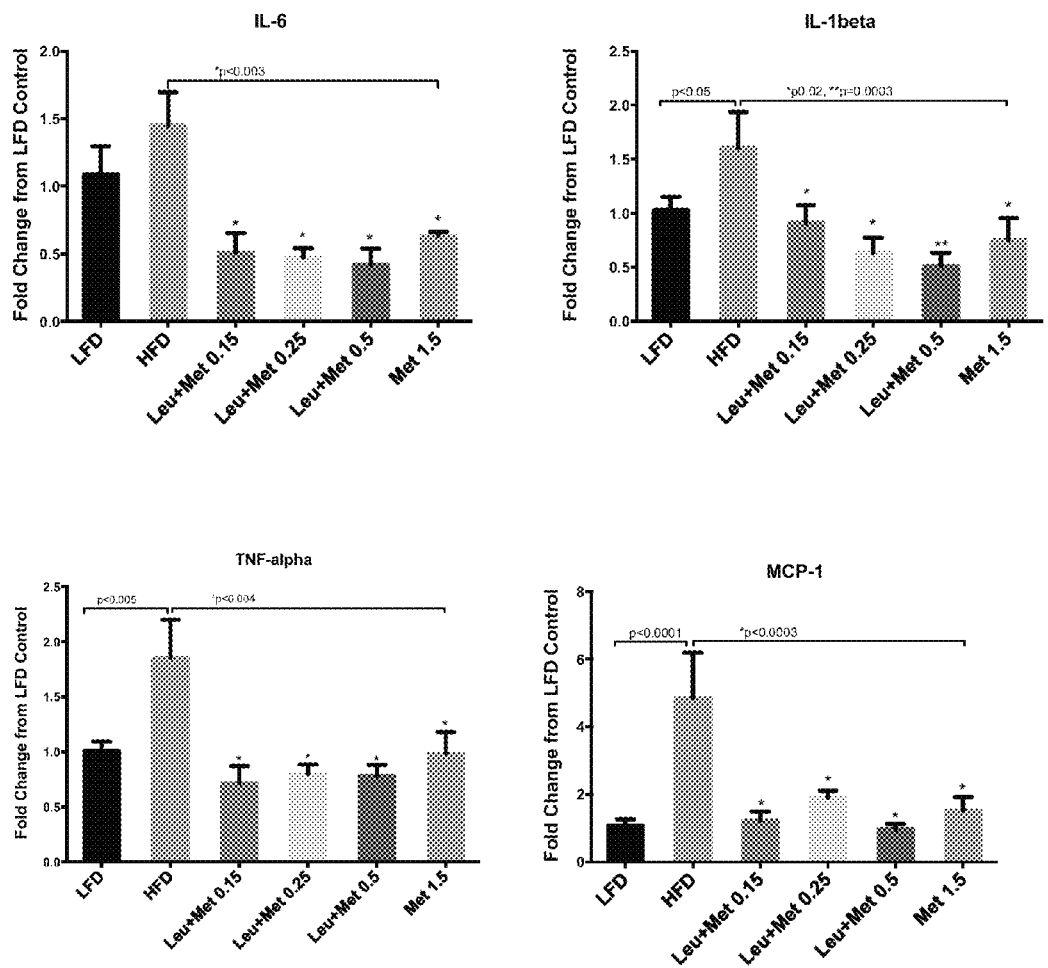
FIG. 10 depicts effects of administration of leucine, administration of therapeutic amounts of metformin, and administration of low dose leucine and metformin on hepatic expression of inflammatory genes.

The expression of hepatic inflammatory genes interleukin (IL)-6, IL-1β, tumor necrosis factor (TNF)-α and monocyte chemotactic protein (MCP)-1 were significantly increased by the high fat diet and reduced by the leucine-metformin combinations, and the low-dose combinations exerted significantly greater effects on IL1β and MCP-1 than did the therapeutic dose of metformin (FIG. 10).

Example 4: Effect of Various Combinations of Metformin and HMB on Liver Mass and Hepatic Steatosis In this study, the effects of metformin alone (therapeutic dose) vs. combination therapy with sub-therapeutic amounts of metformin and HMB on liver weight and hepatic lipid accumulation were assessed. Following induction of hepatic steatosis as described in Example 1, animals were treated for six weeks according to the following treatment groups as depicted in Table 23:

TABLE 23

Example 4 treatment groups

Low fat diet (LFD) control
High fat diet (HFD) control
HFD + therapeutic metformin alone (1.5 g metformin/kg diet; calculated human equivalent dose, 1,500 mg/day)
HFD + HMB (CaHMB, 2 g/kg diet; calculated human equivalent dose, ~500 mg/day) + metformin (0.15 g/kg diet)
HMB + metformin (0.25 g/kg diet)
HMB + metformin (0.50 g/kg diet)

Figure 11:
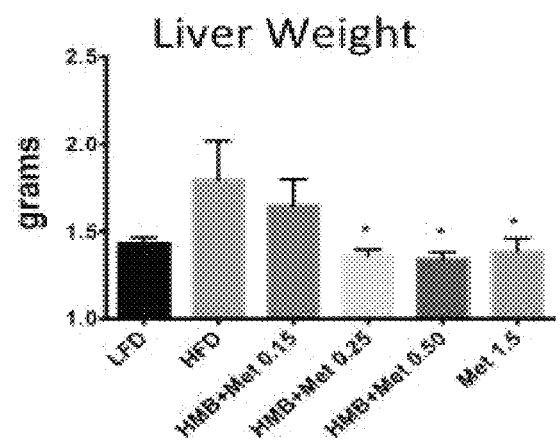
FIG. 11 depicts effects of administration of therapeutic amounts of metformin, and administration of low dose metformin and HMB on liver mass following a chronic high fat diet.
Figure 12:
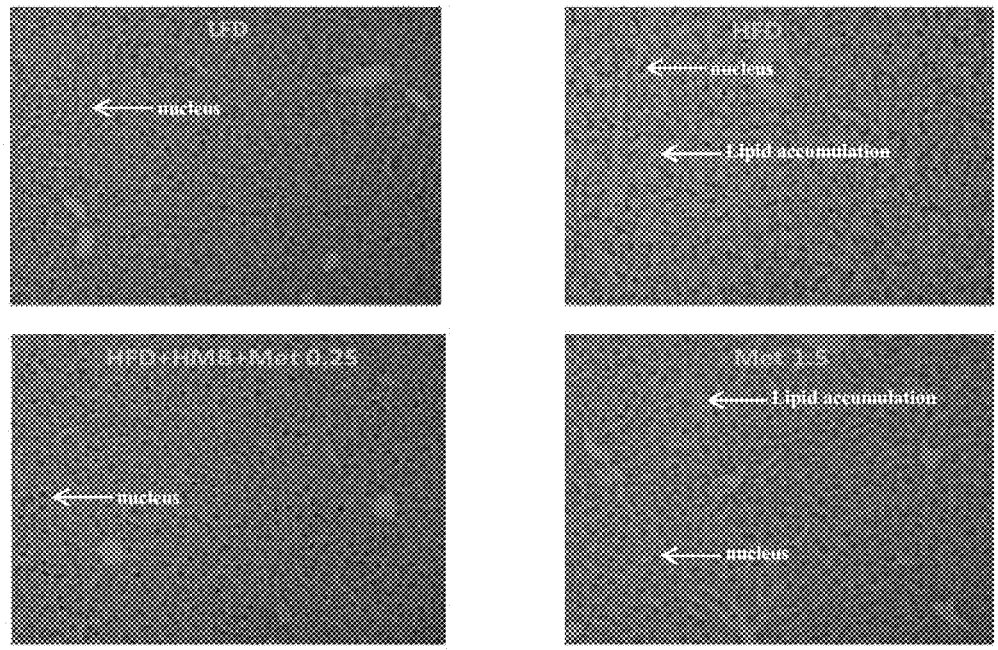
FIG. 12 depicts effects of administration of therapeutic amounts of metformin, and administration of low dose metformin and HMB on hepatic lipid accumulation following a chronic high fat diet.

FIGS. 11 and 12 depict results of the above study. High fat diet increased liver weight by approximately 25% (FIG. 11). Administration of therapeutic dosages of metformin reversed the effect of high fat diet on liver weight back to control levels (p<0.03, FIG. 8). Surprisingly, combining sub-therapeutic dosages of HMB with sub-therapeutic dosages of metformin (0.25 and 0.5 g/kg) also reversed the effect of high fat diet on liver weight back to control levels p<0.03, FIG. 11).

Histological analysis revealed that control animals fed with low fat diet (LFD) have normal cellular structure and no detectable lipid accumulation. By contrast, animals fed with high fat diet (HFD) induced significant hepatic steatosis, as shown by lipid accumulation and the appearance of numerous lipid vesicles in liver cells (FIG. 12). Administration of therapeutic dosages of metformin partially reversed hepatic steatosis, as shown by reduced lipid accumulation and reduced lipid vesicles in liver cells (FIG. 12). Combining subtherapeutic dosage of HMB with metformin (0.25 g/kg) also reversed hepatic steatosis (FIG. 12). The liver cells appear to have comparable cellular structure with liver cells in the LFD panel.

Example 5: Effect of Various Combinations of a PDE5-Specific Inhibitor and Leucine on Liver Mass and Hepatic Steatosis In this study, the effects of leucine alone vs. combination therapy with leucine and the PDE5-specific inhibitor icariin on liver weight and hepatic lipid accumulation were assessed. Previous published studies of icariin have demonstrated no effect of 25 mg icariin/kg diet; corresponding to 4 mg/kg body weight/day) on liver mass or hepatic lipid accumulation. Following induction of hepatic steatosis as described in Example 1, animals were treated for six weeks according to the following treatment groups as depicted in Table 24:

TABLE 24

Example 5 treatment groups

Low fat diet (LFD) control
High fat diet (HFD) control
HFD + leucine alone (24 g/kg diet; calculated human equivalent dose, exclusive of diet, 2-3 g/day)
HFD + leucine (24 g/kg diet; calculated human equivalent dose, exclusive of diet, 2-3 g/day) + icariin (25 mg/kg diet; calculated human equivalent dose, ~10 mg)

Figure 13:
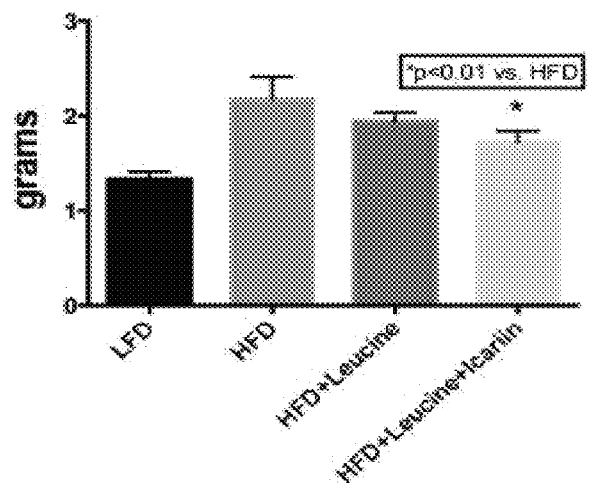
FIG. 13 depicts effects of administration of low dose leucine and icariin on liver mass following a chronic high fat diet.

FIGS. 10 and 11 depict results of the above study. High fat diet increased liver weight by approximately 75% (FIG. 13). Administration of leucine alone had no effect on liver weight, FIG. 10). Surprisingly, combining sub-therapeutic dosages of leucine with sub-therapeutic dosages of icariin (25 mg/kg) significantly reduced the effect of high fat diet on liver weight (p<0.01 vs. HFD, FIG. 13).

Figure 14:
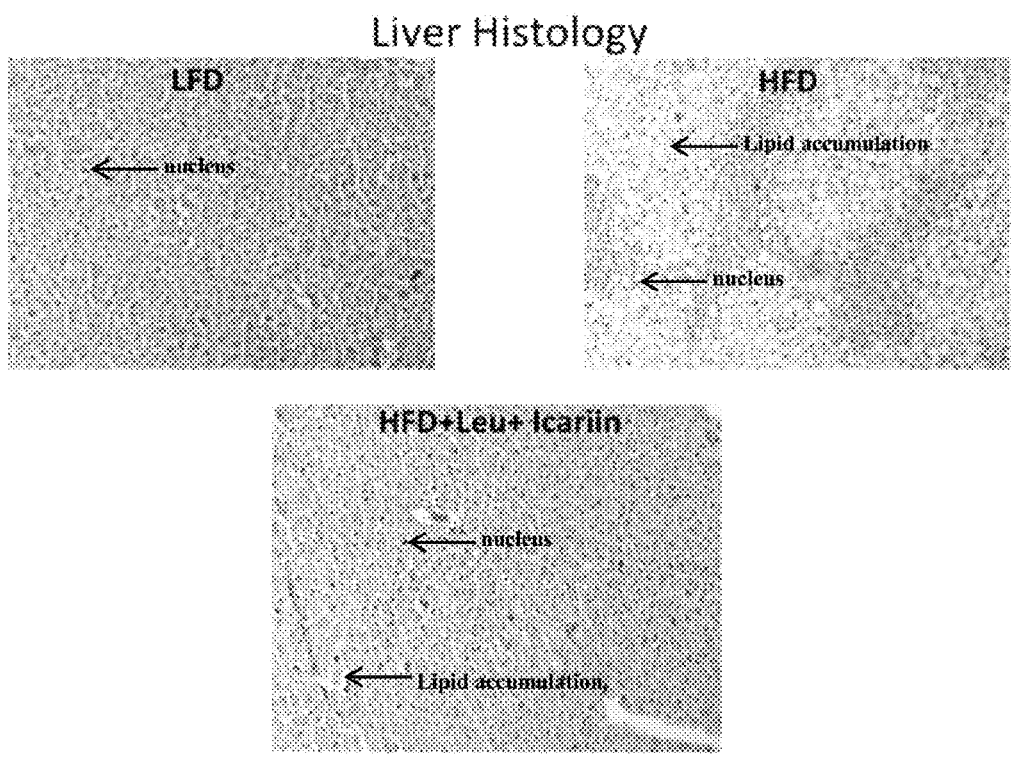
FIG. 14 depicts effects of administration of low dose leucine and icariin on hepatic lipid accumulation following a chronic high fat diet.

Histological analysis reveals that control animals fed with low fat diet (LFD) have normal cellular structure and no detectable lipid accumulation. By contrast, animals fed with high fat diet (HFD) induced significant hepatic steatosis, as shown by the appearance of lipid vesicles and lipid accumulation in liver cells (FIG. 14). Combining subtherapeutic dosages of leucine with icariin appeared to reverse hepatic steatosis (FIG. 14). The liver cells show comparable cellular structure with liver cells in the LFD panel.

Figure 15:
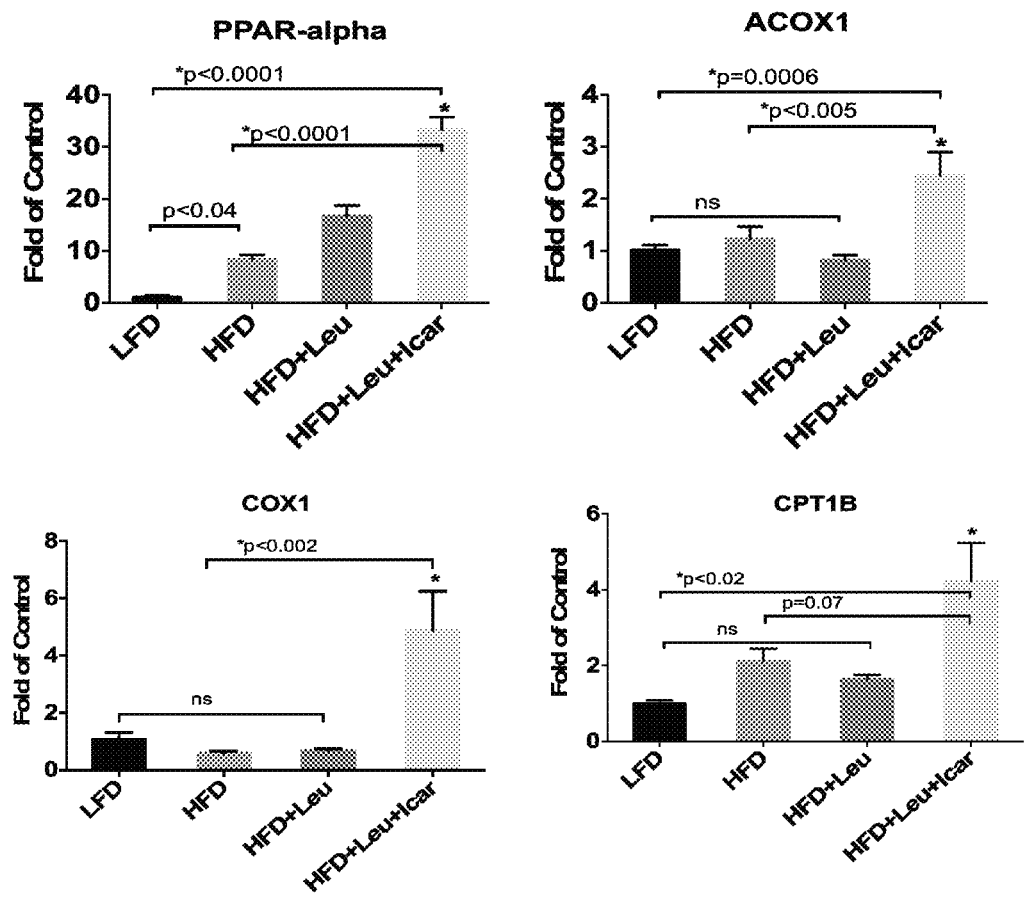
FIG. 15 depicts effects of administration of low dose leucine and icariin on hepatic expression of fatty acid oxidation genes.

Combining subtherapeutic dosages of leucine with icariin resulted in marked stimulation of liver fatty acid oxidation gene expression (FIG. 15).

Figure 16:
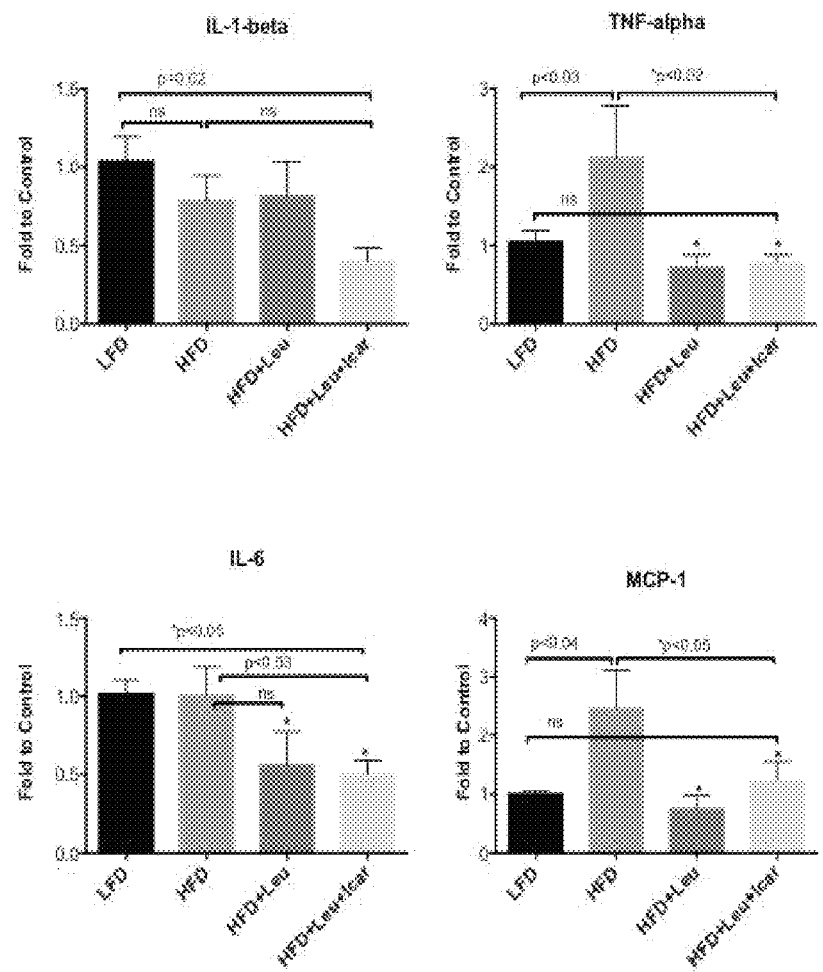
FIG. 16 depicts effects of administration of low dose leucine and icariin on hepatic expression of inflammatory genes.
Figure 17:
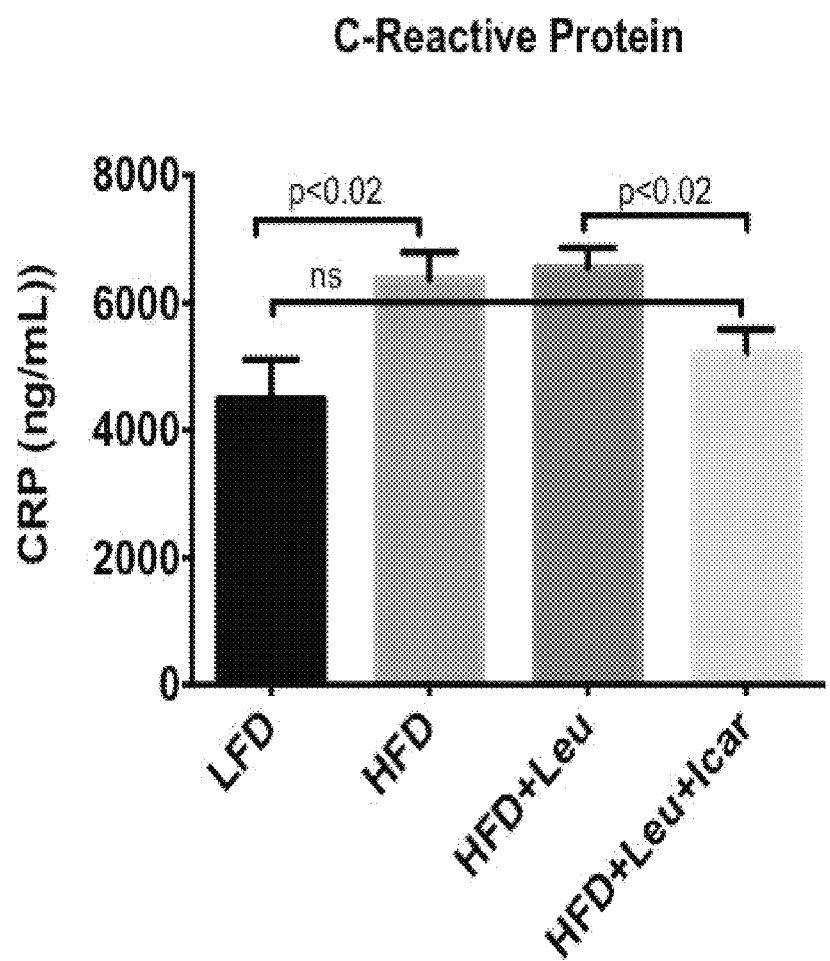
FIG. 17 depicts effects of administration of low dose leucine and icariin circulating levels of C-reactive protein.

Likewise, combining subtherapeutic dosages of leucine with icariin resulted in marked suppression of hepatic inflammatory genes interleukin (IL)-6, IL-1β, tumor necrosis factor (TNF)-α and monocyte chemotactic protein (MCP)-1 (FIG. 16). Moreover, using circulating C-reactive protein (CRP) as an integrated marker of hepatic inflammatory stress, the leucine-PDE5 inhibitor combination reversed the HFD-induced elevation of CRP, while leucine alone exerted no independent effect (FIG. 17).

Example 6: Prophylactic Effect of Various Combinations of Leucine, Metformin, and Resveratrol on Hepatic Steatosis In this study, the prophylactic effects of metformin alone, and various combinations of metformin, leucine, and resveratrol on liver mass and hepatic steatosis are assessed. C57Bl/6 mice are assigned to the following experimental groups as depicted in Table 25:

TABLE 25

Example 6 experimental groups
Treatment Group

Low fat diet (LFD) alone
High fat diet (HFD) alone
HFD + therapeutic metformin alone (1.5 g metformin/kg diet; calculated human equivalent dose, 1,500 mg/day)
HFD + Leucine (24 g/kg diet; calculated human equivalent dose, exclusive of diet, 2-3 g/day) + metformin (0.15-0.50 g/kg diet metformin; calculated human equivalent dose, 125-500 mg/day of metformin)
HFD + Leucine (as above) + metformin (as above) + resveratrol (12.5 mg/kg diet)

Drug treatments and high fat diet feeding (as described in Example 1) are initiated on the same day and are carried out for six weeks. The effects of the treatments and diet on liver mass and hepatic lipid accumulation are assessed as described in the preceding examples. High fat diet alone results in increased liver mass and hepatic lipid accumulation. Administration of therapeutic dosages of metformin alone, concurrent with high fat feeding, attenuates the HFD-induced increase in liver mass and hepatic lipid accumulation. Co-administration of leucine and sub-therapeutic doses of metformin, with or without resveratrol prevents the HFD-induced increase in liver mass and hepatic lipid accumulation.

Example 7: Prophylactic Effect of Various Combinations of HMB, Metformin, and Resveratrol on Hepatic Steatosis In this study, the prophylactic effects of metformin alone, and various combinations of metformin, HMB, and resveratrol on liver mass and hepatic steatosis are assessed. C57Bl/6 mice are assigned to the following experimental groups as depicted in Table 26:

TABLE 26

| Example 7 experimental groups Treatment Group |
| --- |
| Low fat diet (LFD) alone |
| High fat diet (HFD) alone |
| HFD + therapeutic metformin alone (1.5 g metformin/kg diet; calculated human equivalent dose, 1,500 mg/day) |
| HFD + HMB (CaHMB, 2 g/kg diet; calculated human equivalent dose, ~500 mg/day)) + metformin (0.15-0.50 g/kg diet metformin; calculated human equivalent dose, 125-500 mg/day of metformin) |
| HFD + HMB (as above) + metformin (as above) + resveratrol (12.5 mg/kg diet) |

Drug treatments and high fat diet feeding (as described in Example 1) are initiated on the same day and are carried out for six weeks. The effects of the treatments and diet on liver mass and hepatic lipid accumulation are assessed as described in the preceding examples. High fat diet alone results in increased liver mass and hepatic lipid accumulation. Administration of therapeutic dosages of metformin alone, concurrent with high fat feeding, attenuates the HFD-induced increase in liver mass and hepatic lipid accumulation. Co-administration of HMB and sub-therapeutic doses of metformin, with or without resveratrol, prevents the HFD-induced increase in liver mass and hepatic lipid accumulation.

Example 8: Prophylactic Effect of Various Combinations of Leucine and a PDE5-Specific Inhibitor on Hepatic Steatosis In this study, the prophylactic effects of sub-therapeutic leucine alone, and co-administration of leucine and the PDE5-specific inhibitor icariin on liver mass and hepatic steatosis are assessed. C57Bl/6 mice are assigned to the following experimental groups as depicted in Table 27:

TABLE 27

| Example 8 experimental groups Treatment Group |
| --- |
| Low fat diet (LFD) alone |
| High fat diet (HFD) alone |
| HFD + sub-therapeutic leucine alone (24 g/kg diet; |

TABLE 27-continued

| Example 8 experimental groups Treatment Group |
| --- |
| calculated human equivalent dose, exclusive of diet, 2-3 g/day) |
| HFD + leucine (as above) + icariin (25 mg/kg diet; calculated human equivalent dose, 25 mg/day of icariin) |

Drug treatments and high fat diet feeding (as described in Example 1) are initiated on the same day and are carried out for six weeks. The effects of the treatments and diet on liver mass and hepatic lipid accumulation are assessed as described in the preceding examples. High fat diet alone results in increased liver mass and hepatic lipid accumulation. Administration of therapeutic dosages of sub-therapeutic leucine alone has no significant effect on HFD-induced increase in liver mass and hepatic lipid accumulation. Co-administration of leucine and sub-therapeutic doses of icariin prevents the HFD-induced increase in liver mass and hepatic lipid accumulation.

Example 9: Interactive Effects of Leucine, Metformin and Sildenafil in Hepatocytes In this study, the in vitro effects of sub-therapeutic doses of leucine (0.5 mM), metformin, and PDE5 inhibition with sildenafil (0.1-10 nM) on hepatocyte sirtuin signaling, fat oxidation and triglyceride content were evaluated in HepG2 cells.

Although leucine-metformin and leucine-sildenafil stimulated Sirt1 and AMPK activation, the three-way combination stimulated both Sirt1 and AMPK to a significantly greater degree than either of the two way combinations (leucine-metformin, leucine-sildenafil).

Figure 18:
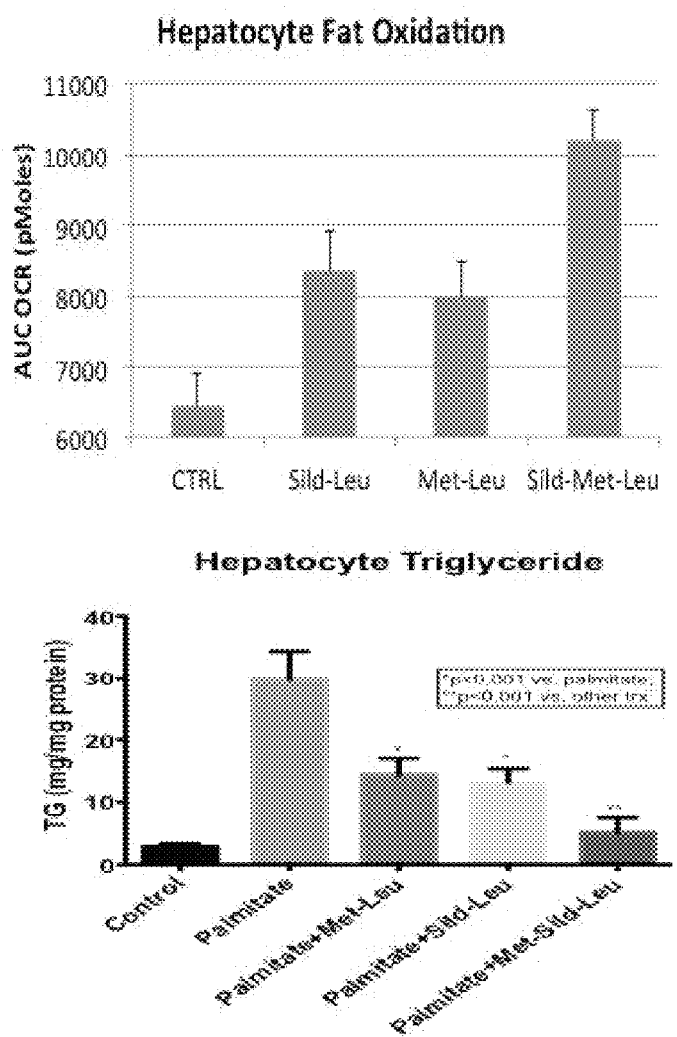
FIG. 18 depicts effects of subtherapeutic amounts of leucine, metformin and sildenafil on fat oxidation (upper panel) and palmitate-induced triglyceride accumulation (lower panel) in HepG2 hepatocytes.

Moreover, although both leucine-metformin and leucine sildenafil stimulated hepatocyte fat oxidation and inhibited palmitate-induced hepatocyte triglyceride accumulation, the three-way combination of leucine, metformin and sildenafil was twice as effective as either of the two-way combinations (FIG. 18).

Example 10: Interactive Effects of Leucine-Metformin-Sildenafil Versus Leucine-Metformin and Leucine-Sildenafil in a Mouse Model of Non-Alcoholic Steatohepatitis (NASH)

In this study, the effects of subtherapeutic doses of leucine, metformin and sildenafil were compared as two-way and three-way combinations.

C57Bl/6 mice were assigned to the following experimental groups, as depicted in table 28. Briefly, C57Bl/6 mice were fed a high-fat atherogenic diet (HF/ATH), similar to the HFD used in examples 1-9, with the addition of cholesterol (1.25%) and cholate (0.5%) to induce NASH. Following induction of NASH, animals were then randomized for six weeks (n=10/group), as follows:

TABLE 28

| Example 10 experimental groups Treatment Group |
| --- |
| Low fat diet (LFD) alone |
| High fat-atherogenic diet (HF/ATH) alone |
| HF/ATH + Leucine (24 g/kg diet; calculated human equivalent dose, exclusive of diet, 2-3 g/day) + metformin (0.25 g/kg |

TABLE 28-continued

Example 10 experimental groups
Treatment Group diet metformin; calculated human equivalent dose, 250 mg/day of metformin)
HF/ATH + sildenafil (25 mg/kg diet; calculated human equivalent dose, 1 mg/day)
HF/ATH + Leucine (24 g/kg diet; calculated human equivalent dose, exclusive of diet, 2-3 g/day) + sildenafil (25 mg/kg diet; calculated human equivalent dose, 1 mg/day)
HFD + sildenafil (25 mg/kg diet; calculated human equivalent dose, 1 mg/day) + metformin (0.25 g/kg diet metformin; calculated human equivalent dose, 250 mg/day of metformin)
HFD + leucine (24 g/kg diet; calculated human equivalent dose, exclusive of diet, 2-3 g/day) + sildenafil (25 mg/kg diet; calculated human equivalent dose, 1 mg/day) + metformin (0.25 g/kg diet metformin; calculated human equivalent dose, 250 mg/day of metformin)

Drug treatments and high fat diet feeding (as described in Example 1) are initiated on the same day and are carried out for six weeks. The effects of the treatments and diet on liver mass and hepatic lipid accumulation are assessed as described in the preceding examples.

Figure 19:
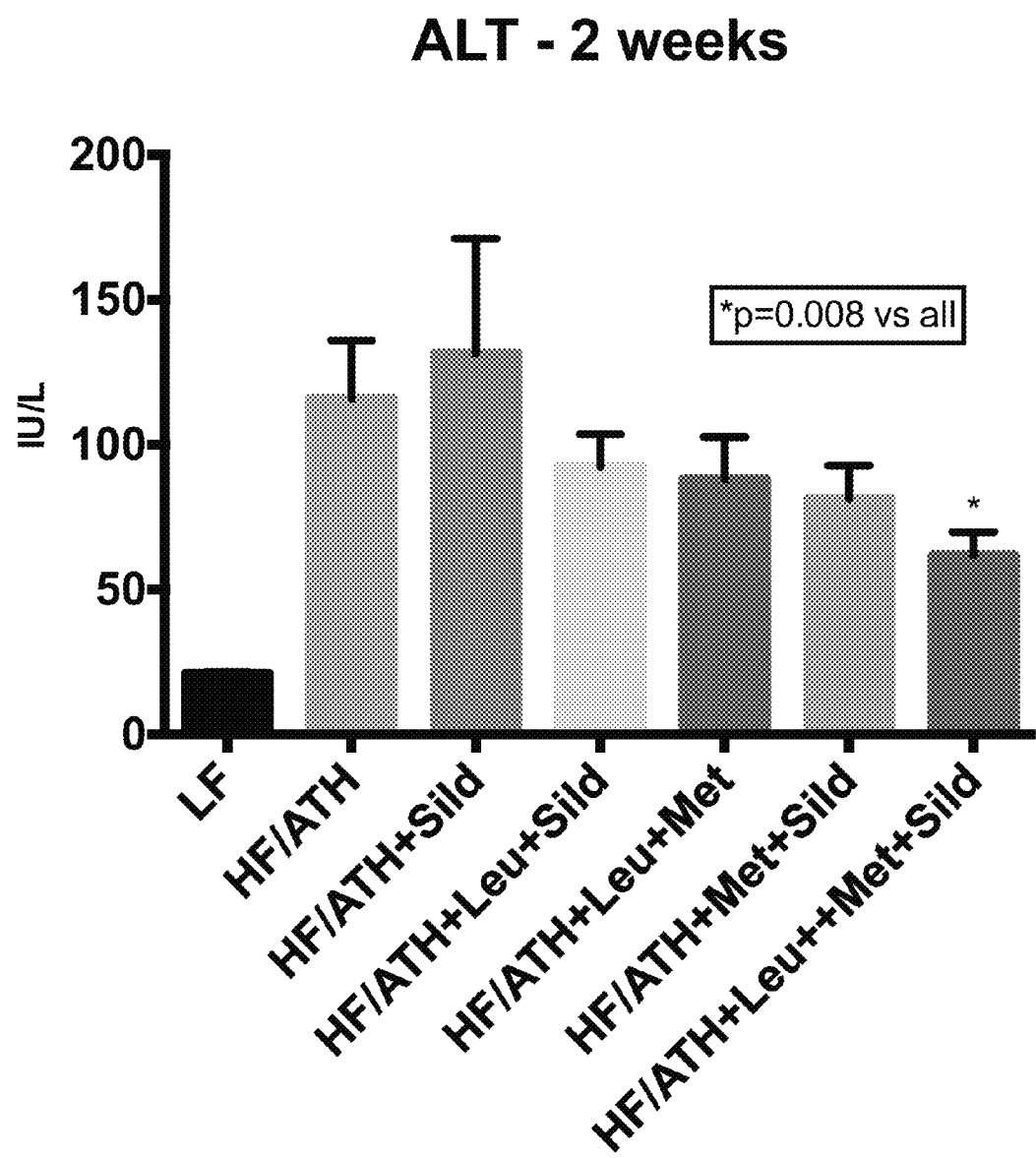
FIG. 19 depicts effects of two-weeks administration of low dose leucine, metformin and sildenafil on circulating levels of alanine amino transferase (ALT) following a chronic atherogenic diet.
Figure 20:
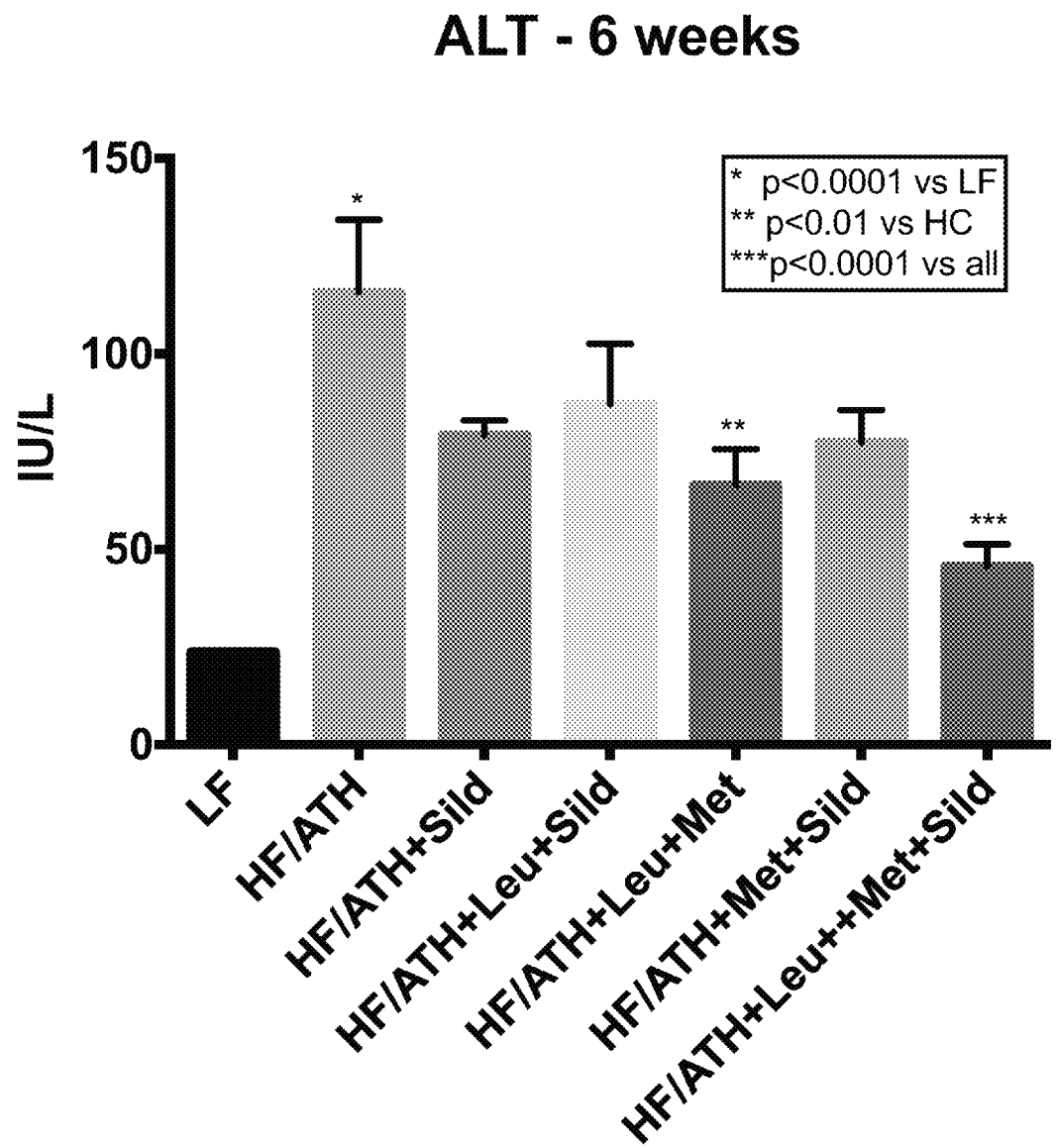
FIG. 20 depicts effects of six-weeks administration of low dose leucine, metformin and sildenafil on circulating levels of alanine amino transferase (ALT) following a chronic atherogenic diet.
Figure 21:
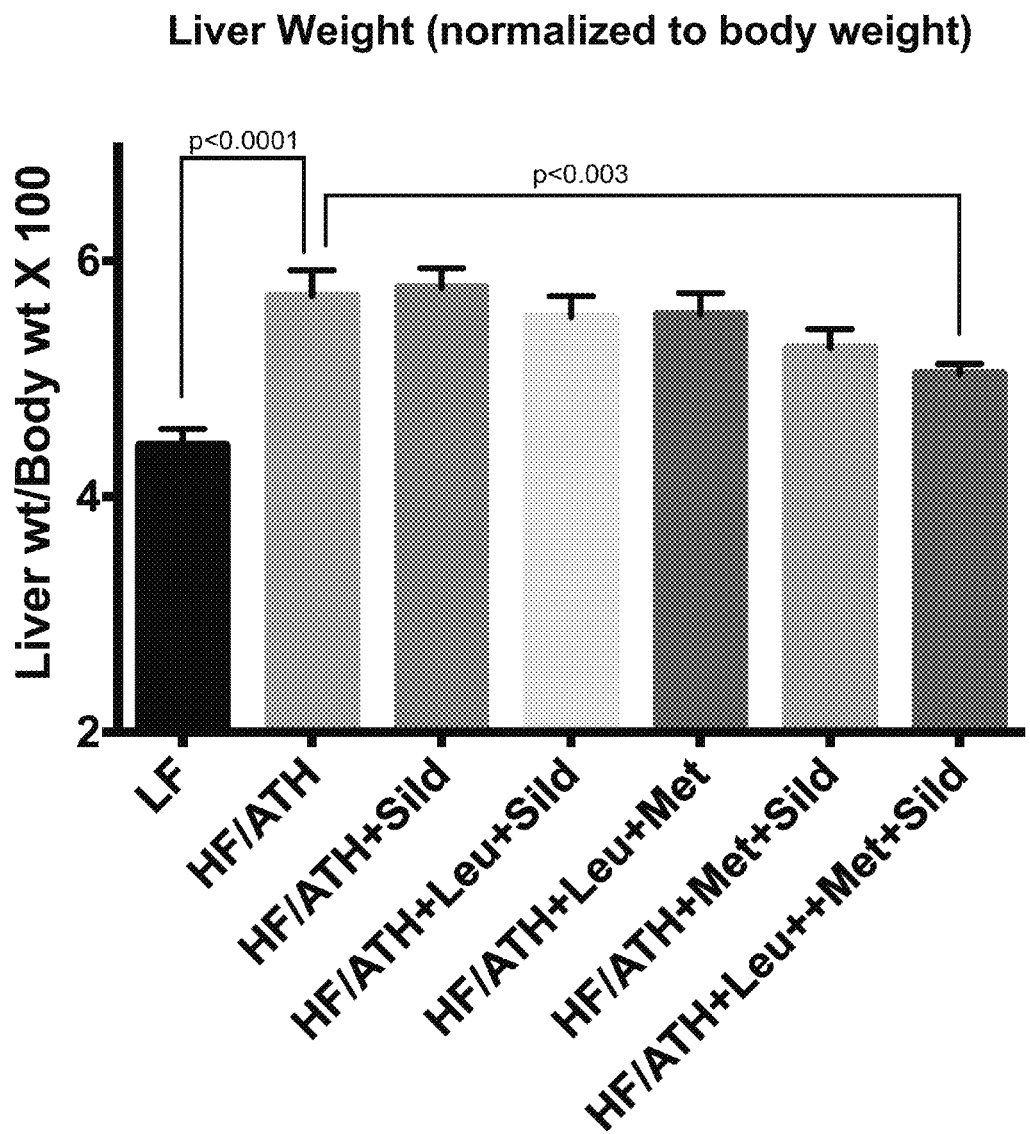
FIG. 21 depicts effects of six-weeks administration of low dose leucine, metformin and sildenafil on liver mass, normalized to body weight.
Figure 22:
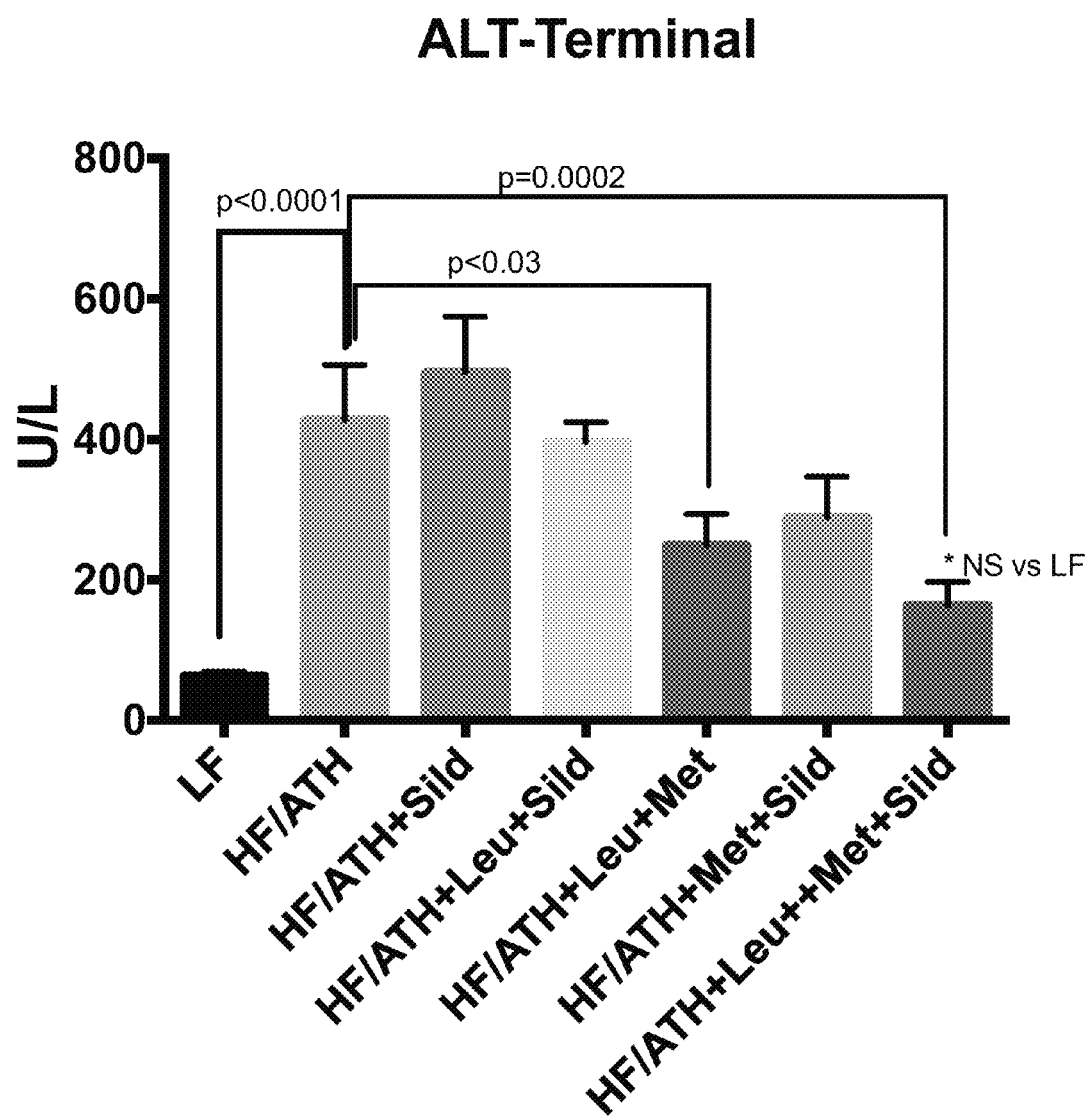
FIG. 22 depicts interactive effects of eight-weeks administration of leucine, metformin and sildenafil on plasma alanine aminotransferase (ALT) levels.

The HF/ATH diet resulted in significant hepatocellular injury, as evidenced by a ~six-fold increase in alanine aminotransferase (ALT; FIG. 19). By contrast, prolonged treatment of sildenafil with leucine and metformin enhances the therapeutic efficacy of leucine and metformin in reducing liver fibrosis in mouse. Treatment efficacy of the leucine-metformin-sildenafil combination was evident within two weeks of treatment; although both leucine-metformin and leucine-sildenafil reduced ALT levels, the triple combination exerted a significantly greater effect, resulting in a ~50% decrease in ALT at two weeks (FIG. 19), and a decrease of >60% at 6 weeks (FIG. 20), and at the 8 week termination of the study (FIG. 22). The HF/ATH diet also resulted in a significant 29% increase in body weight-normalized liver mass (p<0.0001; FIG. 21). Both leucine-metformin and leucine-sildenafil combinations resulted in non-significant reductions in liver mass. However, the triple combination of leucine, metformin and sildenafil resulted in a 12% decrease in liver mass (p<0.003), reflecting a reduction in hepatic lipid accumulation.

Figure 23:
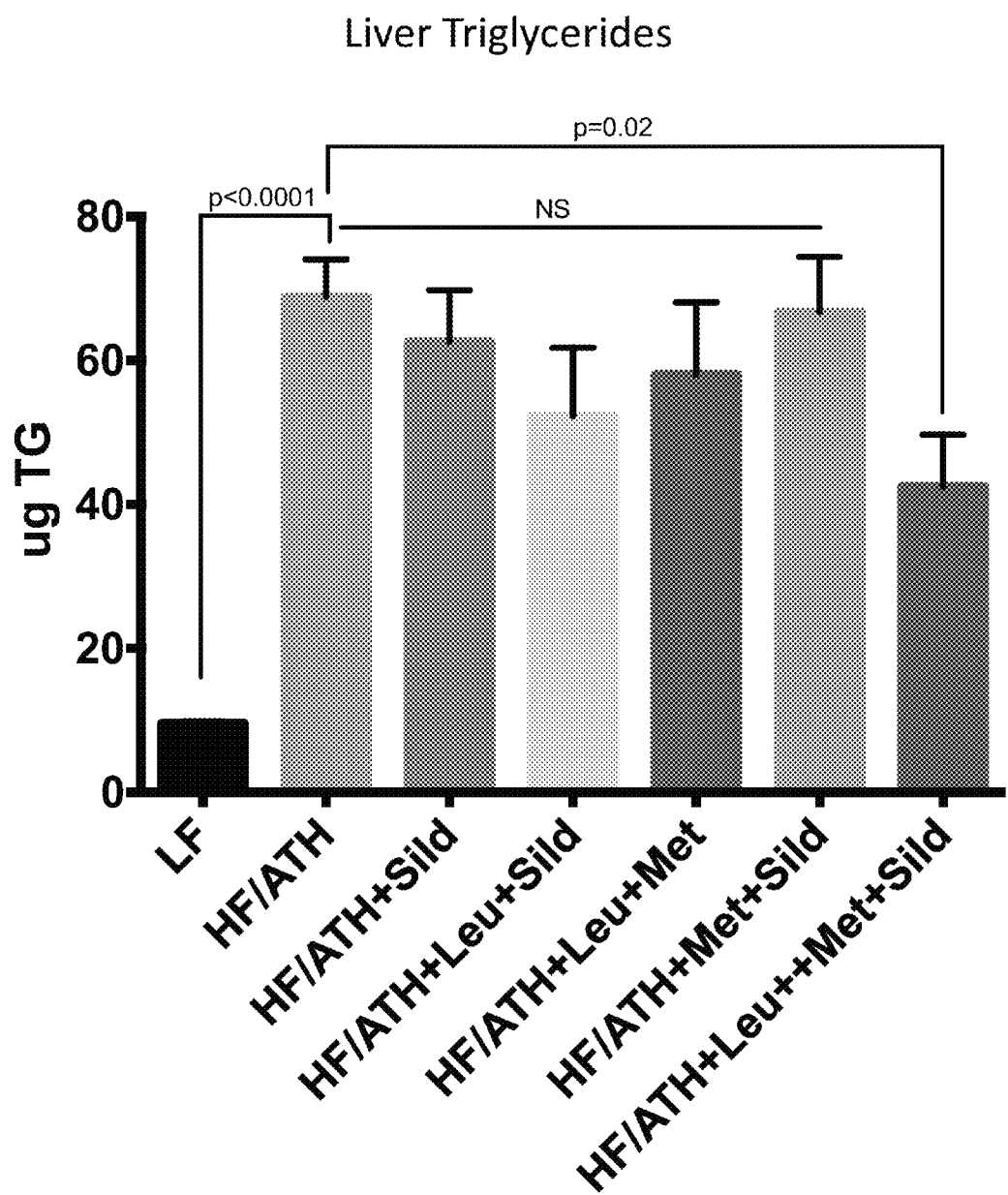
FIG. 23 depicts interactive effects of leucine, metformin and sildenafil on liver triglycerides.
Figure 24:
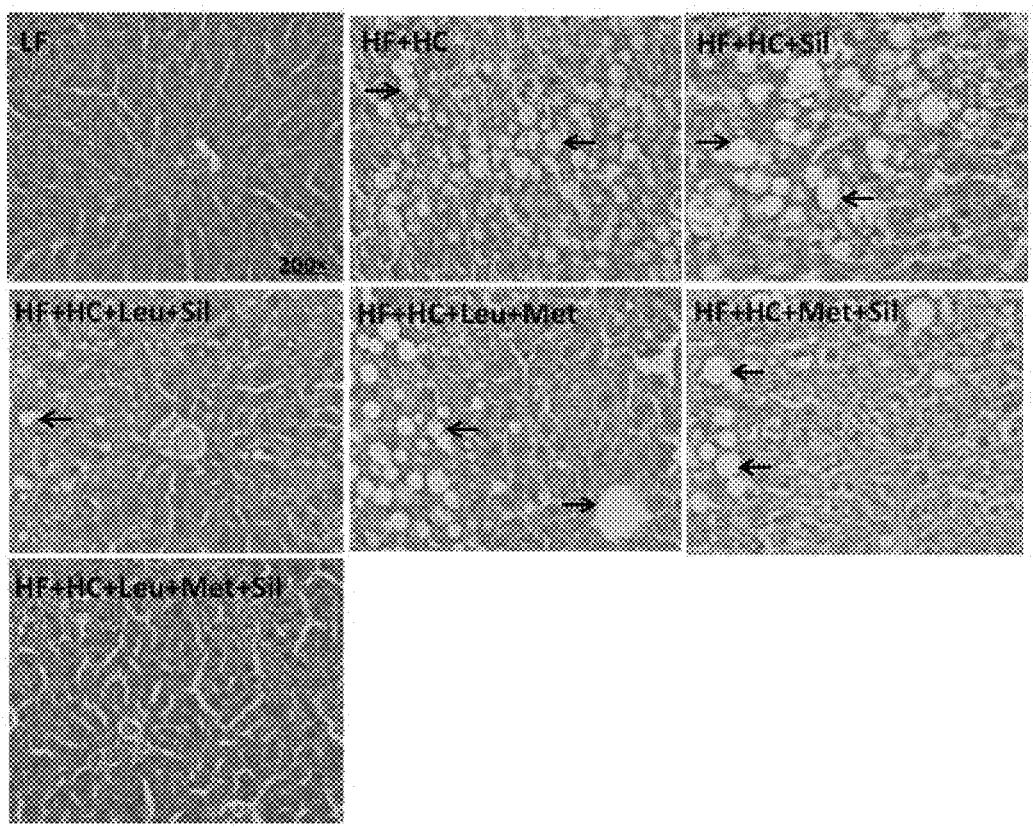
FIG. 24 illustrates interactive effects of leucine, metformin and sildenafil on liver histology.

Liver triglycerides exhibited a similar trend. The HF/ATH diet resulted in a 7-fold increase in liver triglycerides (p<0.0001). Both leucine-metformin and leucine-sildenafil combinations resulted in non-significant reductions, while the triple combination of leucine, metformin and sildenafil resulted in a 38% decrease in liver triglycerides (p=0.02; FIG. 23). Histological data support these observations. The HF/ATH diet resulted in a pronounced increase in intracellular lipid droplets and ballooned hepatocytes (arrows) compared with the LF control (FIG. 24). Both leucine-metformin and leucine-sildenafil combinations attenuated, but did not reverse, these effects. In contrast, the triple combination of leucine, metformin and sildenafil resulted in a substantial reversal of this steatohepatitis (FIG. 24).

Figure 25:
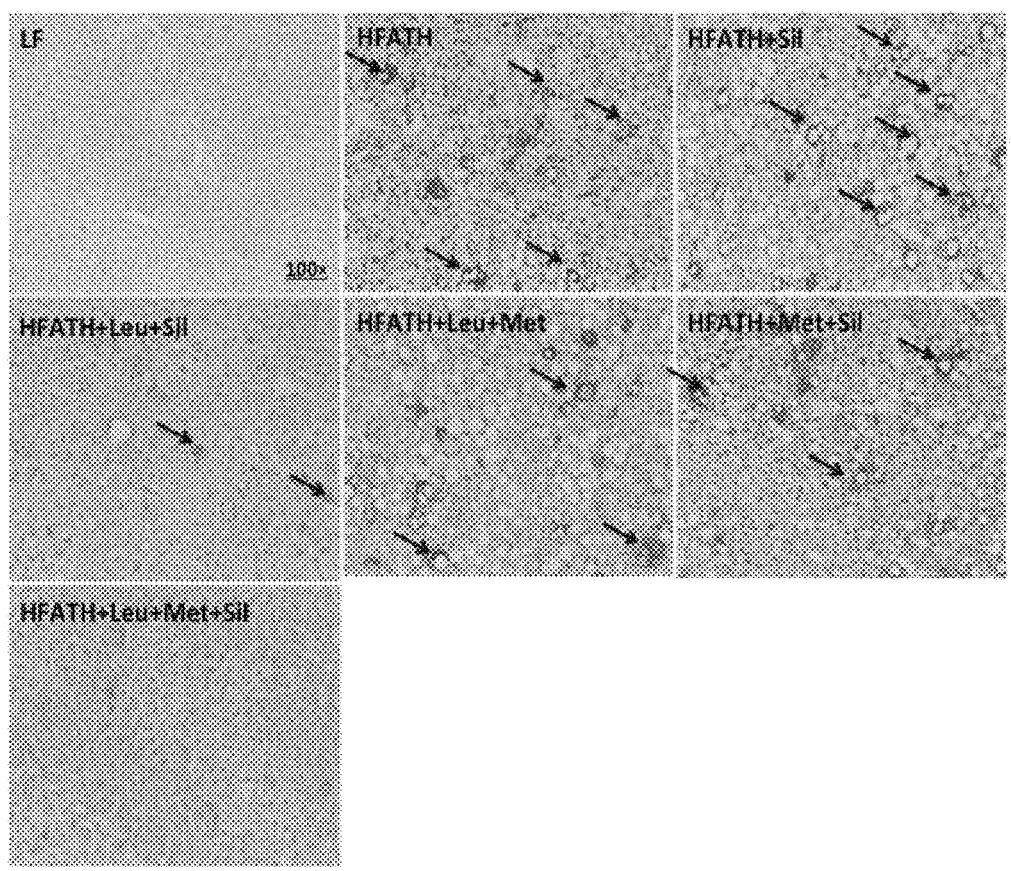
FIG. 25 illustrates effects of leucine, metformin and sildenafil on liver CD68 immunohistochemistry; arrows illustrate areas of CD68 staining.
Figure 26:
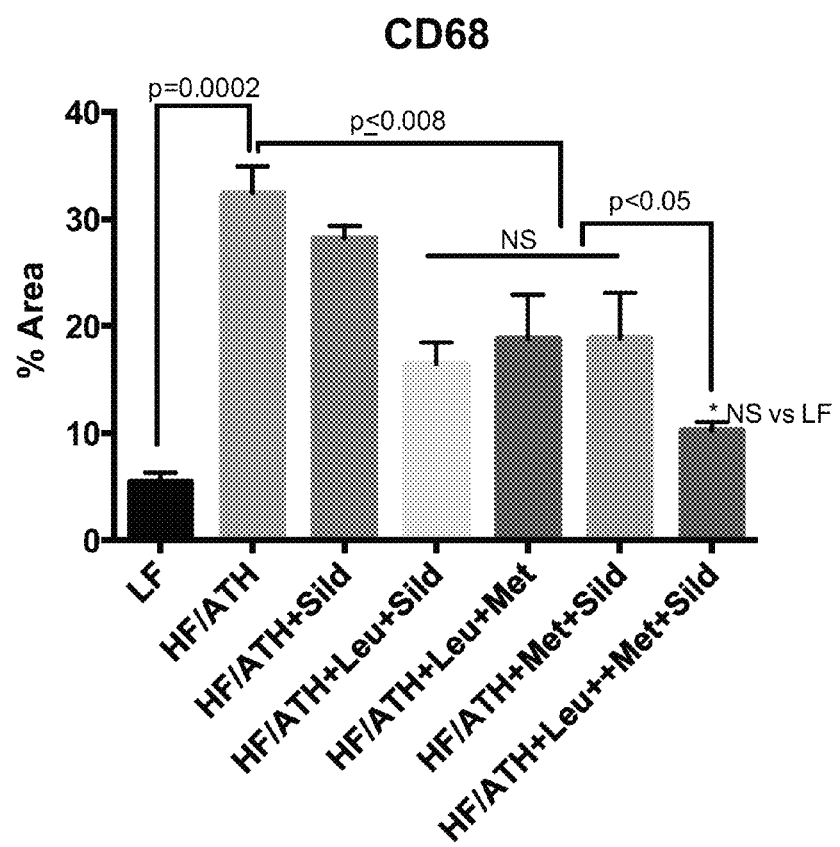
FIG. 26 depicts quantitation of interactive effects of leucine, metformin and sildenafil on liver CD68 immunohistochemistry.

Further, immunohistochemistry (IHC) using CD68 staining shows a marked increase in macrophage infiltration (arrows) on the HF/ATH vs. LF diet (FIGS. 25 and 26). This was attenuated, but not reversed, by the leucine-metformin and leucine-sildenafil combinations, while the triple combination of leucine, metformin and sildenafil resulted in a substantial reversal of this effect. FIG. 25 shows representative liver CD68 staining, and FIG. 26 shows quantitation of these data.

Figure 27A:
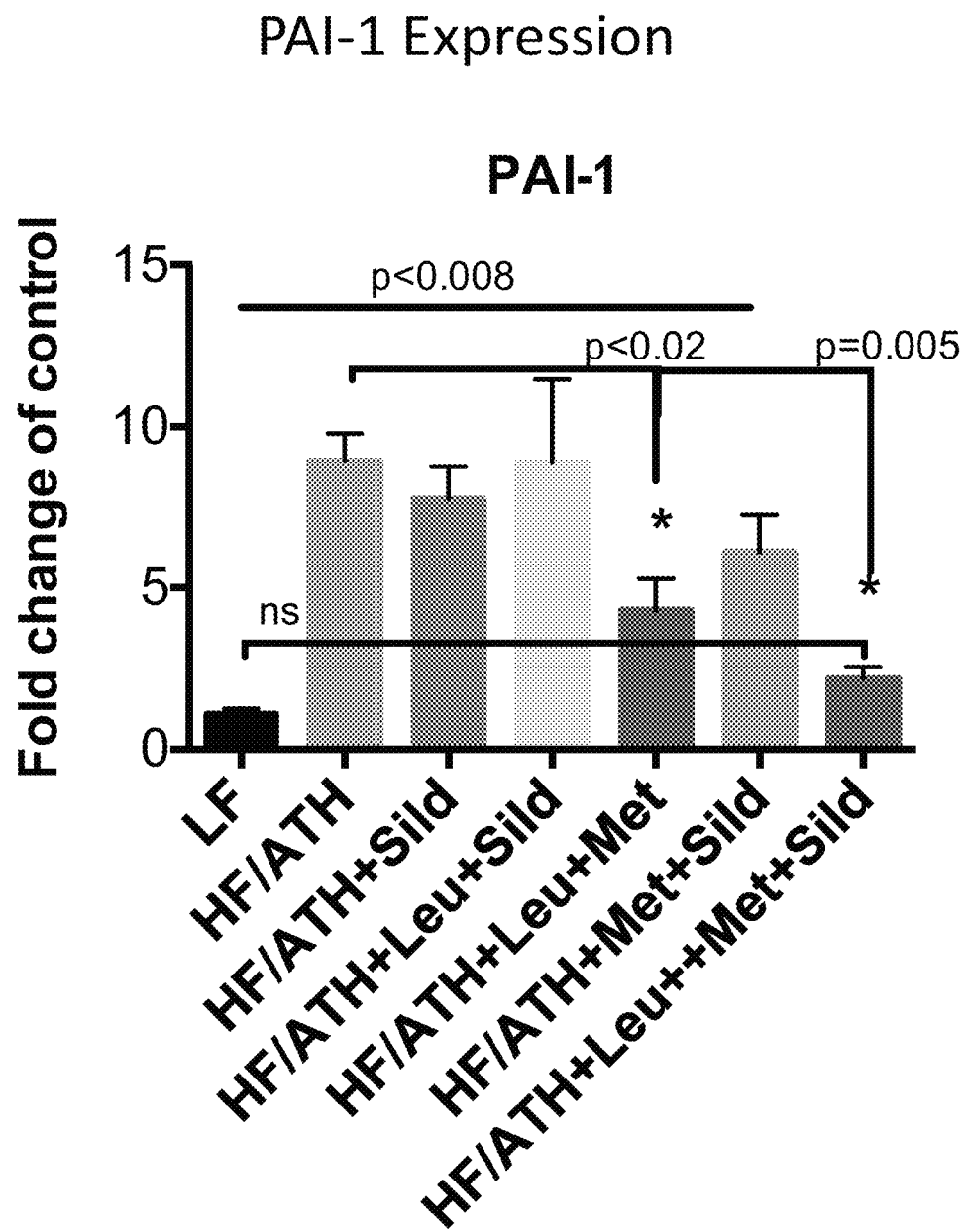
FIG. 27a depicts interactive effects of leucine, metformin and sildenafil on hepatic expression of PAI-1, TGFβ, and TNFα.
Figure 27B:
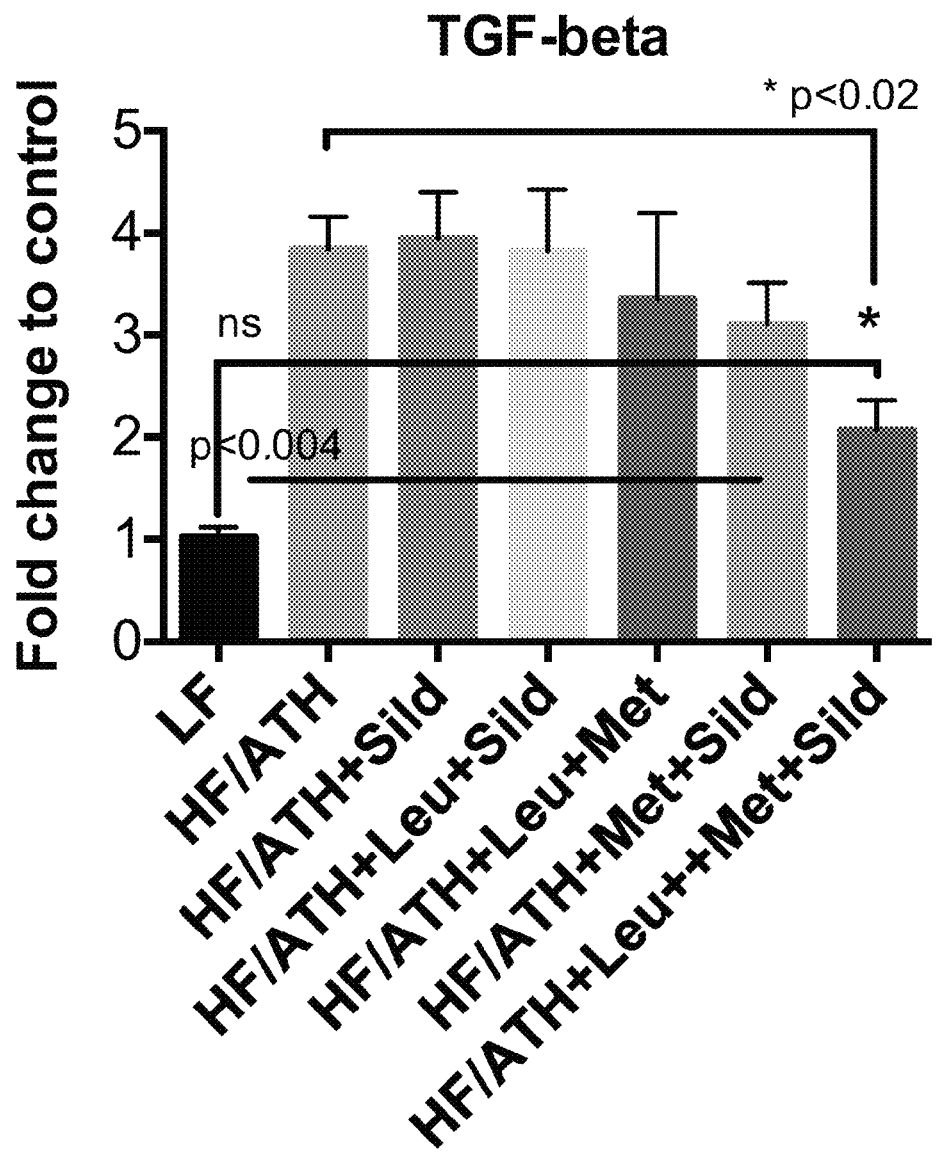
FIG. 27b depicts interactive effects of leucine, metformin and sildenafil on hepatic expression of PAI-1, TGFβ, and TNFα.
Figure 27C:
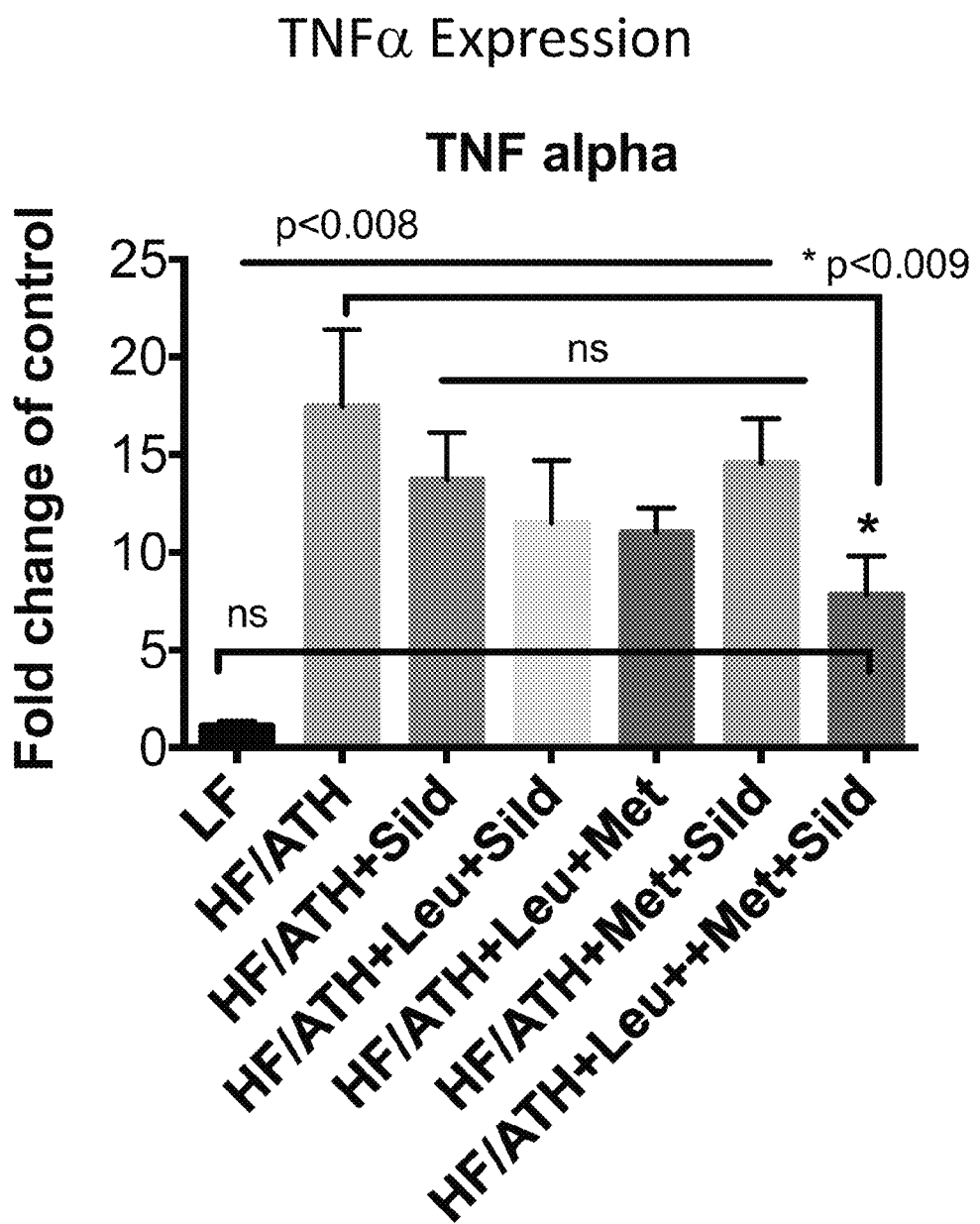
FIG. 27c depicts interactive effects of leucine, metformin and sildenafil on hepatic expression of PAI-1, TGFβ, and TNFα.

Consistent with this, hepatic expression of inflammatory genes was markedly elevated by the HF/ATH diet, and returned to levels not significantly different from the LF controls by the triple combination of leucine, metformin and sildenafil (FIG. 27).

Figure 28A:
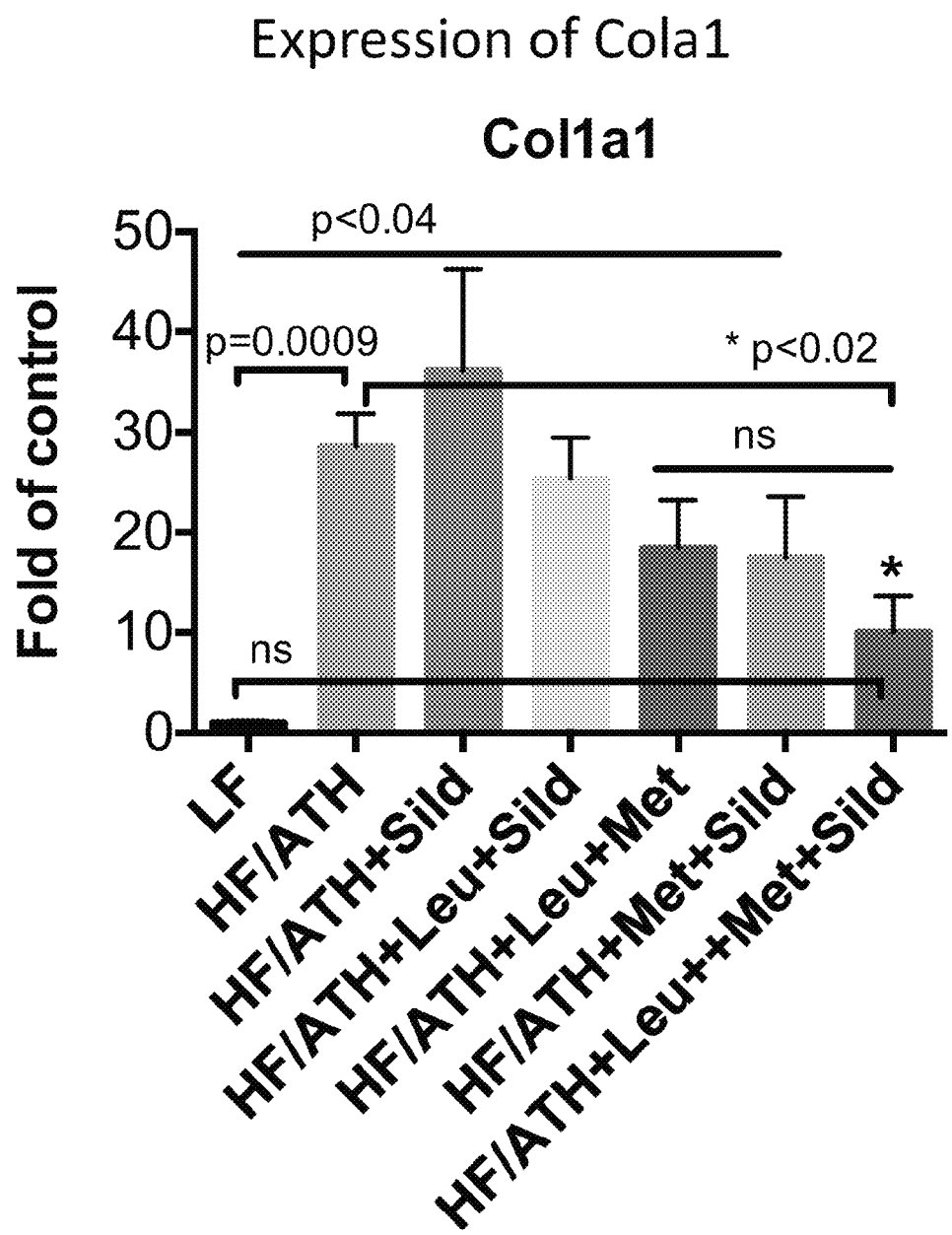
FIG. 28a depicts interactive effects of leucine, metformin and sildenafil on hepatic expression of collagen genes.
Figure 28B:
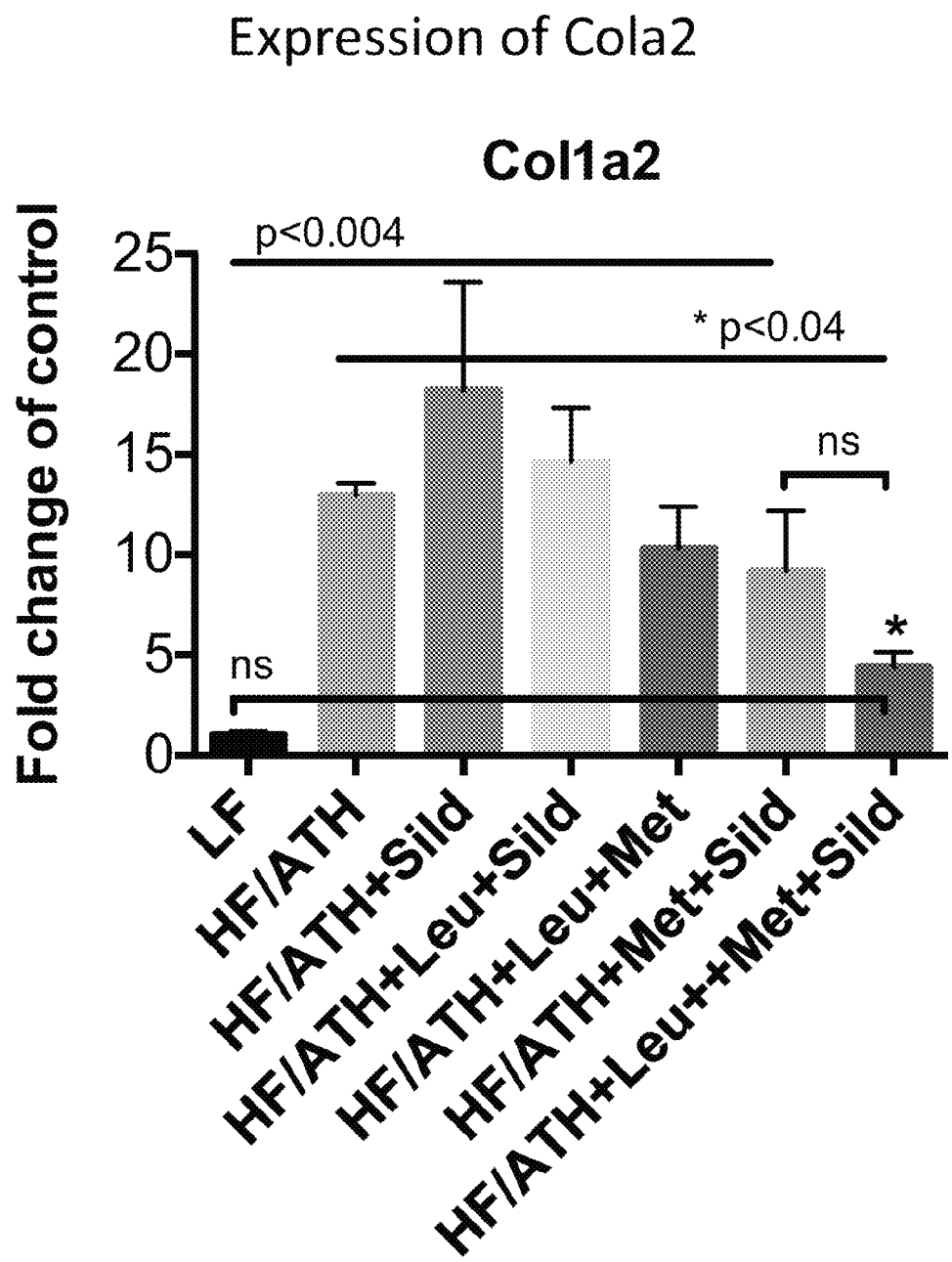
FIG. 28b depicts interactive effects of leucine, metformin and sildenafil on hepatic expression of collagen genes.
Figure 28C:
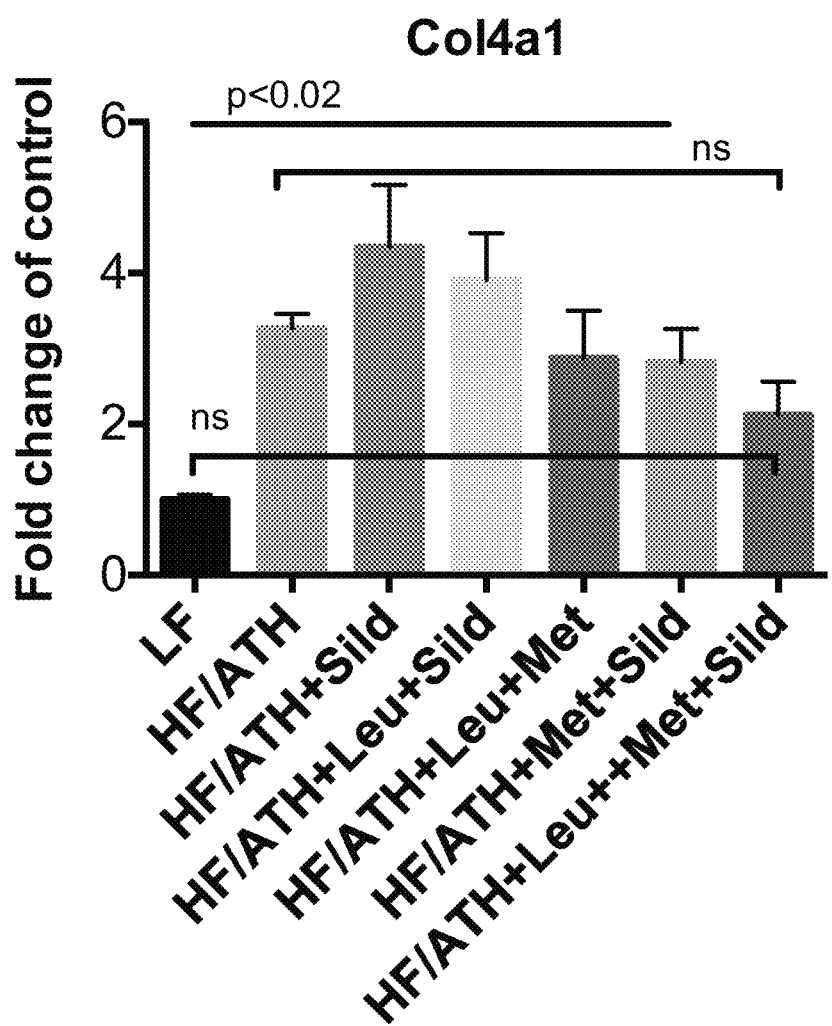
FIG. 28c depicts interactive effects of leucine, metformin and sildenafil on hepatic expression of collagen genes.

Further, expression of collagen isoforms was markedly elevated by HF/ATH diet, and returned to levels not significantly different from the LF controls by the triple combination of leucine, metformin and sildenafil (FIG. 28).

Figure 29:
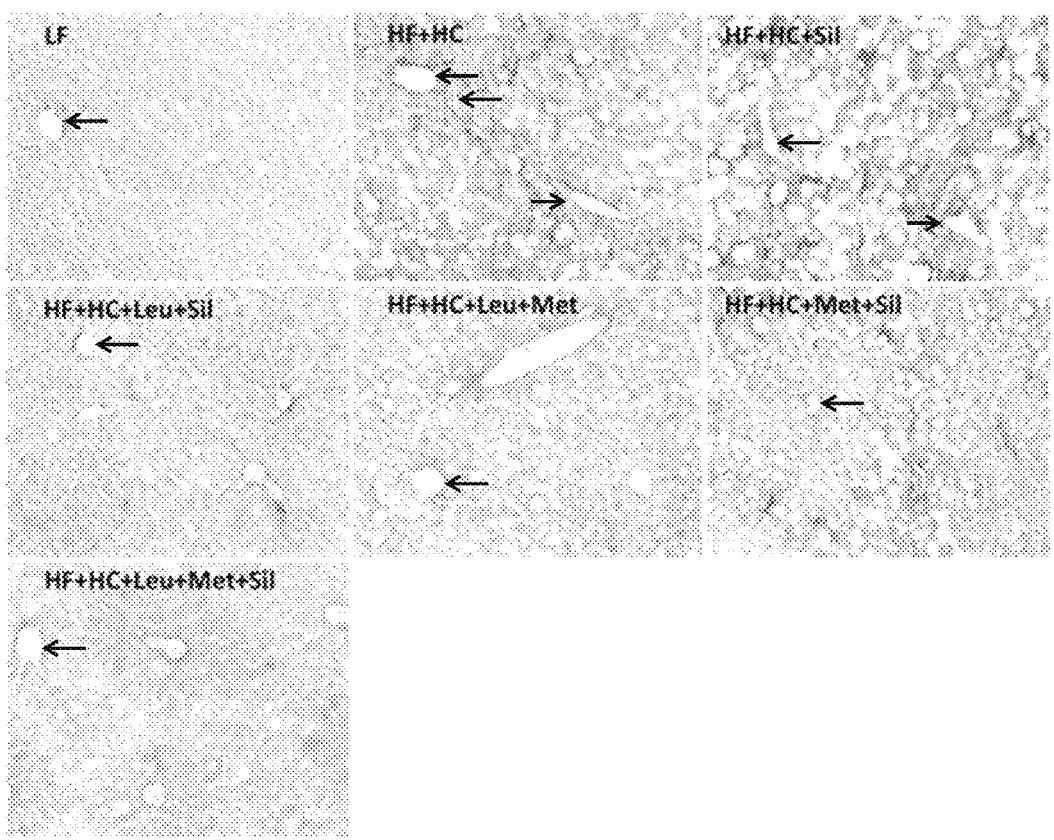
FIG. 29 illustrates interactive effects of leucine, metformin and sildenafil on liver fibrosis via picrosirius red staining.
Figure 30:
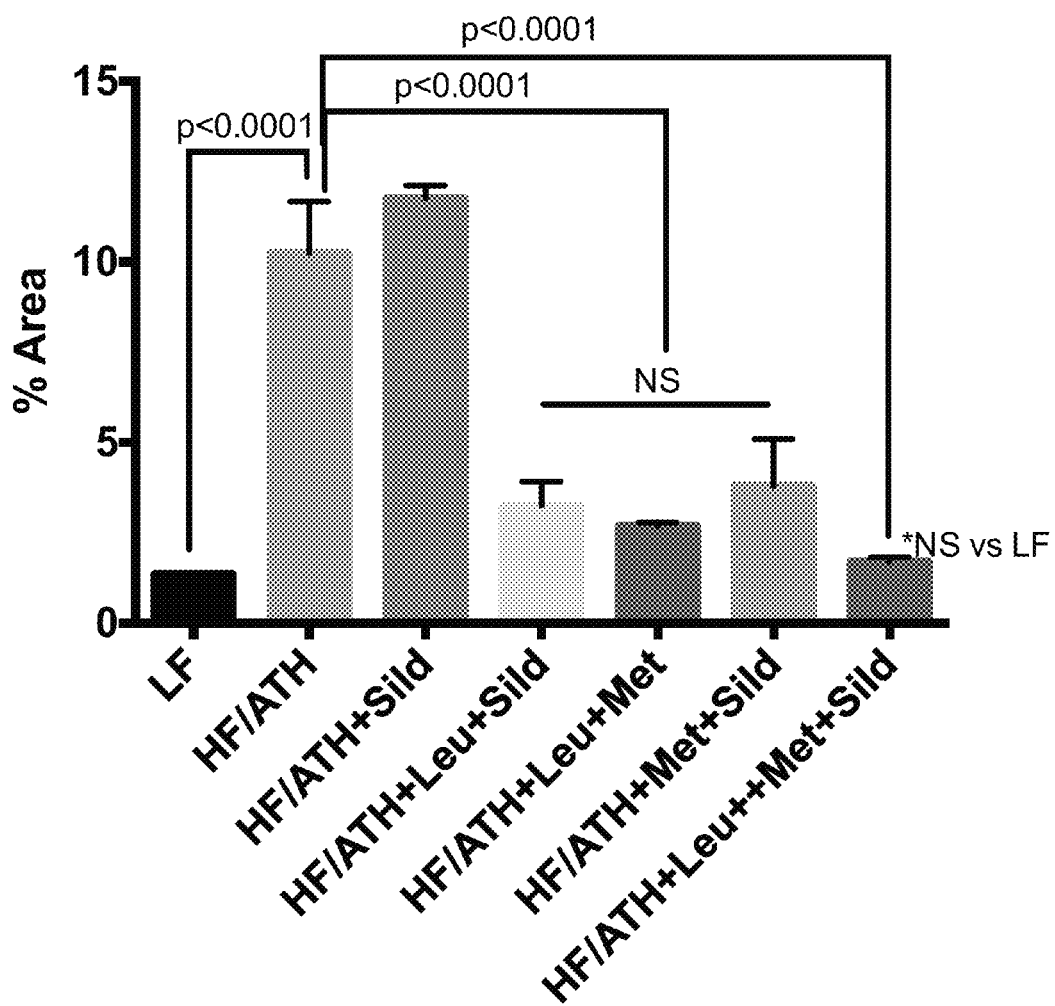
FIG. 30 depicts quantitation of interactive effects of leucine, metformin and sildenafil on liver fibrosis.

Consistent with this, picrosirius red staining showed a marked increase in fibrosis (arrows) on the HF/ATH vs. LF diet (FIGS. 29 and 30). This was attenuated, but not reversed, by the leucine-metformin and leucine-sildenafil combinations, while the triple combination of leucine, metformin and sildenafil resulted in a substantial reversal of this effect. FIG. 29 below shows representative liver picrosirius red staining, and FIG. 30 shows quantitation of these data.

Example 11: Interactive Effects of Leucine-Metformin-Sildenafil Versus Leucine-Metformin and Leucine-Sildenafil in Human of Non-Alcoholic Steatohepatitis (NASH)

In this study, the effects of subtherapeutic doses of leucine, metformin and sildenafil are compared as two-way and three-way combinations.

Human with non-alcoholic steatohepatitis is assigned to the following experimental groups, as depicted in Table 29. The duration of such trial includes about 12 months.

TABLE 29

Example 11 experimental groups
Treatment Group

Placebo
Metformin (250 mg, administered twice a day)
Leucine (1.1 g, administered twice a day) + metformin (250 mg, administered twice a day)
Sildenafil (1 mg, administered twice a day)
Leucine (1.1 g, administered twice a day) + sildenafil (1 mg, administered twice a day)
Sildenafil (1 mg, administered twice a day) + metformin (250 mg administered twice a day)
Leucine (1.1 g, administered twice a day) + sildenafil (1 mg, administered twice a day) + metformin (250 mg, administered twice a day)

The effects of the treatments and diet on hepatic lipid accumulation are assessed using a liver biopsy, a blood test, a FibroTest, a SteatoTest, a gene expression profiling of the genes provided in Example 3 and Example 4, or combinations thereof. A liver biopsy is performed and improvement in NAFLD Activity Score (NAS) is evaluated. An improvement of resolution of NASH is also evaluated.

The placebo group is expected to maintain significant hepatocellular injury. In response to the treatments, it is expected to improve NAFLD Activity Score by at least two points and to improve resolution of NASH in fibrosis in both leucine and metformin double combination, with significant further improvement resulting from the leucine, metformin and sildenafil triple combination.

Example 12: Interactive Effects of Leucine, Metformin and Sildenafil Combination Treatment on Non-Alcoholic Fatty Liver Disease (NAFLD)

This is a 12-month randomized, double-blind, placebo-controlled trial for treatment of a leucine, metformin and sildenafil combination treatment on non-alcoholic fatty liver disease (NAFLD). A total of 425 patients are to be randomized with a goal of 375 patients to complete all assessments over 12 months. Patients with histologically confirmed NASH will be randomized to five arms (n=75 completers/arm) are as shown in Table 30. Patients are administered the treatment comprising various dosage combinations of leucine, metformin and sildenafil, b.i.d., and placebo for non-alcoholic fatty liver disease (NAFLD) as shown in Table 30. All drugs will be administered b.i.d. Total daily drug doses are as shown in Table 30.

TABLE 30

Dosing protocol for adults
Dosing per Administration a. Placebo
b. Leucine, 1.11 g + 250 mg metformin + 0.5 mg sildenafil, fixed dose
c. Leucine, 1.11 g + 250 mg metformin +1.0 mg sildenafil, fixed dose
d. Leucine, 1.11 g + 500 mg metformin + 0.5 mg sildenafil, fixed dose
e. Leucine, 1.11 g + 500 mg metformin + 1.0 mg sildenafil, fixed dose.
All doses are administered b.i.d (twice a day). Total daily drug doses are as follows:
leucine: 2.2 g (arms B, C and D)
metformin: 500 mg (arms B and C); 1,000 mg (arms D and E)
sildenafil: 1.0 mg (arms B and D); 2.0 mg (arms C and E)

The combination treatment is a formulation of the essential amino acid L-leucine, metformin and sildenafil. All unit doses are formulated in tablets or capsules. Each unit dose can comprise 1 tablet or 1 capsule, 2 tablets or 2 capsules, or 3 tablets or 3 capsules. In some cases, each tablet or capsule can comprise differing amounts of leucine, metformin and sildenafil. In some cases, each tablet or capsule in a dose unit can be of different colors. For example, the various amount of leucine, metformin and sildenafil in a dose unit can be denoted by different colors. Non-limiting examples of dosing in a tablet or a capsule are listed in Table 31. Combinations of the tablets or capsules can be used to meet the required dosing per administration. For example, a dosing of 1110 mg of leucine, 250 mg of metformin and 0.5 mg of sildenafil can be met by a first tablet that contains 1110 mg of leucine, 0 mg of metformin, and 0 mg of sildenafil and a second tablet that contains 250 mg of metformin and 0.5 mg of sildenafil. There are several advantages of having differing amounts of components in the different tablets or capsules. For example, such approach can facilitate uniform mixing in the manufacturing process. Other advantages of the approach are improving weight control and providing low weight variations.

TABLE 31

Exemplary dosing in a tablet or capsule for adult.
Dosing in a tablet/capsule for adult

| Leucine (mg) | Metformin (mg) | Sildenafil (mg) |
| --- | --- | --- |
| 550 | 250 | 0 |
| 550 | 250 | 0.5 |
| 550 | 250 | 1 |
| 550 | 250 | 2 |
| 550 | 500 | 0 |
| 550 | 500 | 0.5 |
| 550 | 500 | 1 |
| 550 | 500 | 2 |

TABLE 31-continued

Exemplary dosing in a tablet or capsule for adult.
Dosing in a tablet/capsule for adult

| Leucine (mg) | Metformin (mg) | Sildenafil (mg) |
| --- | --- | --- |
| 550 | 0 | 0 |
| 550 | 0 | 0.5 |
| 550 | 0 | 1 |
| 550 | 0 | 2 |
| 1100 | 0 | 0 |
| 1100 | 0 | 0.5 |
| 1100 | 0 | 1 |
| 1100 | 0 | 2 |
| 0 | 250 | 0 |
| 0 | 250 | 0.5 |
| 0 | 250 | 1 |
| 0 | 250 | 2 |
| 0 | 500 | 0 |
| 0 | 500 | 0.5 |
| 0 | 500 | 1 |
| 0 | 500 | 2 |
| 0 | 0 | 0.5 |
| 0 | 0 | 1.0 |
| 0 | 0 | 2 |

In general, these doses can be administered over 1 tablet or capsule, 2 tablets or capsules, or 3 tablets or capsules. All unit doses are provided in coded tablets or capsules to double-blind the medications to patients and trial staff. The total daily dose of L-leucine is about 1.1 g, about 2.2 g, or less; the total daily dose of metformin is about 250 mg, 500 mg, 1000 mg, or less; while the total daily dose of sildenafil is about 0.5 mg, about 1.0 mg, about 2.0 mg, about 3.0 mg, about 4.0 mg, or less. In some embodiments, the total daily dose of sildenafil is limited to be less than 4.0 mg.

Subjects meet the following criteria for inclusion in this study. Subjects are males or non-pregnant females, 18-75 years of age inclusive. Subjects have histological evidence of NASH based on diagnostic liver biopsy, either during screening or from historical liver biopsy within the preceding 90 days, and a NAS score ≥4, with a score of ≥1 in each NAS component (e.g., steatosis, ballooning, and lobular inflammation); have HbA1c of 9% or less, be otherwise stable health for preceding 12 weeks; and have BMI of 45 $kg/m^2$ or less.

In addition, subjects are not in the treatment or have been treated with metformin, insulin, sildenafil or other PDE5 inhibitors such as tadalafil and vardenafil, alpha blockers, oral nitrates, thiazoladinediones or medications associated with increased hepatic steatosis within the preceding four weeks. Females subjects are not lactating, pregnant or unwilling to practice adequate contraception for duration of the study. Subjects do not have concomitant significant metabolic (other than diabetes), infectious, inflammatory, neoplastic or other non-liver disease. Excluded are also subjects who have history of alcohol abuse (e.g., consume at least 7 drinks or more per week for females and at least 14 drinks or more per week for males), recreational drug use within the past 3 months or failure on urinary drug screen; currently or recent (within the previous four weeks) use of steroids or presence of concomitant disease requiring steroid use; or recent (within the previous twelve weeks) serious infection, such as pneumonia or urinary tract infection.

The effects of the treatments versus placebo and diet on hepatic histological improvement in non-alcoholic fatty liver disease (NAFLD) are assessed using histological improvement in NAFLD, defined as a decrease in NAS score with no worsening of fibrosis and a decrease in NAFLD Activity Score (NAS), or resolution of NASH, or improvement in fibrosis, monitored during or at the end of the 12-month treatment. Treatment efficacy is also evaluated by measuring liver fat by proton-density-fat-fraction (PDFF) magnetic resonance imaging (MRI) (MRI PDFF), evaluating serum alanine aminotransferase (ALT) level, evaluating serum gamma glutamyl transferase (GGT), evaluating hepatic necro-inflammation as measured by circulating cytokeratin 18 (K18) level, evaluating liver stiffness as measured by transient elastography (TE), evaluating hepatic steatosis as measured by TE, evaluating fasting glucose, insulin, HbA1c and insulin sensitivity (HOMA$_{IR}$), evaluating blood lipids (cholesterol, LDL particle fractions, HDL sub-fractions, Lipoprotein (a) "Lp(a)", triglycerides), and evaluating C-reactive protein (CRP) or inflammation.

Subjects receiving the combination treatment are expected to have histological improvement in NAFLD Activity Score (NAS) during the 12-month treatment, and changes in biomarker levels over the 12-months period. For example, subjects respond to the combination treatment are expected to have reduced hepatic fat, reduced serum ALT level, reduced circulating K18 level, reduced liver fibrosis, reduced hepatic steatosis, reduced blood lipids, reduced inflammation, and increased insulin sensitivity. In comparison, the placebo group is expected to maintain significant hepatocellular injury, higher hepatic fat, higher blood lipids, higher inflammation, higher ALT level, and higher K18 level.

Example 13: Effects of Leucine, Metformin and Sildenafil Combination Treatment on Non-Alcoholic Fatty Liver Disease (NAFLD) in Children This is a 8-week randomized, double-blind, placebo-controlled trial for treatment of the leucine, metformin and sildenafil combination treatment non-alcoholic fatty liver disease (NAFLD) in children. A total of 48 patients are to be randomized with a goal of 40 patients to complete all assessments over 8 weeks. Patients with histologically confirmed NASH will be randomized to five arms (n=20/arm) are as shown in Table 32. Patients are administered the combination treatment comprising various dosage combinations of leucine, metformin and sildenafil, b.i.d., and placebo for non-alcoholic fatty liver disease (NAFLD) as shown in Table 31. All drugs will be administered b.i.d. Total daily drug doses are as shown in Table 32.

TABLE 32

Dosing for clinical protocol for children

| Study Design | Unit dose: |
|---|---|
| | a) Placebo |
| | b) Leucine 1.11 g + 500 mg metformin + 1.0 mg sildenafil |
| | All doses are administered b.i.d (twice a day). Total daily drug doses are as follows: |
| | leucine: 2.2 g (arm B) |
| | metformin: 1,000 mg (arm B) |
| | sildenafil: 2.0 mg (arm B) |

The combination treatment is a formulation of the essential amino acid L-leucine, metformin and sildenafil. All unit doses are formulated in tablets or capsules. Each unit dose can comprise 1 tablet or 1 capsule, 2 tablets or 2 capsules, or 3 tablets or 3 capsules. In some cases, each tablet or capsule can comprise various amount of leucine, metformin and sildenafil. In some cases, each tablet or capsule in a dose unit can be of different colors. For example, the various amount of leucine, metformin and sildenafil in a dose unit can be denoted by different colors. Non-limiting examples of dosing in a tablet or a capsule are listed in Table 33.

TABLE 33

Exemplary dosing in a tablet or capsule for children.
Dosing in each tablet/capsule for children

| Leucine (mg) | Metformin (mg) | Sildenafil (mg) |
|---|---|---|
| 300 | 100 | 0 |
| 300 | 100 | 0.3 |
| 300 | 100 | 0.4 |
| 300 | 100 | 0.5 |
| 300 | 100 | 1 |
| 300 | 100 | 2 |
| 300 | 200 | 0 |
| 300 | 200 | 0.3 |
| 300 | 200 | 0.4 |
| 300 | 200 | 0.5 |
| 300 | 200 | 1 |
| 300 | 200 | 2 |
| 300 | 250 | 0 |
| 300 | 250 | 0.3 |
| 300 | 250 | 0.4 |
| 300 | 250 | 0.5 |
| 300 | 250 | 1 |
| 300 | 250 | 2 |
| 500 | 100 | 0 |
| 500 | 100 | 0.3 |
| 500 | 100 | 0.4 |
| 500 | 100 | 0.5 |
| 500 | 100 | 1 |
| 500 | 100 | 2 |
| 500 | 200 | 0 |
| 500 | 200 | 0.3 |
| 500 | 200 | 0.4 |
| 500 | 200 | 0.5 |
| 500 | 200 | 1 |
| 500 | 200 | 2 |
| 500 | 250 | 0 |
| 500 | 250 | 0.3 |
| 500 | 250 | 0.4 |
| 500 | 250 | 0.5 |
| 500 | 250 | 1 |
| 500 | 250 | 2 |
| 1100 | 0 | 1 |
| 1100 | 500 | 0 |
| 0 | 100 | 1 |
| 0 | 200 | 1 |
| 0 | 250 | 1 |

In general, these doses can be administered over 1 tablet or capsule, 2 tablets or capsules, or 3 tablets or capsules. All unit doses be provided in coded tablets or capsules to double-blind the medications to patients and trial staff. The total daily dose of L-leucine is about 1.1 g, about 2.2 g, or less; the total daily dose of metformin is about 250 mg, 500 mg, 1000 mg, or less; while the total daily dose of sildenafil is about 0.5 mg, about 1.0 mg, about 2.0 mg, about 3.0 mg, about 4.0 mg, or less. In some embodiments, the total daily dose of sildenafil is limited to be less than 4.0 mg.

Subjects meet the following criteria for inclusion in this study. Subjects are males or females, 11-17 years of age inclusive. Subjects have histological evidence of NASH based on diagnostic liver biopsy, either during screening or from historical liver biopsy within the past six months, and elevated serum alanine aminotransferase (ALT) level of >60 IU/L; have HbA1c of at least 9% or more, be otherwise stable health for the preceding 12 weeks; and have BMI of 40 kg/m$^2$ or less. Subjects on insulin are on a single long acting insulin regime and the regime is stable for the past 4 weeks and remain stable throughout trial.

In addition, subjects are not in the treatment or have been treated with metformin, sildenafil, or thiazoladinediones within the preceding four weeks. Female subjects are not lactating, pregnant or unwilling to practice adequate contraception for duration of the study. Subjects do not have concomitant significant metabolic (other than diabetes), infectious, inflammatory, neoplastic or other non-liver disease. Excluded are also subjects who have currently or recent (within the previous four weeks) use of steroids or presence of concomitant disease requiring steroid use; or recent (within the previous twelve weeks) serious infection, such as pneumonia or urinary tract infection. Subjects do not have weight loss of 5% or more in the last 3 months.

The effects of the combination treatments versus placebo and diet on hepatic histological improvement in non-alcoholic fatty liver disease (NAFLD) are assessed by evaluating serum alanine aminotransferase (ALT) level, evaluating aspartate transaminase (AST) level, evaluating hepatic necro-inflammation as measured by circulating cytokeratin 18 (K18) level, evaluating insulin sensitivity, evaluating blood lipids (cholesterol, LDL particle fractions, HDL subfractions, Lipoprotein (a) "Lp(a)", triglycerides), and evaluating C-reactive protein (CRP) or inflammation.

Subjects receiving the combination treatment are expected to have reduced serum alanine aminotransferase (ALT) activity during the 8-week treatment, and changes in other biomarker levels during 8-week treatment. For example, subjects respond to the combination treatment are expected to have reduced AST level, reduced circulating K18 level, reduced blood lipids, reduced inflammation, and increased insulin sensitivity. In comparison, the placebo group is expected to maintain significant higher blood lipids, higher inflammation, higher ALT level, higher AST level and higher K18 level.

Example 14: Quantitation of Interactive Effects of Leucine, Metformin and Sildenafil on Liver Fibrosis This is a follow-up study of Example 10 conducted in the same animal model to assess optimal dose-ranging. NASH was induced using HFD (60% fat) supplemented with cholesterol (1.25%) and cholate 0.5%) as above. Following induction of NASH, animals were then randomized for eight weeks (n=10/group), as depicted in Table 34.

TABLE 34

| Example 14 experimental groups |
| --- |
| Low fat diet (LFD) Control |
| High fat-atherogenic diet (HF/ATH) control |
| HF/ATH + Leucine (24 g/kg diet) + metformin (0.5 g/kg diet; calculated human equivalent dose, 500 mg/day) + sildenafil (6.25 mg/kg diet; calculated human equivalent dose, 0.5 mg/day). |
| HF/ATH + Leucine (24 g/kg diet) + metformin (0.5 g/kg, calculated human equivalent dose, 500 mg/day) + sildenafil (12.5 mg/kg diet; calculated human equivalent dose, 1.0 mg/day). |
| HF/ATH + Leucine (24 g/kg diet) + metformin (0.5 g/kg, calculated human equivalent dose, 500 mg/day) + sildenafil (25 mg/kg diet; calculated human equivalent dose, 2.0 mg/day). |
| HF/ATH + Leucine (24 g/kg diet) + metformin (0.5 g/kg, calculated human equivalent dose, 500 mg/day) + sildenafil (50 mg/kg diet; calculated human equivalent dose, 4.0 mg/day). |
| HF/ATH + Leucine (24 g/kg diet) + metformin (0.5 g/kg, calculated human equivalent dose, 500 mg/day) + sildenafil (100 mg/kg diet; calculated human equivalent dose, 8 mg/day). |
| HF/ATH + Leucine (24 g/kg diet) + metformin (1.0 g/kg diet; calculated human equivalent dose, 1,000 mg/day) + |

TABLE 34-continued

| Example 14 experimental groups |
| --- |
| sildenafil (12.5 mg/kg diet; calculated human equivalent dose, 1.0 mg/day). |
| HF/ATH + Leucine (24 g/kg diet) + metformin (1.0 g/kg diet; calculated human equivalent dose, 1,000 mg/day) + sildenafil (50 mg/kg diet; calculated human equivalent dose, 4.0 mg/day). |

Histological evaluation using the NASH clinical research network scoring system was used to grade steatosis, inflammation, and fibrosis.

Figure 31:
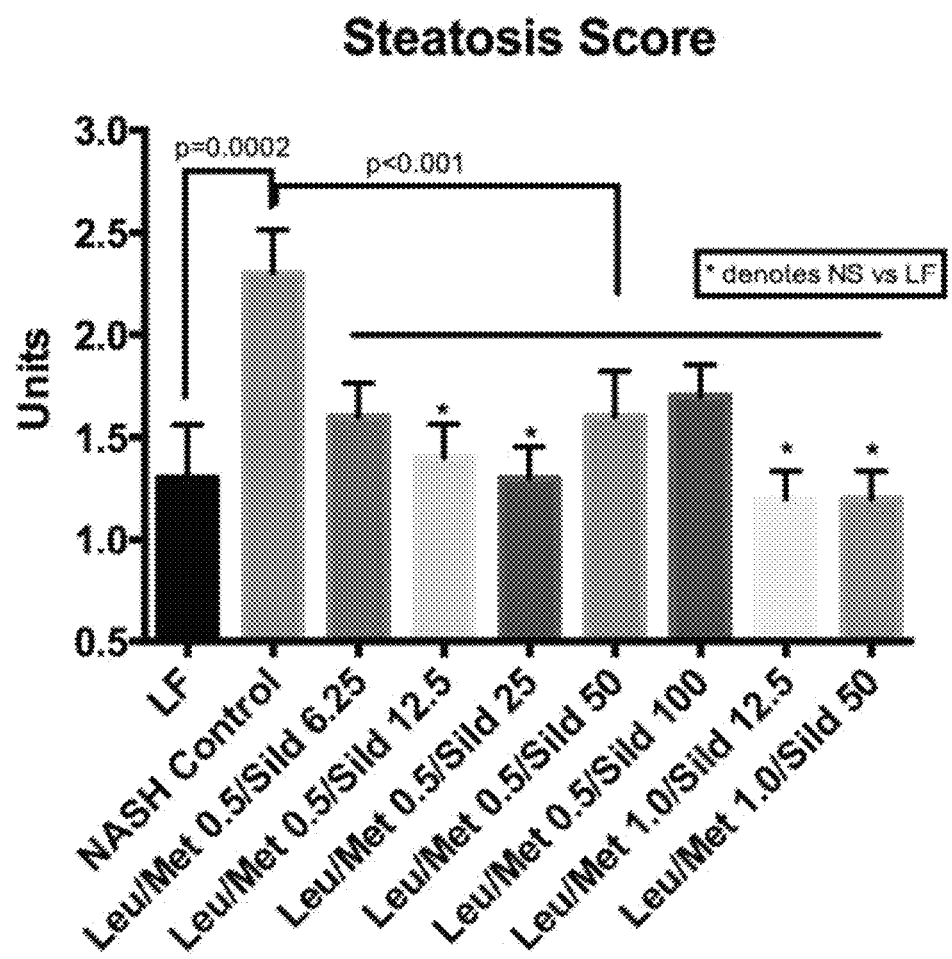
FIG. 31 depicts effects of leucine, metformin and sildenafil combinations on hepatic steatosis score.

Steatosis was markedly increased by the HF/ATH vs. LF diet and was significantly decreased by all doses of the triple combination of leucine, metformin and sildenafil (FIG. 31). A dose response reflecting progressive improvement in steatosis was evident with the lower dose of metformin combined with the lower doses (6.25-25 mg/kg, corresponding to human dosing of 0.5-2.0 mg/day) of sildenafil, while increasing sildenafil (50 mg/kg sildenafil and above, corresponding to human dosing of 4.0 mg/day sildenafil and above) negated this effect. When combined with the higher dose of metformin (1 g/kg, corresponding to human dosing of 1000 mg/day), both tested doses of sildenafil (12.5 mg/kg and 50 mg/kg of sildenafil) exerted comparable effects on steatosis (FIG. 31).

Figure 32:
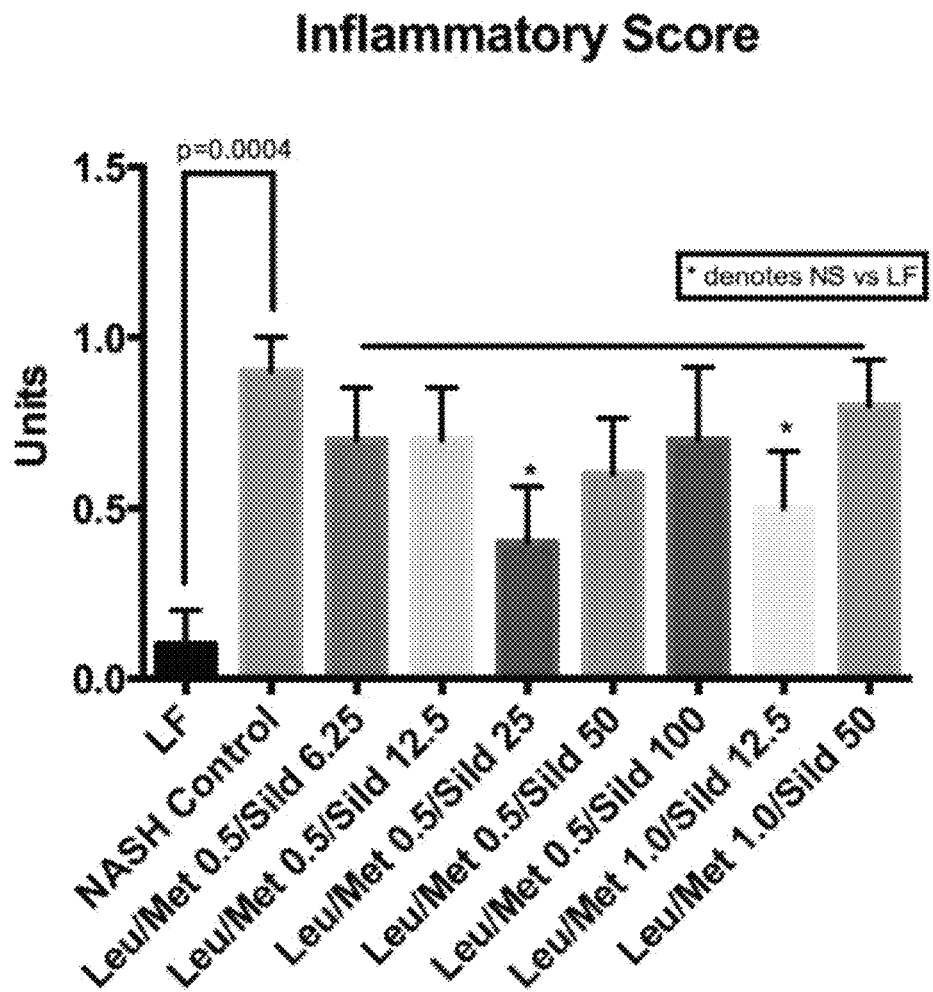
FIG. 32 depicts effects of leucine, metformin and sildenafil combinations on hepatic inflammatory score.
Figure 33:
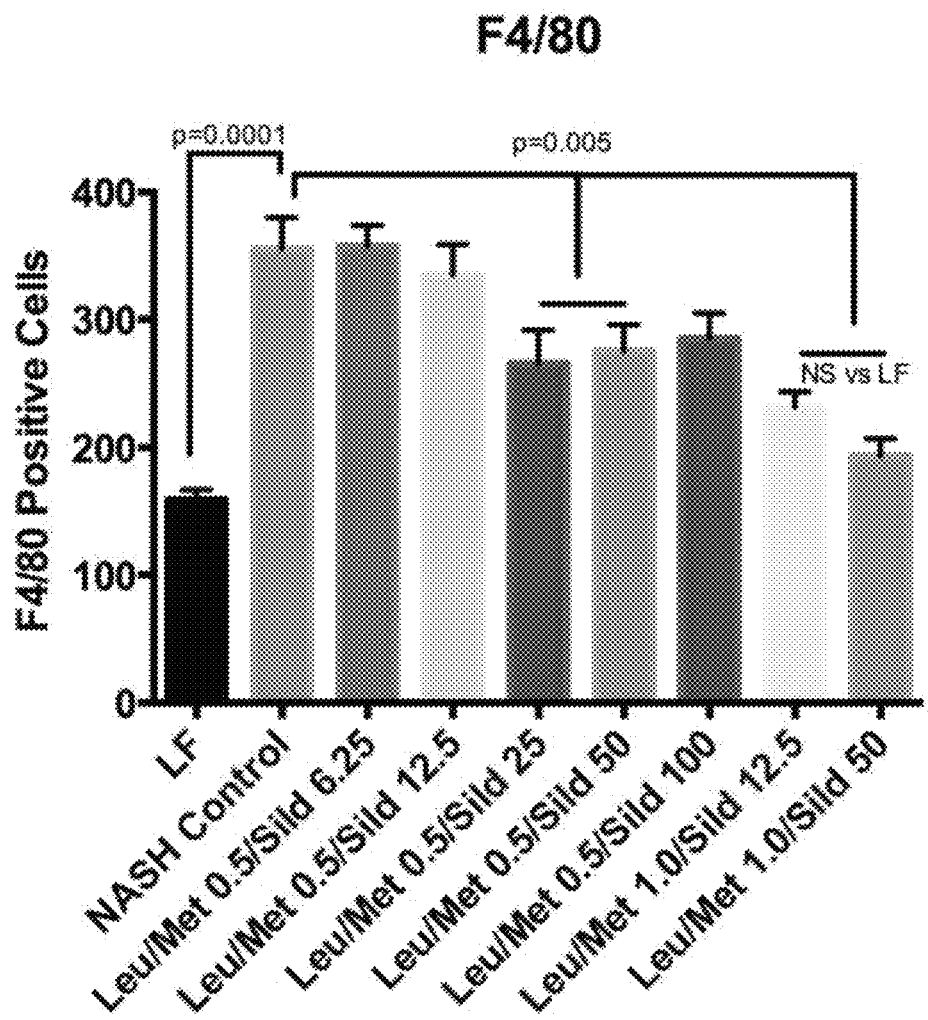
FIG. 33 depicts effects of leucine, metformin and sildenafil combinations on liver F4/80 immunohistochemistry.

Inflammation score (FIG. 32) and macrophage infiltration (via F4/80 immunohistochemistry, FIG. 33) exhibited a similar pattern, although increasing sildenafil from 12.5 mg/kg to 50 mg/kg at the higher dose of metformin attenuated the anti-inflammatory effect of this triple combination (FIG. 32).

Figure 34:
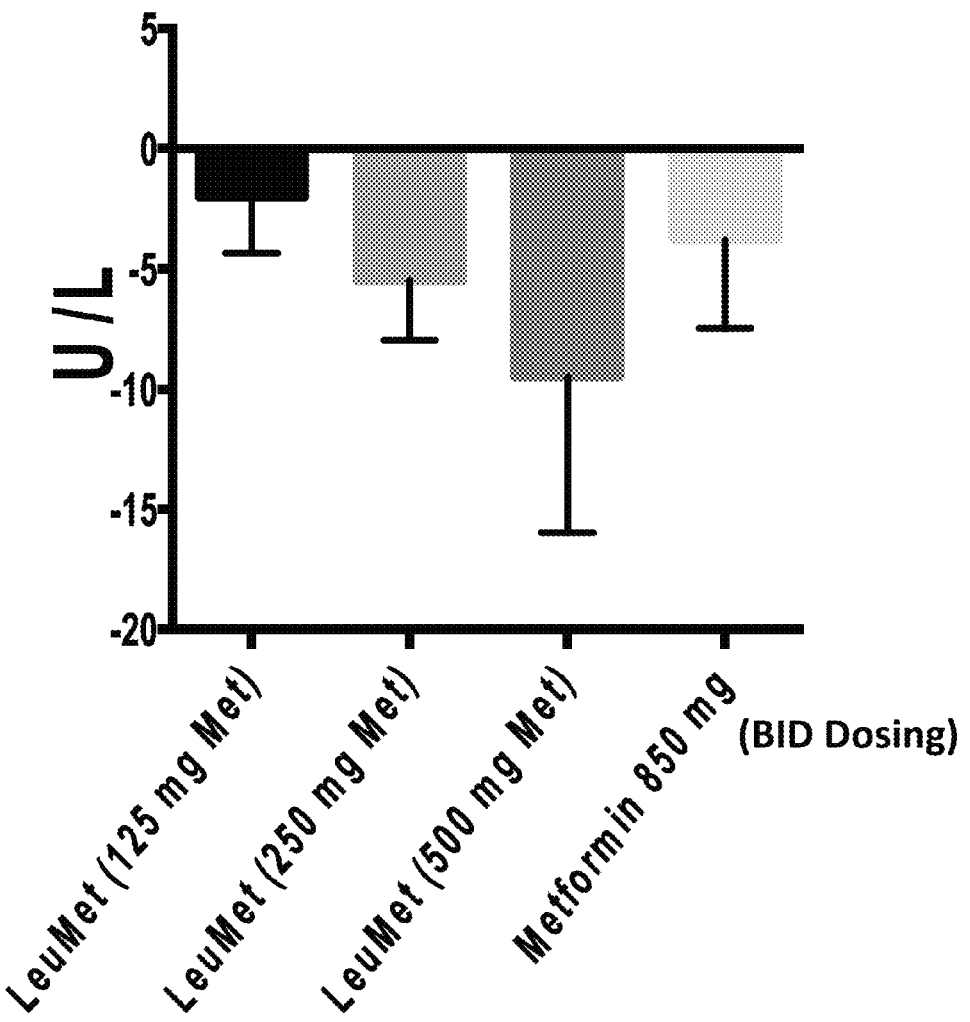
FIG. 34 illustrates serum ALT level change over 84 days of leucine+metformin treatment in subjects (female of age >19, male of age >30) with initial high ALT values at baseline.

These data demonstrate that combining leucine with low doses of metformin and sildenafil results in regression of steatohepatitis and fibrosis in a mouse model of severe NASH. When combined with the data on the two-way combinations of leucine-metformin and leucine-PDE5 inhibition, these data also suggest the desirable effects of the combination may be related to quantities of metformin and sildenafil combined with leucine in each dose. Translation of these preclinical data to human equivalent doses predict an optimal dose of sildenafil in the range of 1-2 mg/day, with higher doses (4.0 mg/day sildenafil and above) attenuating the benefit of the triple combination for steatosis, inflammation and fibrosis in this model. This beneficial effect of sildenafil in reducing hepatic steatosis, inflammation and fibrosis is unexpected as previous studies show that high dose of sildenafil can cause liver damage in humans. A low dose sildenafil in combination with leucine and metformin is preferred over a higher dose of sildenafil in treating hepatic disease. In some cases, the daily dose of sildenafil is limited to less than 10 mg/day, less than 9 mg/day, less than 8 mg/day, less than 7 mg/day, less than 6 mg/day, less than 5 mg/day, less than 4 mg/day, less than 3 mg/day, less than 2 mg/day, or less. Preferably, the daily dose of sildenafil is less than 4 mg/day. Statistical evaluation in this preclinical study of dose benefits of 1,000 vs 500 mg metformin/day in the triple combination does not show a clear distinction between the two. In comparison, clinical evaluation of the effects of a dual combination of leucine+metformin on a relevant outcome (ALT) indicates superiority of the 1,000 mg/day (500 mg b.i.d.) dose over a 500 mg/day dose of metformin. FIG. 34 illustrates serum ALT level change over 84 days of leucine+metformin treatment in subjects (female of age >19, male of age >30) with initial high ALT values at baseline. Treatment with 500 mg metformin in combination with leucine exerts synergistic effect when compared to treatment with high dose metformin (800 mg) alone.

It should be understood from the foregoing that, while particular implementations have been illustrated and described, various modifications can be made thereto and are contemplated herein. It is also not intended that the invention be limited by the specific examples provided within the specification. While the invention has been described with reference to the aforementioned specification, the descriptions and illustrations of the preferable embodiments herein are not meant to be construed in a limiting sense. Furthermore, it shall be understood that all aspects of the invention are not limited to the specific depictions, configurations or relative proportions set forth herein which depend upon a variety of conditions and variables. Various modifications in form and detail of the embodiments of the invention will be apparent to a person skilled in the art. It is therefore contemplated that the invention shall also cover any such modifications, variations and equivalents.

What is claimed is:

1. A method of reducing non-alcoholic steatohepatitis (NASH) in a subject in need thereof, comprising administering to the subject a composition comprising:
    a) an amount of leucine in the form of a free amino acid and/or metabolite thereof;
    b) an amount of metformin; and
    c) an amount of sildenafil;
wherein the amount of component (a) administered to the subject is about 0.25-3 g/day of leucine in the form of a free amino acid, and/or about 0.2-3 g/day of leucine metabolite;
wherein the amount of component (b) administered to the subject is about 10-1000 mg/day of metformin;
wherein the amount of component (c) administered to the subject is about 0.05-100 mg/day of sildenafil; and
wherein components (a), (b), and (c) are co-administered to the subject simultaneously as a single composition or sequentially.

2. The method of claim 1, wherein the leucine metabolite thereof is β-hydroxy β-methylbutyrate (HMB) or keto-isocaproic acid (KIC).

3. The method of claim 1, wherein the molar ratio of leucine to sildenafil in the composition is at least about 20.

4. The method of claim 1, wherein a sub-therapeutic amount of metformin is administered to the subject.

5. The method of claim 1, wherein component (a) comprises leucine in the form of a free amino acid, component (b) comprises metformin, and component (c) comprises sildenafil.

6. The method of claim 5, wherein the composition administered to the subject is formulated in a unit dose, and wherein the composition comprises:
    component (a) comprising about 900-1200 mg of leucine in the form of a free amino acid;
    (ii) component (b) comprising about 0.1-10 mg of sildenafil; and
    (iii) component (c) comprising about 200-550 mg of metformin.

7. The method of claim 6, wherein the unit dose is administered twice a day.

8. The method of claim 1, wherein the subject has been diagnosed with the non-alcoholic steatohepatitis (NASH), or exhibits a non-alcoholic fatty liver disease (NAFLD) selected from the group consisting of non-alcoholic fatty liver (NAFL), NASH-related cirrhosis and hepatic steatosis.

9. The method of claim 1, comprising administering the composition to the subject twice daily and the liver mass of the subject is decreased by 25% within 6 weeks.

10. The method of claim 1, wherein the composition is substantially free of one or more free amino acids selected from the group consisting of alanine, arginine, asparagine, aspartic acid, cysteine, glutamic acid, glutamine, glycine, histidine, isoleucine, lysine, methionine, phenylalanine, proline, serine, threonine, tryptophan, tyrosine, and valine.

11. The method of claim 1, wherein the administering of (a), (b), and (c) reduces non-alcoholic steatohepatitis (NASH) to a greater extent than administration of (a) alone, thereby reducing non-alcoholic steatohepatitis (NASH) in the subject.

12. The method of claim 11, wherein the non-alcoholic steatohepatitis (NASH) in the subject is evidenced by an accumulation of hepatic fat, fibrosis and/or inflammation detectable by one or more methods selected from the group consisting of ultrasonography, computed tomography (CT), magnetic resonance imaging, magnetic resonance spectroscopy (MRS), magnetic resonance elastography (MRE), transient elastography (TE), hepatic steatosis, inflammation and/or fibrosis detected by biopsy, and detection of a biomarker indicative of liver damage.

13. The method of claim 12, wherein the biomarker indicative of liver damage is elevated serum alanine aminotransferase, aspartate aminotransferase, and/or cytokeratin 18.

14. A method of treating non-alcoholic steatohepatitis (NASH) in a subject in need thereof, comprising administering to the subject a composition comprising:
    a. an amount of leucine in the form of a free amino acid and/or metabolite thereof;
    b. an amount of metformin; and
    c. an amount of sildenafil;
    wherein the amount of component (a) administered to the subject is about 0.25-3 g/day of leucine in the form of a free amino acid, and/or about 0.2-3 g/day of leucine metabolite;
    wherein the amount of component (b) administered to the subject is about 10-1000 mg/day of metformin;
    wherein the amount of component (c) administered to the subject is about 0.05-100 mg/day of sildenafil; and
    wherein components (a), (b), and (c) are co-administered to the subject simultaneously as a single composition or sequentially.

15. The method of claim 14, wherein the composition administered to the subject is formulated in a unit dose, and wherein the composition comprises:
    component (a) comprising about 900-1200 mg of leucine in the form of a free amino acid; and
    (ii) component (b) comprising about 200-550 mg of metformin and about 0.1-10 mg of sildenafil.

16. The method of claim 15, wherein the components of the unit dose are co-administered to the subject simultaneously as a single composition or sequentially, and the unit dose is administered twice a day.

17. The method of claim 1 or 14, wherein the composition further comprises a sirtuin pathway activator.

18. The method of claim 17, wherein the sirtuin pathway activator comprises an AMPK activator, a PGC-1α activator, a PDE5 specific inhibitor, a biguanide or a thiazolidinedione.

19. The method of claim 17, wherein the thiazolidinedione comprises rosiglitazone or pioglitazone.

20. The method of claim 17, wherein the amount of thiazolidinedione administered to the subject is about 0.1-4 mg of rosiglitazone or about 0.1-45 mg of pioglitazone.

21. The method of claim 18, wherein the PDE5 specific inhibitor is selected from the group consisting of icariin, tadalafil, vardenafil, avanafil, lodenafil, mirodenafil and udenafil.

22. The method of claim 18, wherein the amount of the PDE5 specific inhibitor is selected from the group consisting of about 1-2000 mg/day of icariin, about 0.01-20 mg/day of tadalafil, about 0.01-20 mg/day of vardenafil, about 1-200 mg/day of avanafil, about 1-200 mg/day of lodenafil, about 1-100 mg/day of mirodenafil, about 1-200 mg/day of udenafil, and about 1-2000 mg/day of zaprinast.

\* \* \* \* \*